United States Patent
Yan et al.

(10) Patent No.: US 11,364,284 B2
(45) Date of Patent: Jun. 21, 2022

(54) METHODS OF TREATING MYOINTIMAL PROLIFERATION

(71) Applicants: Inozyme Pharma, Inc., Boston, MA (US); Westfaelische Wilhelms-Universitaet Muenster, Münster (DE)

(72) Inventors: Yan Yan, Cheshire, CT (US); Anumeha Shah, Cheshire, CT (US); Ashmita Saigal, Stamford, CT (US); Herman Griffin, Waterford, CT (US); Susan Faas McKnight, Old Lyme, CT (US); Andre Marozsan, Milford, CT (US); Kim Askew, Lincoln, MA (US); Yvonne Nitschke, Münster (DE); Frank Rutsch, Münster (DE)

(73) Assignees: Inozyme Pharma, Inc., Boston, MA (US); Westfaelische Wilhelms-Universitaet Muenster, Münster (DE)

( * ) Notice: Subject to any disclaimer, the term of this patent is extended or adjusted under 35 U.S.C. 154(b) by 582 days.

(21) Appl. No.: 16/309,047

(22) PCT Filed: Jun. 15, 2017

(86) PCT No.: PCT/US2017/037695
§ 371 (c)(1),
(2) Date: Dec. 11, 2018

(87) PCT Pub. No.: WO2017/218786
PCT Pub. Date: Dec. 21, 2017

(65) Prior Publication Data
US 2020/0306349 A1    Oct. 1, 2020

Related U.S. Application Data

(60) Provisional application No. 62/350,936, filed on Jun. 16, 2016.

(51) Int. Cl.
| | | |
|---|---|---|
| *A61P 9/10* | (2006.01) | |
| *C12N 9/16* | (2006.01) | |
| *A61K 38/46* | (2006.01) | |
| *A01K 67/027* | (2006.01) | |
| *A61K 45/06* | (2006.01) | |

(52) U.S. Cl.
CPC ........ *A61K 38/465* (2013.01); *A01K 67/0271* (2013.01); *A01K 2227/105* (2013.01); *A01K 2267/03* (2013.01); *A61K 45/06* (2013.01); *C07K 2319/30* (2013.01); *C12Y 301/04001* (2013.01)

(58) Field of Classification Search
CPC ....... A61P 9/10; A61K 31/46; C07K 3319/30; C12Y 301/04001; C12N 9/16
See application file for complete search history.

(56) References Cited

U.S. PATENT DOCUMENTS

| | | | |
|---|---|---|---|
| 8,846,603 B2 | 9/2014 | Quinn et al. | |
| 9,540,621 B2 | 1/2017 | Quinn et al. | |
| 9,744,219 B2 | 8/2017 | Braddock | |
| 10,493,135 B2 | 12/2019 | Quinn et al. | |
| 2004/0224893 A1 | 11/2004 | Wang et al. | |
| 2017/0145393 A1 | 5/2017 | Quinn et al. | |
| 2018/0318400 A1 | 11/2018 | Quinn et al. | |
| 2020/0263153 A1 | 8/2020 | Khan et al. | |

FOREIGN PATENT DOCUMENTS

| | | |
|---|---|---|
| WO | 2006039480 A2 | 4/2006 |
| WO | 2011/113027 A2 | 9/2011 |
| WO | 2012/125182 A1 | 9/2012 |
| WO | 2014126965 A2 | 8/2014 |
| WO | 2016100803 A2 | 6/2016 |
| WO | 2016/187408 A1 | 11/2016 |
| WO | 2017/087936 A1 | 5/2017 |
| WO | WO 2017218786 A1 | 12/2017 |
| WO | WO 2019067502 A1 | 4/2019 |

OTHER PUBLICATIONS

Mackenzie et al. 2012; New insights into NPP1 function: Lessons from clinical and animal studies. Bone. 51:961-968.*
Albright, R., et al., "ENPP1-Fc prevents mortality and vascular calcifications in rodent model of generalized arterial calcification of infancy", NatureCommunications, vol. 6, No. 1, Dec. 1, 2015 (Dec. 1, 2015), pp. 1-11.
Belli et al., "Identification and characterization of a soluble form of the plasma cell membrane glycoprotein PC-1 (5'-nucleotide phosphodiesterase," The FEBS Journal, 217:421-428 (1993).
Goding, J W., et al., "Physiological and pathophysiological functions of the ecto-nucleotide pyrophosphatase/phosphodiesterase family", Biochimica Et Biophysica Acta. Molecular Basis of Dise, Amsterdam, NL, vol. 1638, No. 1, May 20, 2003 (May 20, 2003), pp. 1-19.
Jansen, S., et al., "Structure of NPP1, an Ectonucleotide Pyrophosphatase/Phosphodiesterase Involved in Tissue Calcification", Structure, vol. 20, No. 11, Nov. 1, 2012 (Nov. 1, 2012), pp. 1948-1959.
Johnson, K, et al., "Linked Deficiencies in Extracellular PPi and Osteopontin Mediate Pathologic Calcification Associated With Defective PC-1 and ANK Expression", Journal of Bone and Mineral Research, Jun. 1, 2003 (Jun. 1, 2003), pp. 994-1004.

(Continued)

*Primary Examiner* — Karen Cochrane Carlson

(74) *Attorney, Agent, or Firm* — Cooley LLP; Amy Mandragouras; Ariana D. Harris

(57) ABSTRACT

The present invention provides a method of treating myointimal proliferation by administering a recombinant human soluble ectonucleotide pyrophosphatase phosphodiesterase (hsNPP1), active fragment or fusion protein thereof.

18 Claims, 32 Drawing Sheets

Specification includes a Sequence Listing.

(56) References Cited

OTHER PUBLICATIONS

Rezg, R., et al., "Inhibitors of Vascular Calcification as Potential Therapeutic Targets", J. Nephrol, Jul.-Aug. 2011, vol. 24, No. 4: pp. 416-427.
Rutsch, F. et al., "Genetics in Arterial Calcification Pieces of a Puzzle and Cogs in a Wheel," Circulation Research, vol. 109:578-592 (2011).
Rutsch, F. et al., "Hypophosphatemia, Hyperphosphaturia, and Bisphosphonate Treatment Are Associated With Survival Beyond Infancy in Generalized Arterial Calcification of Infancy," Circ Cardiovasc Genet., vol. 1(2): 133-140 (2008).
Stefan, C., et al., "NPP-type ectophosphodiesterases: unity in diversity", Trends in Biochemical Sciences, Elsevier, Amsterdam, NL, vol. 30, No. 10, Oct. 1, 2005 (Oct. 1, 2005), pp. 542-550.
Terkeltaub, R., "Physiologic and pathologic functions of the NPP nucleotide pyrophosphatase/phosphodiesterase family focusing on NPP1 in calcification", Purinergic Signalling, Kluwer Academic Publishers, DO, vol. 2, No. 2, Jun. 1, 2012 (Jun. 1, 2012), pp. 371-377.
International Preliminary Report on Patentabililty, PCT/US2017/037695, dated Sep. 4, 2018, 8 pages.
International Search Report and Written Opinion, PCT/US2017/037695, dated Sep. 8, 2017, 11 pages.
Nitschke, Y et al., "Npp1 promotes atherosclerosis in ApoE knock-out mice," Journal of Cellular and Molecular Medicine,vol. 15(11):2273-2283 (2011).
Serrano, R. et al., "Mono-allelic and bi-allelic ENPP1 deficiency promote post-injury neointimal hyperplasia associated with increased C/EBP homologous protein expression", Atherosclerosis, vol. 233 (2):493-502 (2014).
Askew, K., "Enpp1 Enzyme replacement therapy for generalized arterial calcification of infancy," Alexion Pharmaceuticals, Jul. 4, 2016, 25 pages.
International Preliminary Report on Patentability, PCT/US2018/052795, dated Mar. 31, 2020, 7 pages.
International Search Report and Written Opinion, PCT/US2018/052795, dated Dec. 11, 2018, 11 pages.
Khan, T. et al., "ENPP1 enzyme replacement therapy improves blood pressure and cardiovascular function in a mouse model of generalized arterial calcification of infancy," Disease Models & Mechanisms, 11(10):dmm035691, 14 pages (2018).
Rashdan, N.A. et al., "New perspectives on rare connective tissue calcifying diseases," Current Opinion in Pharmacology, 28:14-23 (2016).

* cited by examiner

Data represented as MEAN ± SEM for n=3 replicates

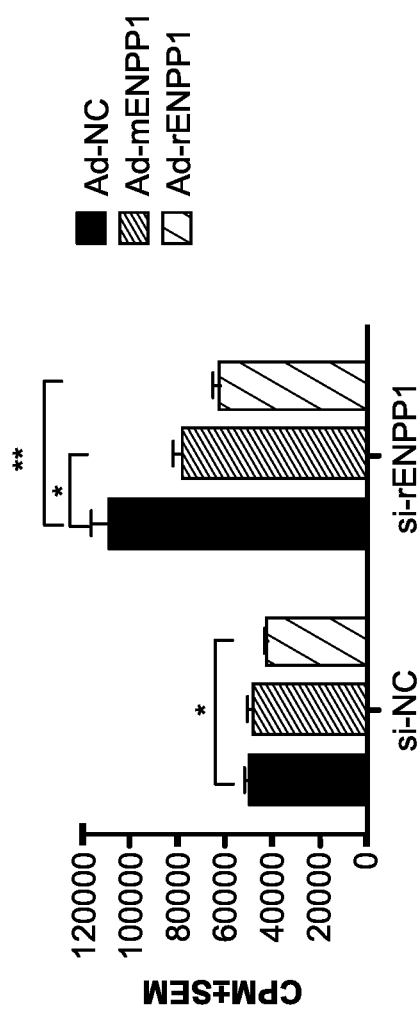
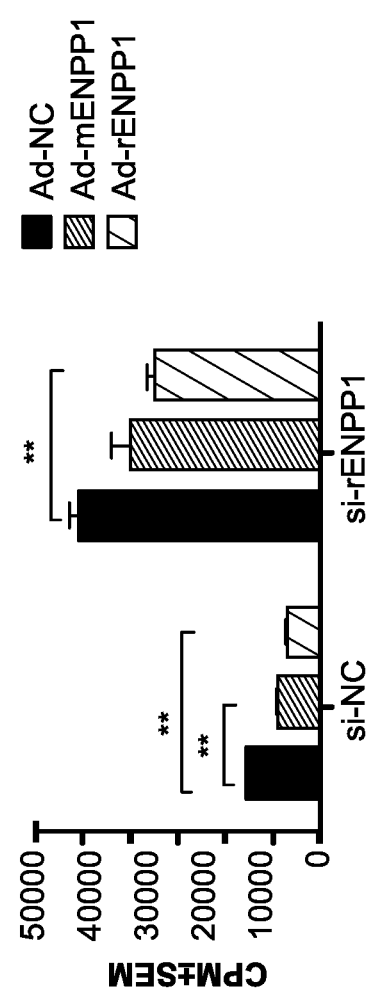

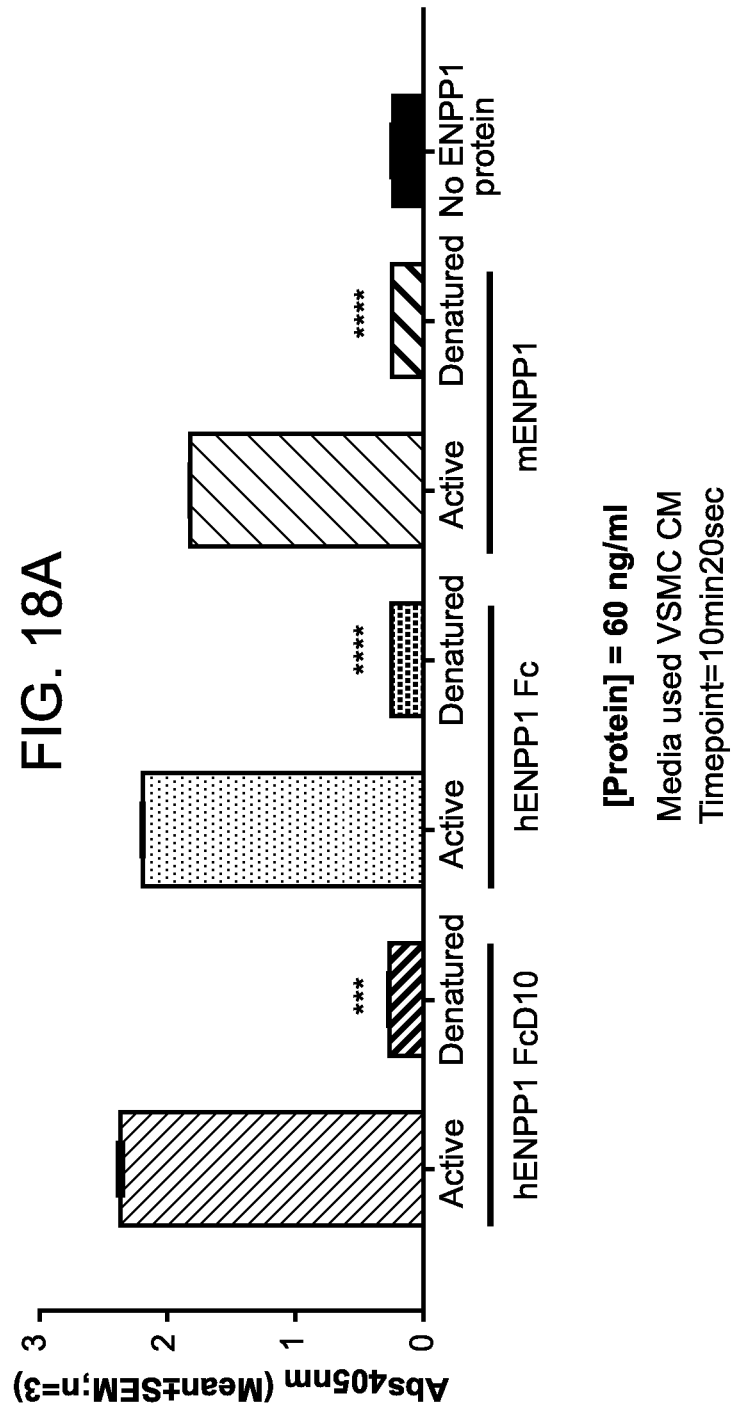

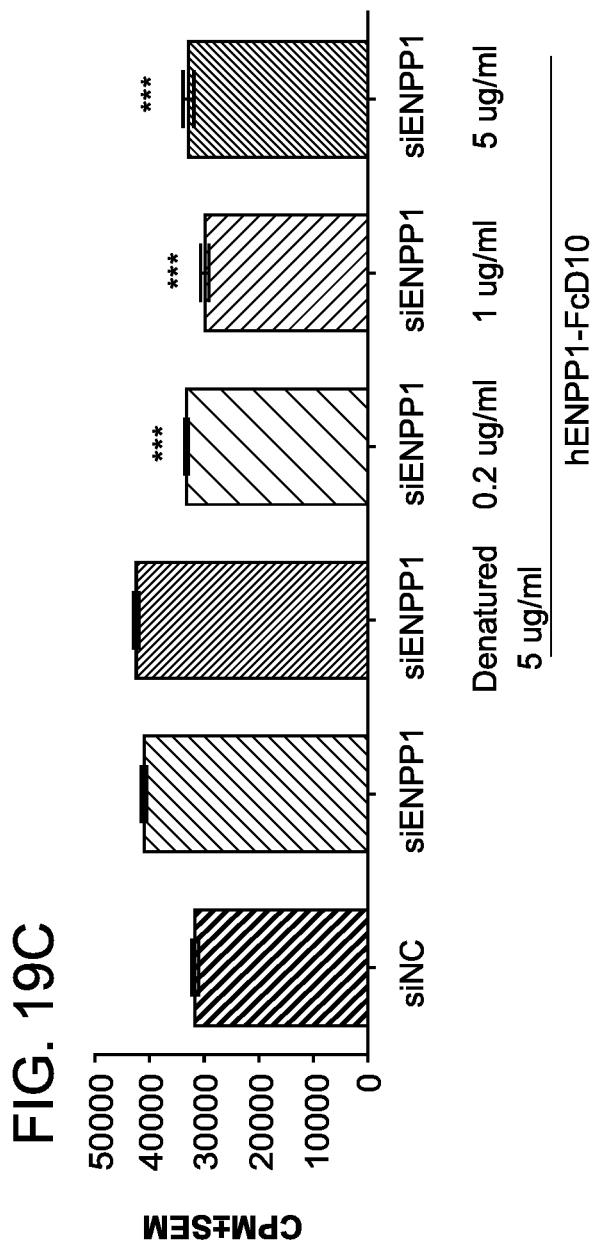

qRT-PCR

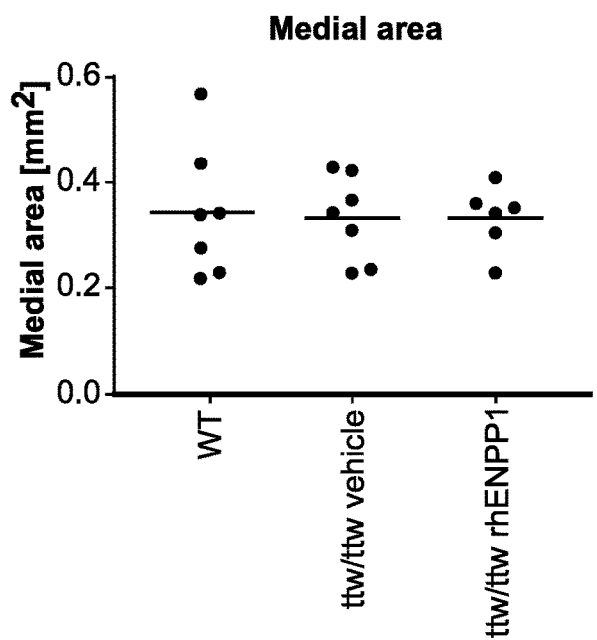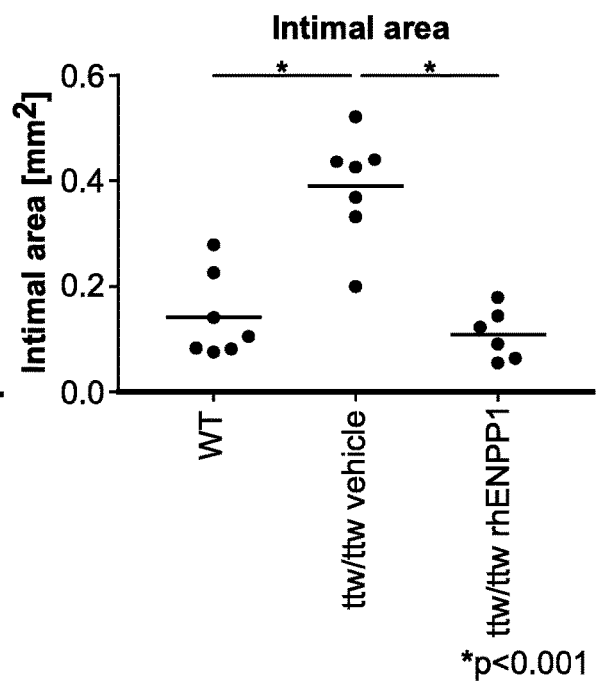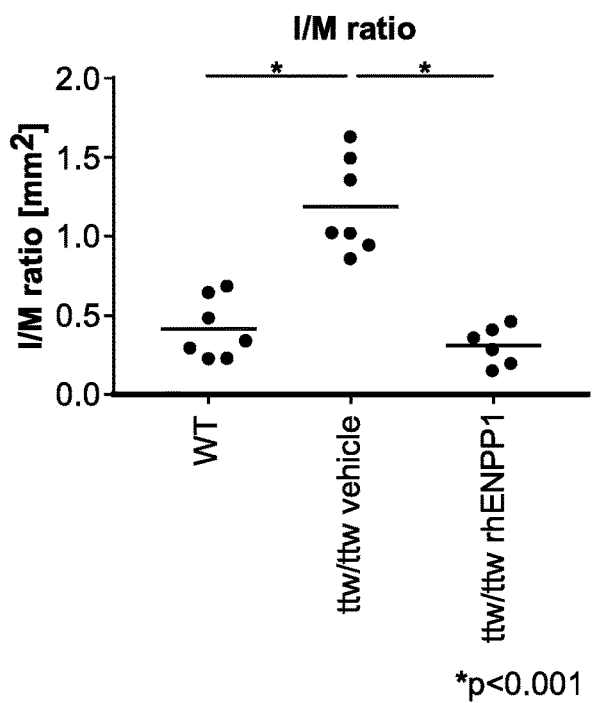

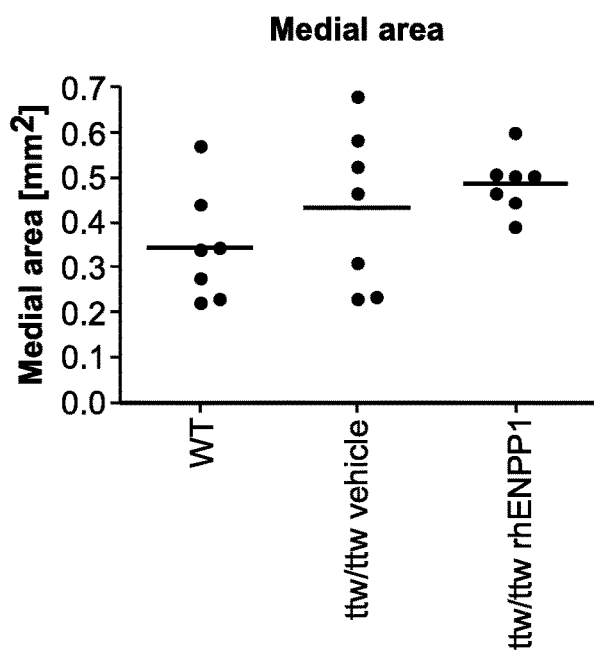
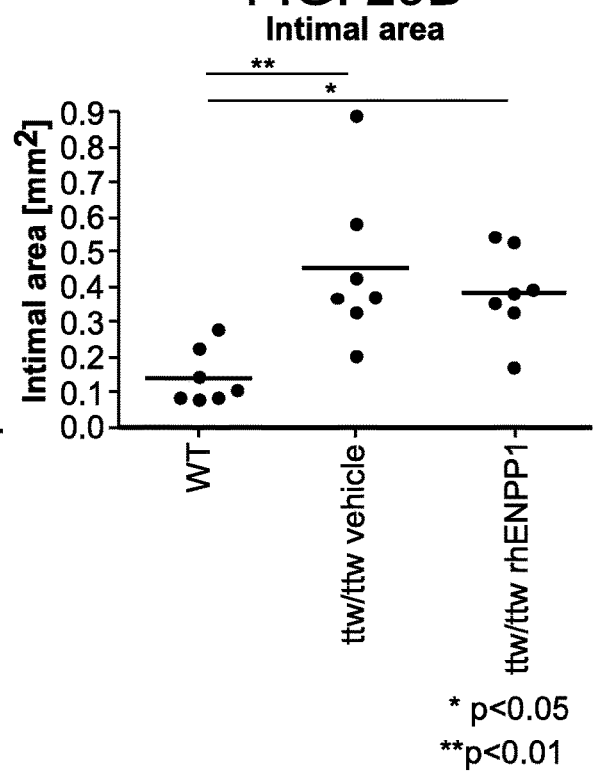
* p<0.05
**p<0.01
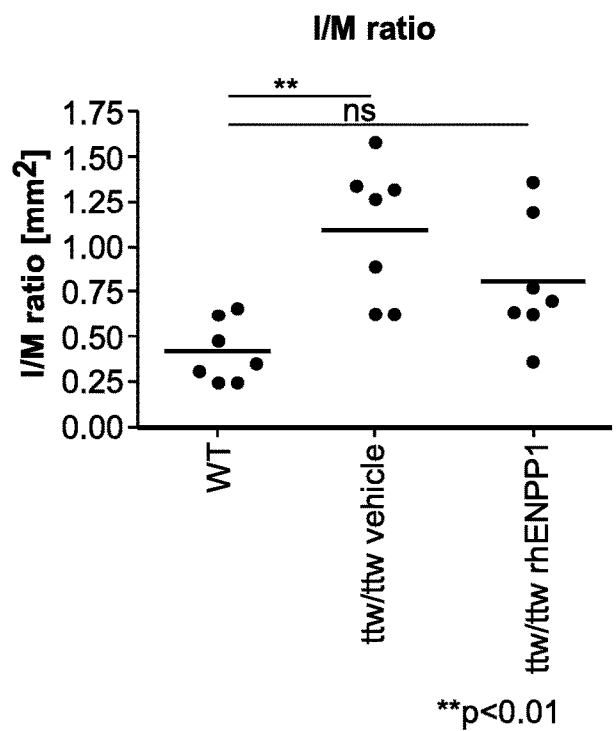
**p<0.01

SEQUENCE LISTING

<160> NUMBER OF SEQ ID NOS: 21

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Gly Ser Arg Gly Gly Glu Gly

-continued

```
1               5                   10                  15
Gly Arg Ala Pro Arg Glu Gly Pro Ala Gly Asn Gly Arg Asp Arg Gly
                20                  25                  30
Arg Ser His Ala Ala Glu Ala Pro Gly Asp Pro Gln Ala Ala Ala Ser
                35                  40                  45
Leu Leu Ala Pro Met Asp Val Gly Glu Glu Pro Leu Glu Lys Ala Ala
50                      55                  60
Arg Ala Arg Thr Ala Lys Asp Pro Asn Thr Tyr Lys Val Leu Ser Leu
65                  70                  75                  80
Val Leu Ser Val Cys Val Leu Thr Thr Ile Leu Gly Cys Ile Phe Gly
                85                  90                  95
Leu Lys Pro Ser Cys Ala Lys Glu Val Lys Ser Cys Lys Gly Arg Cys
                100                 105                 110
Phe Glu Arg Thr Phe Gly Asn Cys Arg Cys Asp Ala Ala Cys Val Glu
                115                 120                 125
Leu Gly Asn Cys Cys Leu Asp Tyr Gln Glu Thr Cys Ile Glu Pro Glu
                130                 135                 140
His Ile Trp Thr Cys Asn Lys Phe Arg Cys Gly Glu Lys Arg Leu Thr
145                 150                 155                 160
Arg Ser Leu Cys Ala Cys Ser Asp Asp Cys Lys Asp Lys Gly Asp Cys
                165                 170                 175
Cys Ile Asn Tyr Ser Ser Val Cys Gln Gly Glu Lys Ser Trp Val Glu
                180                 185                 190
Glu Pro Cys Glu Ser Ile Asn Glu Pro Gln Cys Pro Ala Gly Phe Glu
                195                 200                 205
Thr Pro Pro Thr Leu Leu Phe Ser Leu Asp Gly Phe Arg Ala Glu Tyr
                210                 215                 220
Leu His Thr Trp Gly Gly Leu Leu Pro Val Ile Ser Lys Leu Lys Lys
225                 230                 235                 240
Cys Gly Thr Tyr Thr Lys Asn Met Arg Pro Val Tyr Pro Thr Lys Thr
                245                 250                 255
Phe Pro Asn His Tyr Ser Ile Val Thr Gly Leu Tyr Pro Glu Ser His
                260                 265                 270
Gly Ile Ile Asp Asn Lys Met Tyr Asp Pro Lys Met Asn Ala Ser Phe
                275                 280                 285
Ser Leu Lys Ser Lys Glu Lys Phe Asn Pro Glu Trp Tyr Lys Gly Glu
                290                 295                 300
Pro Ile Trp Val Thr Ala Lys Tyr Gln Gly Leu Lys Ser Gly Thr Phe
305                 310                 315                 320
Phe Trp Pro Gly Ser Asp Val Glu Ile Asn Gly Ile Phe Pro Asp Ile
                325                 330                 335
Tyr Lys Met Tyr Asn Gly Ser Val Pro Phe Glu Glu Arg Ile Leu Ala
                340                 345                 350
Val Leu Gln Trp Leu Gln Leu Pro Lys Asp Glu Arg Pro His Phe Tyr
                355                 360                 365
Thr Leu Tyr Leu Glu Glu Pro Asp Ser Ser Gly His Ser Tyr Gly Pro
                370                 375                 380
Val Ser Ser Glu Val Ile Lys Ala Leu Gln Arg Val Asp Gly Met Val
385                 390                 395                 400
Gly Met Leu Met Asp Gly Leu Lys Glu Leu Asn Leu His Arg Cys Leu
                405                 410                 415
Asn Leu Ile Leu Ile Ser Asp His Gly Met Glu Gln Gly Ser Cys Lys
                420                 425                 430
```

```
Lys Tyr Ile Tyr Leu Asn Lys Tyr Leu Gly Asp Val Lys Asn Ile Lys
            435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
                500                 505                 510

Tyr Leu Asp Pro Gln Trp Gln Leu Ala Leu Asn Pro Ser Glu Arg Lys
                515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
                580                 585                 590

His Leu Leu Lys Asn Pro Val Tyr Thr Pro Lys His Pro Lys Glu Val
                595                 600                 605

His Pro Leu Val Gln Cys Pro Phe Thr Arg Asn Pro Arg Asp Asn Leu
                610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
                660                 665                 670

Leu Leu Ser Gln His Gln Phe Met Ser Gly Tyr Ser Gln Asp Ile Leu
                675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
                740                 745                 750

Tyr Ser Glu Ala Leu Leu Thr Thr Asn Ile Val Pro Met Tyr Gln Ser
                755                 760                 765

Phe Gln Val Ile Trp Arg Tyr Phe His Asp Thr Leu Leu Arg Lys Tyr
                770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
                820                 825                 830

Ile Val Leu Thr Ser Cys Lys Asp Thr Ser Gln Thr Pro Leu His Cys
                835                 840                 845
```

```
Glu Asn Leu Asp Thr Leu Ala Phe Ile Leu Pro His Arg Thr Asp Asn
            850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
            915                 920                 925

<210> SEQ ID NO 2
<211> LENGTH: 827
<212> TYPE: PRT
<213> ORGANISM: Homo sapiens

<400> SEQUENCE: 2

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30

Asn Cys Cys Leu Asp Tyr Gln Glu Thr Cys Ile Glu Pro Glu His Ile
        35                  40                  45

Trp Thr Cys Asn Lys Phe Arg Cys Gly Glu Lys Arg Leu Thr Arg Ser
    50                  55                  60

Leu Cys Ala Cys Ser Asp Asp Cys Lys Asp Lys Gly Asp Cys Cys Ile
65                  70                  75                  80

Asn Tyr Ser Ser Val Cys Gln Gly Glu Lys Ser Trp Val Glu Glu Pro
                85                  90                  95

Cys Glu Ser Ile Asn Glu Pro Gln Cys Pro Ala Gly Phe Glu Thr Pro
            100                 105                 110

Pro Thr Leu Leu Phe Ser Leu Asp Gly Phe Arg Ala Glu Tyr Leu His
            115                 120                 125

Thr Trp Gly Gly Leu Leu Pro Val Ile Ser Lys Leu Lys Lys Cys Gly
    130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
        195                 200                 205

Trp Val Thr Ala Lys Tyr Gln Gly Leu Lys Ser Gly Thr Phe Phe Trp
    210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                245                 250                 255

Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
        275                 280                 285

Ser Glu Val Ile Lys Ala Leu Gln Arg Val Asp Gly Met Val Gly Met
    290                 295                 300
```

-continued

```
Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                325                 330                 335

Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
        355                 360                 365

Tyr Ser Phe Asn Tyr Glu Gly Ile Ala Arg Asn Leu Ser Cys Arg Glu
    370                 375                 380

Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
        435                 440                 445

Leu Phe Val Gly Tyr Gly Pro Gly Phe Lys His Gly Ile Glu Ala Asp
    450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
        515                 520                 525

Ser Cys Asn Pro Ser Ile Leu Pro Ile Glu Asp Phe Gln Thr Gln Phe
    530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
        595                 600                 605

Asp Phe Ser Asn Cys Leu Tyr Gln Asp Phe Arg Ile Pro Leu Ser Pro
    610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
            660                 665                 670

Val Ile Trp Arg Tyr Phe His Asp Thr Leu Leu Arg Lys Tyr Ala Glu
        675                 680                 685

Glu Arg Asn Gly Val Asn Val Val Ser Gly Pro Val Phe Asp Phe Asp
    690                 695                 700

Tyr Asp Gly Arg Cys Asp Ser Leu Glu Asn Leu Arg Gln Lys Arg Arg
705                 710                 715                 720
```

```
Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
        755                 760                 765

Ser Cys Val His Gly Lys His Asp Ser Ser Trp Val Glu Glu Leu Leu
    770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp
            820                 825

<210> SEQ ID NO 3
<211> LENGTH: 1058
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30

Asn Cys Cys Leu Asp Tyr Gln Glu Thr Cys Ile Glu Pro Glu His Ile
        35                  40                  45

Trp Thr Cys Asn Lys Phe Arg Cys Gly Glu Lys Arg Leu Thr Arg Ser
    50                  55                  60

Leu Cys Ala Cys Ser Asp Asp Cys Lys Asp Lys Gly Asp Cys Cys Ile
65                  70                  75                  80

Asn Tyr Ser Ser Val Cys Gln Gly Glu Lys Ser Trp Val Glu Glu Pro
                85                  90                  95

Cys Glu Ser Ile Asn Glu Pro Gln Cys Pro Ala Gly Phe Glu Thr Pro
            100                 105                 110

Pro Thr Leu Leu Phe Ser Leu Asp Gly Phe Arg Ala Glu Tyr Leu His
        115                 120                 125

Thr Trp Gly Gly Leu Leu Pro Val Ile Ser Lys Leu Lys Lys Cys Gly
    130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
        195                 200                 205

Trp Val Thr Ala Lys Tyr Gln Gly Leu Lys Ser Gly Thr Phe Phe Trp
    210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
```

```
            245                 250                 255
Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
            275                 280                 285

Ser Glu Val Ile Lys Ala Leu Gln Arg Val Asp Gly Met Val Gly Met
            290                 295                 300

Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
            325                 330                 335

Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
            355                 360                 365

Tyr Ser Phe Asn Tyr Glu Gly Ile Ala Arg Asn Leu Ser Cys Arg Glu
            370                 375                 380

Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                    405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
            435                 440                 445

Leu Phe Val Gly Tyr Gly Pro Gly Phe Lys His Gly Ile Glu Ala Asp
            450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
            485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
            515                 520                 525

Ser Cys Asn Pro Ser Ile Leu Pro Ile Glu Asp Phe Gln Thr Gln Phe
530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
            565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
            595                 600                 605

Asp Phe Ser Asn Cys Leu Tyr Gln Asp Phe Arg Ile Pro Leu Ser Pro
            610                 615                 620

Val His Lys Cys Ser Phe Tyr Lys Asn Thr Lys Val Ser Tyr Gly
625                 630                 635                 640

Phe Leu Ser Pro Pro Gln Leu Asn Lys Asn Ser Ser Gly Ile Tyr Ser
                    645                 650                 655

Glu Ala Leu Leu Thr Thr Asn Ile Val Pro Met Tyr Gln Ser Phe Gln
            660                 665                 670
```

```
Val Ile Trp Arg Tyr Phe His Asp Thr Leu Leu Arg Lys Tyr Ala Glu
            675                 680                 685

Glu Arg Asn Gly Val Asn Val Ser Gly Pro Val Phe Asp Phe Asp
    690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
            755                 760                 765

Ser Cys Val His Gly Lys His Asp Ser Ser Trp Val Glu Glu Leu Leu
            770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp Pro Lys Ser Cys Asp
            820                 825                 830

Lys Thr His Thr Cys Pro Pro Cys Pro Ala Pro Glu Ala Ala Gly Ala
            835                 840                 845

Pro Ser Val Phe Leu Phe Pro Pro Lys Pro Lys Asp Thr Leu Met Ile
            850                 855                 860

Ser Arg Thr Pro Glu Val Thr Cys Val Val Val Asp Val Ser His Glu
865                 870                 875                 880

Asp Pro Glu Val Lys Phe Asn Trp Tyr Val Asp Gly Val Glu Val His
                885                 890                 895

Asn Ala Lys Thr Lys Pro Arg Glu Glu Gln Tyr Asn Ser Thr Tyr Arg
            900                 905                 910

Val Val Ser Val Leu Thr Val Leu His Gln Asp Trp Leu Asn Gly Lys
            915                 920                 925

Glu Tyr Lys Cys Lys Val Ser Asn Lys Ala Leu Pro Ala Pro Ile Glu
            930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
                965                 970                 975

Thr Cys Leu Val Lys Gly Phe Tyr Pro Ser Asp Ile Ala Val Glu Trp
            980                 985                 990

Glu Ser Asn Gly Gln Pro Glu Asn Asn Tyr Lys Thr Thr Pro Pro Val
            995                 1000                1005

Leu Asp Ser Asp Gly Ser Phe Phe Leu Tyr Ser Lys Leu Thr Val
    1010                1015                1020

Asp Lys Ser Arg Trp Gln Gln Gly Asn Val Phe Ser Cys Ser Val
    1025                1030                1035

Met His Glu Ala Leu His Asn His Tyr Thr Gln Lys Ser Leu Ser
    1040                1045                1050

Leu Ser Pro Gly Lys
    1055

<210> SEQ ID NO 4
<211> LENGTH: 1068
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30

Asn Cys Cys Leu Asp Tyr Gln Glu Thr Cys Ile Glu Pro His Ile
        35                  40                  45

Trp Thr Cys Asn Lys Phe Arg Cys Gly Glu Lys Arg Leu Thr Arg Ser
50                  55                  60

Leu Cys Ala Cys Ser Asp Cys Lys Asp Lys Gly Asp Cys Cys Ile
65                  70                  75                  80

Asn Tyr Ser Ser Val Cys Gln Gly Glu Lys Ser Trp Val Glu Pro
                85                  90                  95

Cys Glu Ser Ile Asn Glu Pro Gln Cys Pro Ala Gly Phe Glu Thr Pro
                100                 105                 110

Pro Thr Leu Leu Phe Ser Leu Asp Gly Phe Arg Ala Glu Tyr Leu His
            115                 120                 125

Thr Trp Gly Gly Leu Leu Pro Val Ile Ser Lys Leu Lys Lys Cys Gly
            130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
            195                 200                 205

Trp Val Thr Ala Lys Tyr Gln Gly Leu Lys Ser Gly Thr Phe Phe Trp
210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                245                 250                 255

Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
            275                 280                 285

Ser Glu Val Ile Lys Ala Leu Gln Arg Val Asp Gly Met Val Gly Met
            290                 295                 300

Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                325                 330                 335

Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
            355                 360                 365

Tyr Ser Phe Asn Tyr Glu Gly Ile Ala Arg Asn Leu Ser Cys Arg Glu

```
            370                 375                 380
Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
        435                 440                 445

Leu Phe Val Gly Tyr Gly Pro Gly Phe Lys His Gly Ile Glu Ala Asp
    450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
        515                 520                 525

Ser Cys Asn Pro Ser Ile Leu Pro Ile Glu Asp Phe Gln Thr Gln Phe
    530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
        595                 600                 605

Asp Phe Ser Asn Cys Leu Tyr Gln Asp Phe Arg Ile Pro Leu Ser Pro
    610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
            660                 665                 670

Val Ile Trp Arg Tyr Phe His Asp Thr Leu Leu Arg Lys Tyr Ala Glu
        675                 680                 685

Glu Arg Asn Gly Val Asn Val Val Ser Gly Pro Val Phe Asp Phe Asp
    690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
        755                 760                 765

Ser Cys Val His Gly Lys His Asp Ser Ser Trp Val Glu Glu Leu Leu
    770                 775                 780

Met Leu His Arg Ala Arg Ile Thr Asp Val Glu His Ile Thr Gly Leu
785                 790                 795                 800
```

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp Pro Lys Ser Cys Asp
            820                 825                 830

Lys Thr His Thr Cys Pro Pro Cys Pro Ala Pro Glu Ala Ala Gly Ala
            835                 840                 845

Pro Ser Val Phe Leu Phe Pro Pro Lys Pro Lys Asp Thr Leu Met Ile
        850                 855                 860

Ser Arg Thr Pro Glu Val Thr Cys Val Val Val Asp Val Ser His Glu
865                 870                 875                 880

Asp Pro Glu Val Lys Phe Asn Trp Tyr Val Asp Gly Val Glu Val His
                885                 890                 895

Asn Ala Lys Thr Lys Pro Arg Glu Glu Gln Tyr Asn Ser Thr Tyr Arg
            900                 905                 910

Val Val Ser Val Leu Thr Val Leu His Gln Asp Trp Leu Asn Gly Lys
        915                 920                 925

Glu Tyr Lys Cys Lys Val Ser Asn Lys Ala Leu Pro Ala Pro Ile Glu
    930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
                965                 970                 975

Thr Cys Leu Val Lys Gly Phe Tyr Pro Ser Asp Ile Ala Val Glu Trp
            980                 985                 990

Glu Ser Asn Gly Gln Pro Glu Asn Asn Tyr Lys Thr Thr Pro Pro Val
        995                 1000                1005

Leu Asp Ser Asp Gly Ser Phe Phe Leu Tyr Ser Lys Leu Thr Val
    1010                1015                1020

Asp Lys Ser Arg Trp Gln Gln Gly Asn Val Phe Ser Cys Ser Val
    1025                1030                1035

Met His Glu Ala Leu His Asn His Tyr Thr Gln Lys Ser Leu Ser
    1040                1045                1050

Leu Ser Pro Gly Lys Asp Asp Asp Asp Asp Asp Asp Asp Asp
    1055                1060                1065

<210> SEQ ID NO 5
<211> LENGTH: 819
<212> TYPE: PRT
<213> ORGANISM: Homo sapiens

<400> SEQUENCE: 5

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Pro Thr Leu Leu Phe Ser Leu Asp

```
            100             105             110
Gly Phe Arg Ala Glu Tyr Leu His Thr Trp Gly Gly Leu Leu Pro Val
            115             120             125

Ile Ser Lys Leu Lys Lys Cys Gly Thr Tyr Thr Lys Asn Met Arg Pro
            130             135             140

Val Tyr Pro Thr Lys Thr Phe Pro Asn His Tyr Ser Ile Val Thr Gly
145             150             155             160

Leu Tyr Pro Glu Ser His Gly Ile Ile Asp Asn Lys Met Tyr Asp Pro
            165             170             175

Lys Met Asn Ala Ser Phe Ser Leu Lys Ser Lys Glu Lys Phe Asn Pro
            180             185             190

Glu Trp Tyr Lys Gly Glu Pro Ile Trp Val Thr Ala Lys Tyr Gln Gly
            195             200             205

Leu Lys Ser Gly Thr Phe Phe Trp Pro Gly Ser Asp Val Glu Ile Asn
210             215             220

Gly Ile Phe Pro Asp Ile Tyr Lys Met Tyr Asn Gly Ser Val Pro Phe
225             230             235             240

Glu Glu Arg Ile Leu Ala Val Leu Gln Trp Leu Gln Leu Pro Lys Asp
            245             250             255

Glu Arg Pro His Phe Tyr Thr Leu Tyr Leu Glu Pro Asp Ser Ser
            260             265             270

Gly His Ser Tyr Gly Pro Val Ser Ser Glu Val Ile Lys Ala Leu Gln
            275             280             285

Arg Val Asp Gly Met Val Gly Met Leu Met Asp Gly Leu Lys Glu Leu
            290             295             300

Asn Leu His Arg Cys Leu Asn Leu Ile Leu Ile Ser Asp His Gly Met
305             310             315             320

Glu Gln Gly Ser Cys Lys Lys Tyr Ile Tyr Leu Asn Lys Tyr Leu Gly
            325             330             335

Asp Val Lys Asn Ile Lys Val Ile Tyr Gly Pro Ala Ala Arg Leu Arg
            340             345             350

Pro Ser Asp Val Pro Asp Lys Tyr Tyr Ser Phe Asn Tyr Glu Gly Ile
            355             360             365

Ala Arg Asn Leu Ser Cys Arg Glu Pro Asn Gln His Phe Lys Pro Tyr
            370             375             380

Leu Lys His Phe Leu Pro Lys Arg Leu His Phe Ala Lys Ser Asp Arg
385             390             395             400

Ile Glu Pro Leu Thr Phe Tyr Leu Asp Pro Gln Trp Gln Leu Ala Leu
            405             410             415

Asn Pro Ser Glu Arg Lys Tyr Cys Gly Ser Gly Phe His Gly Ser Asp
            420             425             430

Asn Val Phe Ser Asn Met Gln Ala Leu Phe Val Gly Tyr Gly Pro Gly
            435             440             445

Phe Lys His Gly Ile Glu Ala Asp Thr Phe Glu Asn Ile Glu Val Tyr
            450             455             460

Asn Leu Met Cys Asp Leu Leu Asn Leu Thr Pro Ala Pro Asn Asn Gly
465             470             475             480

Thr His Gly Ser Leu Asn His Leu Leu Lys Asn Pro Val Tyr Thr Pro
            485             490             495

Lys His Pro Lys Glu Val His Pro Leu Val Gln Cys Pro Phe Thr Arg
            500             505             510

Asn Pro Arg Asp Asn Leu Gly Cys Ser Cys Asn Pro Ser Ile Leu Pro
            515             520             525
```

```
Ile Glu Asp Phe Gln Thr Gln Phe Asn Leu Thr Val Ala Glu Glu Lys
    530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
            580                 585                 590

Arg Asn Asp Ser Phe Ser Thr Glu Asp Phe Ser Asn Cys Leu Tyr Gln
        595                 600                 605

Asp Phe Arg Ile Pro Leu Ser Pro Val His Lys Cys Ser Phe Tyr Lys
    610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
        675                 680                 685

Ser Gly Pro Val Phe Asp Phe Asp Tyr Asp Gly Arg Cys Asp Ser Leu
    690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
        755                 760                 765

Ser Ser Trp Val Glu Glu Leu Leu Met Leu His Arg Ala Arg Ile Thr
    770                 775                 780

Asp Val Glu His Ile Thr Gly Leu Ser Phe Tyr Gln Gly Arg Lys Glu
785                 790                 795                 800

Pro Val Ser Asp Ile Leu Lys Leu Lys Thr His Leu Pro Thr Phe Ser
                805                 810                 815

Gln Glu Asp

<210> SEQ ID NO 6
<211> LENGTH: 739
<212> TYPE: PRT
<213> ORGANISM: Homo sapiens

<400> SEQUENCE: 6

Glu Lys Ser Trp Val Glu Glu Pro Cys Glu Ser Ile Asn Glu Pro Gln
1               5                   10                  15

Cys Pro Ala Gly Phe Glu Thr Pro Pro Thr Leu Leu Phe Ser Leu Asp
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
    50                  55                  60

Val Tyr Pro Thr Lys Thr Phe Pro Asn His Tyr Ser Ile Val Thr Gly
65                  70                  75                  80
```

```
Leu Tyr Pro Glu Ser His Gly Ile Ile Asp Asn Lys Met Tyr Asp Pro
                85                  90                  95

Lys Met Asn Ala Ser Phe Ser Leu Lys Ser Lys Glu Lys Phe Asn Pro
            100                 105                 110

Glu Trp Tyr Lys Gly Glu Pro Ile Trp Val Thr Ala Lys Tyr Gln Gly
        115                 120                 125

Leu Lys Ser Gly Thr Phe Phe Trp Pro Gly Ser Asp Val Glu Ile Asn
130                 135                 140

Gly Ile Phe Pro Asp Ile Tyr Lys Met Tyr Asn Gly Ser Val Pro Phe
145                 150                 155                 160

Glu Glu Arg Ile Leu Ala Val Leu Gln Trp Leu Gln Leu Pro Lys Asp
                165                 170                 175

Glu Arg Pro His Phe Tyr Thr Leu Tyr Leu Glu Glu Pro Asp Ser Ser
            180                 185                 190

Gly His Ser Tyr Gly Pro Val Ser Ser Glu Val Ile Lys Ala Leu Gln
        195                 200                 205

Arg Val Asp Gly Met Val Gly Met Leu Met Asp Gly Leu Lys Glu Leu
210                 215                 220

Asn Leu His Arg Cys Leu Asn Leu Ile Leu Ile Ser Asp His Gly Met
225                 230                 235                 240

Glu Gln Gly Ser Cys Lys Lys Tyr Ile Tyr Leu Asn Lys Tyr Leu Gly
                245                 250                 255

Asp Val Lys Asn Ile Lys Val Ile Tyr Gly Pro Ala Ala Arg Leu Arg
            260                 265                 270

Pro Ser Asp Val Pro Asp Lys Tyr Tyr Ser Phe Asn Tyr Glu Gly Ile
        275                 280                 285

Ala Arg Asn Leu Ser Cys Arg Glu Pro Asn Gln His Phe Lys Pro Tyr
290                 295                 300

Leu Lys His Phe Leu Pro Lys Arg Leu His Phe Ala Lys Ser Asp Arg
305                 310                 315                 320

Ile Glu Pro Leu Thr Phe Tyr Leu Asp Pro Gln Trp Gln Leu Ala Leu
                325                 330                 335

Asn Pro Ser Glu Arg Lys Tyr Cys Gly Ser Gly Phe His Gly Ser Asp
            340                 345                 350

Asn Val Phe Ser Asn Met Gln Ala Leu Phe Val Gly Tyr Gly Pro Gly
        355                 360                 365

Phe Lys His Gly Ile Glu Ala Asp Thr Phe Glu Asn Ile Glu Val Tyr
370                 375                 380

Asn Leu Met Cys Asp Leu Leu Asn Leu Thr Pro Ala Pro Asn Asn Gly
385                 390                 395                 400

Thr His Gly Ser Leu Asn His Leu Leu Lys Asn Pro Val Tyr Thr Pro
                405                 410                 415

Lys His Pro Lys Glu Val His Pro Leu Val Gln Cys Pro Phe Thr Arg
            420                 425                 430

Asn Pro Arg Asp Asn Leu Gly Cys Ser Cys Asn Pro Ser Ile Leu Pro
        435                 440                 445

Ile Glu Asp Phe Gln Thr Gln Phe Asn Leu Thr Val Ala Glu Glu Lys
450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495
```

```
Tyr Ser Gln Asp Ile Leu Met Pro Leu Trp Thr Ser Tyr Thr Val Asp
                500                 505                 510

Arg Asn Asp Ser Phe Ser Thr Glu Asp Phe Ser Asn Cys Leu Tyr Gln
        515                 520                 525

Asp Phe Arg Ile Pro Leu Ser Pro Val His Lys Cys Ser Phe Tyr Lys
    530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
                580                 585                 590

Thr Leu Leu Arg Lys Tyr Ala Glu Glu Arg Asn Gly Val Asn Val Val
            595                 600                 605

Ser Gly Pro Val Phe Asp Phe Asp Tyr Asp Gly Arg Cys Asp Ser Leu
        610                 615                 620

Glu Asn Leu Arg Gln Lys Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
                660                 665                 670

Pro His Arg Thr Asp Asn Ser Glu Ser Cys Val His Gly Lys His Asp
            675                 680                 685

Ser Ser Trp Val Glu Glu Leu Leu Met Leu His Arg Ala Arg Ile Thr
        690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp

<210> SEQ ID NO 7
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110
```

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 8
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 9
<211> LENGTH: 1051
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
    130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg

```
                340             345             350
Pro Ser Asp Val Pro Lys Tyr Tyr Ser Phe Asn Tyr Glu Gly Ile
            355             360             365
Ala Arg Asn Leu Ser Cys Arg Glu Pro Asn Gln His Phe Lys Pro Tyr
370             375             380
Leu Lys His Phe Leu Pro Lys Arg Leu His Phe Ala Lys Ser Asp Arg
385             390             395             400
Ile Glu Pro Leu Thr Phe Tyr Leu Asp Pro Gln Trp Gln Leu Ala Leu
            405             410             415
Asn Pro Ser Glu Arg Lys Tyr Cys Gly Ser Gly Phe His Gly Ser Asp
            420             425             430
Asn Val Phe Ser Asn Met Gln Ala Leu Phe Val Gly Tyr Gly Pro Gly
            435             440             445
Phe Lys His Gly Ile Glu Ala Asp Thr Phe Glu Asn Ile Glu Val Tyr
            450             455             460
Asn Leu Met Cys Asp Leu Leu Asn Leu Thr Pro Ala Pro Asn Asn Gly
465             470             475             480
Thr His Gly Ser Leu Asn His Leu Leu Lys Asn Pro Val Tyr Thr Pro
            485             490             495
Lys His Pro Lys Glu Val His Pro Leu Val Gln Cys Pro Phe Thr Arg
            500             505             510
Asn Pro Arg Asp Asn Leu Gly Cys Ser Cys Asn Pro Ser Ile Leu Pro
            515             520             525
Ile Glu Asp Phe Gln Thr Gln Phe Asn Leu Thr Val Ala Glu Glu Lys
            530             535             540
Ile Ile Lys His Glu Thr Leu Pro Tyr Gly Arg Pro Arg Val Leu Gln
545             550             555             560
Lys Glu Asn Thr Ile Cys Leu Leu Ser Gln His Gln Phe Met Ser Gly
            565             570             575
Tyr Ser Gln Asp Ile Leu Met Pro Leu Trp Thr Ser Tyr Thr Val Asp
            580             585             590
Arg Asn Asp Ser Phe Ser Thr Glu Asp Phe Ser Asn Cys Leu Tyr Gln
            595             600             605
Asp Phe Arg Ile Pro Leu Ser Pro Val His Lys Cys Ser Phe Tyr Lys
            610             615             620
Asn Asn Thr Lys Val Ser Tyr Gly Phe Leu Ser Pro Pro Gln Leu Asn
625             630             635             640
Lys Asn Ser Ser Gly Ile Tyr Ser Glu Ala Leu Leu Thr Thr Asn Ile
            645             650             655
Val Pro Met Tyr Gln Ser Phe Gln Val Ile Trp Arg Tyr Phe His Asp
            660             665             670
Thr Leu Leu Arg Lys Tyr Ala Glu Glu Arg Asn Gly Val Asn Val Val
            675             680             685
Ser Gly Pro Val Phe Asp Phe Asp Tyr Asp Gly Arg Cys Asp Ser Leu
            690             695             700
Glu Asn Leu Arg Gln Lys Arg Arg Val Ile Arg Asn Gln Glu Ile Leu
705             710             715             720
Ile Pro Thr His Phe Phe Ile Val Leu Thr Ser Cys Lys Asp Thr Ser
            725             730             735
Gln Thr Pro Leu His Cys Glu Asn Leu Asp Thr Leu Ala Phe Ile Leu
            740             745             750
Pro His Arg Thr Asp Asn Ser Glu Ser Cys Val His Gly Lys His Asp
            755             760             765
```

Ser Ser Trp Val Glu Glu Leu Leu Met Leu His Arg Ala Arg Ile Thr
    770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp Glu Pro Lys Ser Cys Asp Lys Thr His Thr Cys Pro Pro
            820                 825                 830

Cys Pro Ala Pro Glu Leu Leu Gly Gly Pro Ser Val Phe Leu Phe Pro
        835                 840                 845

Pro Lys Pro Lys Asp Thr Leu Met Ile Ser Arg Thr Pro Glu Val Thr
    850                 855                 860

Cys Val Val Val Asp Val Ser His Glu Asp Pro Glu Val Lys Phe Asn
865                 870                 875                 880

Trp Tyr Val Asp Gly Val Glu Val His Asn Ala Lys Thr Lys Pro Arg
                885                 890                 895

Glu Glu Gln Tyr Asn Ser Thr Tyr Arg Val Val Ser Val Leu Thr Val
            900                 905                 910

Leu His Gln Asp Trp Leu Asn Gly Lys Glu Tyr Lys Cys Lys Val Ser
        915                 920                 925

Asn Lys Ala Leu Pro Ala Pro Ile Glu Lys Thr Ile Ser Lys Ala Lys
    930                 935                 940

Gly Gln Pro Arg Glu Pro Gln Val Tyr Thr Leu Pro Pro Ser Arg Glu
945                 950                 955                 960

Glu Met Thr Lys Asn Gln Val Ser Leu Thr Cys Leu Val Lys Gly Phe
                965                 970                 975

Tyr Pro Ser Asp Ile Ala Val Glu Trp Glu Ser Asn Gly Gln Pro Glu
            980                 985                 990

Asn Asn Tyr Lys Thr Thr Pro Pro Val Leu Asp Ser Asp Gly Ser Phe
        995                 1000                1005

Phe Leu Tyr Ser Lys Leu Thr Val Asp Lys Ser Arg Trp Gln Gln
    1010                1015                1020

Gly Asn Val Phe Ser Cys Ser Val Met His Glu Ala Leu His Asn
    1025                1030                1035

His Tyr Thr Gln Lys Ser Leu Ser Leu Ser Pro Gly Lys
    1040                1045                1050

<210> SEQ ID NO 10
<211> LENGTH: 1046
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60

-continued

```
Lys Asp Lys Gly Asp Cys Cys Ile Asn Tyr Ser Ser Val Cys Gln Gly
 65                  70                  75                  80

Glu Lys Ser Trp Val Glu Glu Pro Cys Glu Ser Ile Asn Glu Pro Gln
                 85                  90                  95

Cys Pro Ala Gly Phe Glu Thr Pro Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
    130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
    370                 375                 380

Leu Lys His Phe Leu Pro Lys Arg Leu His Phe Ala Lys Ser Asp Arg
385                 390                 395                 400

Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
    450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
```

```
            485                 490                 495
Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
            515                 520                 525

Ile Glu Asp Phe Gln Thr Gln Phe Asn Leu Thr Val Ala Glu Glu Lys
            530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
            580                 585                 590

Arg Asn Asp Ser Phe Ser Thr Glu Asp Phe Ser Asn Cys Leu Tyr Gln
            595                 600                 605

Asp Phe Arg Ile Pro Leu Ser Pro Val His Lys Cys Ser Phe Tyr Lys
            610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
            675                 680                 685

Ser Gly Pro Val Phe Asp Phe Asp Tyr Asp Gly Arg Cys Asp Ser Leu
            690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
            755                 760                 765

Ser Ser Trp Val Glu Glu Leu Leu Met Leu His Arg Ala Arg Ile Thr
            770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp Asp Lys Thr His Thr Cys Pro Pro Cys Pro Ala Pro Glu
            820                 825                 830

Leu Leu Gly Gly Pro Ser Val Phe Leu Phe Pro Pro Lys Pro Lys Asp
            835                 840                 845

Thr Leu Met Ile Ser Arg Thr Pro Glu Val Thr Cys Val Val Val Asp
850                 855                 860

Val Ser His Glu Asp Pro Glu Val Lys Phe Asn Trp Tyr Val Asp Gly
865                 870                 875                 880

Val Glu Val His Asn Ala Lys Thr Lys Pro Arg Glu Glu Gln Tyr Asn
                885                 890                 895

Ser Thr Tyr Arg Val Val Ser Val Leu Thr Val Leu His Gln Asp Trp
            900                 905                 910
```

-continued

```
Leu Asn Gly Lys Glu Tyr Lys Cys Lys Val Ser Asn Lys Ala Leu Pro
        915                 920                 925

Ala Pro Ile Glu Lys Thr Ile Ser Lys Ala Lys Gly Gln Pro Arg Glu
    930                 935                 940

Pro Gln Val Tyr Thr Leu Pro Pro Ser Arg Glu Glu Met Thr Lys Asn
945                 950                 955                 960

Gln Val Ser Leu Thr Cys Leu Val Lys Gly Phe Tyr Pro Ser Asp Ile
                965                 970                 975

Ala Val Glu Trp Glu Ser Asn Gly Gln Pro Glu Asn Asn Tyr Lys Thr
            980                 985                 990

Thr Pro Pro Val Leu Asp Ser Asp Gly Ser Phe Phe Leu Tyr Ser Lys
        995                 1000                1005

Leu Thr Val Asp Lys Ser Arg Trp Gln Gln Gly Asn Val Phe Ser
    1010                1015                1020

Cys Ser Val Met His Glu Ala Leu His Asn His Tyr Thr Gln Lys
1025                1030                1035

Ser Leu Ser Leu Ser Pro Gly Lys
    1040                1045

<210> SEQ ID NO 11
<211> LENGTH: 971
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Lys Ser Trp Val Glu Pro Cys Glu Ser Ile Asn Glu Pro Gln
1               5                   10                  15

Cys Pro Ala Gly Phe Glu Thr Pro Thr Leu Leu Phe Ser Leu Asp
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
    50                  55                  60

Val Tyr Pro Thr Lys Thr Phe Pro Asn His Tyr Ser Ile Val Thr Gly
65                  70                  75                  80

Leu Tyr Pro Glu Ser His Gly Ile Ile Asp Asn Lys Met Tyr Asp Pro
                85                  90                  95

Lys Met Asn Ala Ser Phe Ser Leu Lys Ser Lys Glu Lys Phe Asn Pro
            100                 105                 110

Glu Trp Tyr Lys Gly Glu Pro Ile Trp Val Thr Ala Lys Tyr Gln Gly
        115                 120                 125

Leu Lys Ser Gly Thr Phe Phe Trp Pro Gly Ser Asp Val Glu Ile Asn
    130                 135                 140

Gly Ile Phe Pro Asp Ile Tyr Lys Met Tyr Asn Gly Ser Val Pro Phe
145                 150                 155                 160

Glu Glu Arg Ile Leu Ala Val Leu Gln Trp Leu Gln Leu Pro Lys Asp
                165                 170                 175

Glu Arg Pro His Phe Tyr Thr Leu Tyr Leu Glu Glu Pro Asp Ser Ser
            180                 185                 190

Gly His Ser Tyr Gly Pro Val Ser Ser Glu Val Ile Lys Ala Leu Gln
        195                 200                 205
```

-continued

Arg Val Asp Gly Met Val Gly Met Leu Met Asp Gly Leu Lys Glu Leu
    210                 215                 220

Asn Leu His Arg Cys Leu Asn Leu Ile Leu Ile Ser Asp His Gly Met
225                 230                 235                 240

Glu Gln Gly Ser Cys Lys Lys Tyr Ile Tyr Leu Asn Lys Tyr Leu Gly
                245                 250                 255

Asp Val Lys Asn Ile Lys Val Ile Tyr Gly Pro Ala Ala Arg Leu Arg
                260                 265                 270

Pro Ser Asp Val Pro Asp Lys Tyr Tyr Ser Phe Asn Tyr Glu Gly Ile
            275                 280                 285

Ala Arg Asn Leu Ser Cys Arg Glu Pro Asn Gln His Phe Lys Pro Tyr
        290                 295                 300

Leu Lys His Phe Leu Pro Lys Arg Leu His Phe Ala Lys Ser Asp Arg
305                 310                 315                 320

Ile Glu Pro Leu Thr Phe Tyr Leu Asp Pro Gln Trp Gln Leu Ala Leu
                325                 330                 335

Asn Pro Ser Glu Arg Lys Tyr Cys Gly Ser Gly Phe His Gly Ser Asp
            340                 345                 350

Asn Val Phe Ser Asn Met Gln Ala Leu Phe Val Gly Tyr Gly Pro Gly
        355                 360                 365

Phe Lys His Gly Ile Glu Ala Asp Thr Phe Glu Asn Ile Glu Val Tyr
    370                 375                 380

Asn Leu Met Cys Asp Leu Leu Asn Leu Thr Pro Ala Pro Asn Asn Gly
385                 390                 395                 400

Thr His Gly Ser Leu Asn His Leu Leu Lys Asn Pro Val Tyr Thr Pro
                405                 410                 415

Lys His Pro Lys Glu Val His Pro Leu Val Gln Cys Pro Phe Thr Arg
            420                 425                 430

Asn Pro Arg Asp Asn Leu Gly Cys Ser Cys Asn Pro Ser Ile Leu Pro
        435                 440                 445

Ile Glu Asp Phe Gln Thr Gln Phe Asn Leu Thr Val Ala Glu Glu Lys
    450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
            500                 505                 510

Arg Asn Asp Ser Phe Ser Thr Glu Asp Phe Ser Asn Cys Leu Tyr Gln
        515                 520                 525

Asp Phe Arg Ile Pro Leu Ser Pro Val His Lys Cys Ser Phe Tyr Lys
    530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
            580                 585                 590

Thr Leu Leu Arg Lys Tyr Ala Glu Glu Arg Asn Gly Val Asn Val Val
        595                 600                 605

Ser Gly Pro Val Phe Asp Phe Asp Tyr Asp Gly Arg Cys Asp Ser Leu
    610                 615                 620

Glu Asn Leu Arg Gln Lys Arg Arg Val Ile Arg Asn Gln Glu Ile Leu

```
            625                 630                 635                 640
Ile Pro Thr His Phe Phe Ile Val Leu Thr Ser Cys Lys Asp Thr Ser
                    645                 650                 655

Gln Thr Pro Leu His Cys Glu Asn Leu Asp Thr Leu Ala Phe Ile Leu
                660                 665                 670

Pro His Arg Thr Asp Asn Ser Glu Ser Cys Val His Gly Lys His Asp
            675                 680                 685

Ser Ser Trp Val Glu Glu Leu Leu Met Leu His Arg Ala Arg Ile Thr
        690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                    725                 730                 735

Gln Glu Asp Glu Pro Lys Ser Cys Asp Lys Thr His Thr Cys Pro Pro
                740                 745                 750

Cys Pro Ala Pro Glu Leu Leu Gly Gly Pro Ser Val Phe Leu Phe Pro
            755                 760                 765

Pro Lys Pro Lys Asp Thr Leu Met Ile Ser Arg Thr Pro Glu Val Thr
        770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                    805                 810                 815

Glu Glu Gln Tyr Asn Ser Thr Tyr Arg Val Val Ser Val Leu Thr Val
                820                 825                 830

Leu His Gln Asp Trp Leu Asn Gly Lys Glu Tyr Lys Cys Lys Val Ser
            835                 840                 845

Asn Lys Ala Leu Pro Ala Pro Ile Glu Lys Thr Ile Ser Lys Ala Lys
        850                 855                 860

Gly Gln Pro Arg Glu Pro Gln Val Tyr Thr Leu Pro Pro Ser Arg Glu
865                 870                 875                 880

Glu Met Thr Lys Asn Gln Val Ser Leu Thr Cys Leu Val Lys Gly Phe
                    885                 890                 895

Tyr Pro Ser Asp Ile Ala Val Glu Trp Glu Ser Asn Gly Gln Pro Glu
                900                 905                 910

Asn Asn Tyr Lys Thr Thr Pro Pro Val Leu Asp Ser Asp Gly Ser Phe
            915                 920                 925

Phe Leu Tyr Ser Lys Leu Thr Val Asp Lys Ser Arg Trp Gln Gln Gly
        930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                    965                 970

<210> SEQ ID NO 12
<211> LENGTH: 966
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Lys Ser Trp Val Glu Glu Pro Cys Glu Ser Ile Asn Glu Pro Gln
1               5                   10                  15
```

```
Cys Pro Ala Gly Phe Glu Thr Pro Thr Leu Leu Phe Ser Leu Asp
             20              25              30

Gly Phe Arg Ala Glu Tyr Leu His Thr Trp Gly Gly Leu Leu Pro Val
         35              40              45

Ile Ser Lys Leu Lys Lys Cys Gly Thr Tyr Thr Lys Asn Met Arg Pro
50              55              60

Val Tyr Pro Thr Lys Thr Phe Pro Asn His Tyr Ser Ile Val Thr Gly
65              70              75              80

Leu Tyr Pro Glu Ser His Gly Ile Ile Asp Asn Lys Met Tyr Asp Pro
             85              90              95

Lys Met Asn Ala Ser Phe Ser Leu Lys Ser Lys Glu Lys Phe Asn Pro
             100             105             110

Glu Trp Tyr Lys Gly Glu Pro Ile Trp Val Thr Ala Lys Tyr Gln Gly
             115             120             125

Leu Lys Ser Gly Thr Phe Phe Trp Pro Gly Ser Asp Val Glu Ile Asn
130             135             140

Gly Ile Phe Pro Asp Ile Tyr Lys Met Tyr Asn Gly Ser Val Pro Phe
145             150             155             160

Glu Glu Arg Ile Leu Ala Val Leu Gln Trp Leu Gln Leu Pro Lys Asp
             165             170             175

Glu Arg Pro His Phe Tyr Thr Leu Tyr Leu Glu Glu Pro Asp Ser Ser
             180             185             190

Gly His Ser Tyr Gly Pro Val Ser Ser Glu Val Ile Lys Ala Leu Gln
             195             200             205

Arg Val Asp Gly Met Val Gly Met Leu Met Asp Gly Leu Lys Glu Leu
210             215             220

Asn Leu His Arg Cys Leu Asn Leu Ile Leu Ile Ser Asp His Gly Met
225             230             235             240

Glu Gln Gly Ser Cys Lys Lys Tyr Ile Tyr Leu Asn Lys Tyr Leu Gly
             245             250             255

Asp Val Lys Asn Ile Lys Val Ile Tyr Gly Pro Ala Ala Arg Leu Arg
             260             265             270

Pro Ser Asp Val Pro Asp Lys Tyr Tyr Ser Phe Asn Tyr Glu Gly Ile
             275             280             285

Ala Arg Asn Leu Ser Cys Arg Glu Pro Asn Gln His Phe Lys Pro Tyr
             290             295             300

Leu Lys His Phe Leu Pro Lys Arg Leu His Phe Ala Lys Ser Asp Arg
305             310             315             320

Ile Glu Pro Leu Thr Phe Tyr Leu Asp Pro Gln Trp Gln Leu Ala Leu
             325             330             335

Asn Pro Ser Glu Arg Lys Tyr Cys Gly Ser Gly Phe His Gly Ser Asp
             340             345             350

Asn Val Phe Ser Asn Met Gln Ala Leu Phe Val Gly Tyr Gly Pro Gly
             355             360             365

Phe Lys His Gly Ile Glu Ala Asp Thr Phe Glu Asn Ile Glu Val Tyr
             370             375             380

Asn Leu Met Cys Asp Leu Leu Asn Leu Thr Pro Ala Pro Asn Asn Gly
385             390             395             400

Thr His Gly Ser Leu Asn His Leu Leu Lys Asn Pro Val Tyr Thr Pro
             405             410             415

Lys His Pro Lys Glu Val His Pro Leu Val Gln Cys Pro Phe Thr Arg
             420             425             430
```

```
Asn Pro Arg Asp Asn Leu Gly Cys Ser Cys Asn Pro Ser Ile Leu Pro
            435                 440                 445

Ile Glu Asp Phe Gln Thr Gln Phe Asn Leu Thr Val Ala Glu Glu Lys
450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
                500                 505                 510

Arg Asn Asp Ser Phe Ser Thr Glu Asp Phe Ser Asn Cys Leu Tyr Gln
                515                 520                 525

Asp Phe Arg Ile Pro Leu Ser Pro Val His Lys Cys Ser Phe Tyr Lys
            530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
            580                 585                 590

Thr Leu Leu Arg Lys Tyr Ala Glu Glu Arg Asn Gly Val Asn Val Val
        595                 600                 605

Ser Gly Pro Val Phe Asp Phe Asp Tyr Asp Gly Arg Cys Asp Ser Leu
    610                 615                 620

Glu Asn Leu Arg Gln Lys Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Glu Leu Leu Met Leu His Arg Ala Arg Ile Thr
    690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp Asp Lys Thr His Thr Cys Pro Pro Cys Pro Ala Pro Glu
            740                 745                 750

Leu Leu Gly Gly Pro Ser Val Phe Leu Phe Pro Pro Lys Pro Lys Asp
        755                 760                 765

Thr Leu Met Ile Ser Arg Thr Pro Glu Val Thr Cys Val Val Val Asp
770                 775                 780

Val Ser His Glu Asp Pro Glu Val Lys Phe Asn Trp Tyr Val Asp Gly
785                 790                 795                 800

Val Glu Val His Asn Ala Lys Thr Lys Pro Arg Glu Glu Gln Tyr Asn
                805                 810                 815

Ser Thr Tyr Arg Val Val Ser Val Leu Thr Val Leu His Gln Asp Trp
            820                 825                 830

Leu Asn Gly Lys Glu Tyr Lys Cys Lys Val Ser Asn Lys Ala Leu Pro
        835                 840                 845

Ala Pro Ile Glu Lys Thr Ile Ser Lys Ala Lys Gly Gln Pro Arg Glu
```

```
                850                 855                 860
Pro Gln Val Tyr Thr Leu Pro Pro Ser Arg Glu Glu Met Thr Lys Asn
865                 870                 875                 880

Gln Val Ser Leu Thr Cys Leu Val Lys Gly Phe Tyr Pro Ser Asp Ile
                885                 890                 895

Ala Val Glu Trp Glu Ser Asn Gly Gln Pro Glu Asn Asn Tyr Lys Thr
            900                 905                 910

Thr Pro Pro Val Leu Asp Ser Asp Gly Ser Phe Phe Leu Tyr Ser Lys
        915                 920                 925

Leu Thr Val Asp Lys Ser Arg Trp Gln Gln Gly Asn Val Phe Ser Cys
    930                 935                 940

Ser Val Met His Glu Ala Leu His Asn His Tyr Thr Gln Lys Ser Leu
945                 950                 955                 960

Ser Leu Ser Pro Gly Lys
                965

<210> SEQ ID NO 13
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Glu Pro Lys Ser Cys Asp Lys Thr His Thr Cys Pro Pro Cys Pro
1               5                   10                  15

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Lys Thr His Thr Cys Pro Pro Cys Pro
1               5                   10

<210> SEQ ID NO 15
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Pro Lys Ser Cys Asp Lys Thr His Thr Cys Pro Pro Cys Pro
1               5                   10

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16
```

Gly Gly Gly Gly Ser Gly Gly Gly Gly Ser Gly Gly Gly Gly Ser
1               5                   10                  15

<210> SEQ ID NO 17
<211> LENGTH: 6
<212> TYPE: PRT
<213> ORGANISM: Homo sapiens

<400> SEQUENCE: 17

Pro Ser Cys Ala Lys Glu
1               5

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Asp Asp Asp Asp Asp Asp Asp Asp Asp
1               5                   10

<210> SEQ ID NO 19
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(50)
<223> OTHER INFORMATION: /note="This sequence may encompass 1-10 "Gly
      Gly Gly Gly Ser" repeating units"

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Asp Asp Asp Asp Asp Asp Asp Asp
1               5

<210> SEQ ID NO 21
<211> LENGTH: 8
<212> TYPE: PRT
<213> ORGANISM: Artificial Sequence

```
-continued

<220> FEATURE:
<221> NAME/KEY: source
<223> OTHER INFORMATION: /note="Description of Artificial Sequence:
      Synthetic peptide"

<400> SEQUENCE: 21

Glu Glu Glu Glu Glu Glu Glu Glu
1               5
```

METHODS OF TREATING MYOINTIMAL PROLIFERATION

RELATED APPLICATIONS

This application is a 35 U.S.C. 371 national stage filing of International Application No. PCT/US2017/037695, filed on Jun. 15, 2017, which claims the benefit of U.S. Provisional Application No. 62/350,936, filed on Jun. 16, 2016. The contents of any patents, patent applications, and references cited throughout this specification are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 11, 2018, is named txt AXJ_211_US_SEQ.txt and is 89,326 bytes in size.

BACKGROUND

Myointimal proliferation (also known as myointimal hyperplasia) is an arterial wall smooth muscle cell (SMC) proliferative disorder (Painter, T A, *Artif. Organs*. 1991 February; 15(1):42-55). Specifically, myointimal proliferation involves the migration and proliferation of vascular smooth muscle cells (VSMCs), as well as the involvement of the extracellular matrix in the intima i.e., the innermost coat of a blood vessel consisting of an endothelial layer backed by connective tissue and elastic tissue (see, e.g., Kraiss L W, Clowes A W, In: Sumpio SAN, ed. *The Basic Science of Vascular Disease*. New York, N.Y.: Futura Publishing; 1997:289-317; and Yang Z, Luscher T F. *Eur Heart J*. 1993; 14(suppl):193-197).

Ectonucleotide pyrophosphatase pyrophosphorylase 1 (NPP1) is an ectoenzyme that cleaves ATP to produce extracellular pyrophosphate (PPi). Ectonucleotide pyrophosphatase/phosphodiesterase 1 (NPP1/ENPP1/PC-1) deficiency is a rare disease caused by mutations in NPP1, a type II transmembrane glycoprotein. NPP1 cleaves a variety of substrates, including phosphodiester bonds of nucleotides and nucleotide sugars and pyrophosphate bonds of nucleotides and nucleotide sugars. NPP1 deficiency has been associated with idiopathic infantile arterial calcification (IIAC), insulin resistance, hypophosphatemic rickets, and ossification of the posterior longitudinal ligament of the spine. IIAC, a rare autosomal recessive and nearly always fatal disorder, is characterized by calcification of the internal elastic lamina of muscular arteries and stenosis due to myointimal proliferation. There are more than 160 cases of IIAC that have been reported world-wide. The symptoms of the disease most often appear by early infancy, and the disease is lethal by 6 months of age, generally because of ischemic cardiomyopathy, and other complications of obstructive arteriopathy including renal artery stenosis.

Although defects in the NPP1 protein have been implicated in such serious disease as IIAC, currently no treatment is available for those who are affected by the disease. Current therapeutic options have limited efficacy and undesirable and/or unacceptable side effects. Braddock, D. et al., (WO 2014/126965A2) discloses compositions and methods for treating pathological calcification and ossification by administering NPP1. Quinn, A. et al., (WO 2012/125182A1) discloses a NPP1 fusion protein to treat conditions including Generalized Arterial Calcification of Infancy (GACI), arterial calcification, insulin resistance, hypophasphatemic rickets, and ossificaiton of the posterior longitudinal ligament of the spine.

In spite of considerable research in the field, there is a continuing need for new therapies to effectively treat NPP1-deficiencies, including myointimal proliferation disorders

SUMMARY OF THE INVENTION

The present invention relates to uses of isolated recombinant human soluble NPP1 that lacks N-terminal cytosolic and transmembrane domains and fusion proteins thereof for the treatment of NPP1-deficiency and/or myointimal proliferation disorders. Any disorder that is characterized by myointimal proliferation is within the scope of the present invention.

In one aspect, methods for treating a human patient having detected myointimal proliferation (e.g., as assessed by immunohistochemical detection, ultrasound (e.g., intravascular ultrasonography, carotid ultrasound, or contrast-enhanced ultrasound (CEU)), X-ray computed tomography (CT), nuclear imaging (e.g., positron emission tomography (PET) or single-photon emission computed tomography (SPECT)), optical imaging, or contrast enhanced image) are provided, the method comprising administering to the patient one or more doses of a recombinant human soluble ectonucleotide pyrophosphatase phosphodiesterase (hsNPP1), active fragment or fusion protein thereof.

In another aspect, the methods of treating myointimal proliferation (e.g., as assessed by immunohistochemical detection) in a human patient, are provided, the method comprising: a) identifying a human patient as having myointimal proliferation and b) administering to the identified patient one or more doses of a recombinant human soluble ectonucleotide pyrophosphatase phosphodiesterase (hsNPP1), active fragment or fusion protein thereof.

In one embodiment, a NPP1 fusion protein is administered. Preferred fusion proteins comprise and NPP1 component an Fc region of an immunoglobulin and, optionally, a targeting moiety. In one embodiment, the targeting moiety is $Asp_{10}$ (SEQ ID NO: 18). In another embodiment, the targeting moiety comprises at least eight consecutive aspartic acid or glutamic acid residues (SEQ ID NOS 20 and 21, respectively). Particular NPP1 fusion proteins for administration in accordance with the methods disclosed herein have the amino acid sequence set forth in SEQ ID NO:3, SEQ ID NO:4, SEQ ID NO:9, SEQ ID NO:10, SEQ ID NO:11 or SEQ ID NO:12.

In another embodiment, the human patient has an NPP1 deficiency resulting in insufficient production of adenosine or adenosine monophosphate (AMP). In another embodiment, administration of a recombinant hsNPP1 according to the methods described herein is sufficient to normalize adenosine or adenosine monophosphate (AMP) production in the human patient. In another embodiment, administration of a recombinant hsNPP1 according to the methods described herein is sufficient to prevent arterial stenosis in the patient.

Any suitable amount of the recombinant hsNPP1 can be administered to the human patient. In one embodiment, the hsNPP1 is administered in one or more doses containing about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, or 20.0 mg/kg. In another embodiment, the hsNPP1 is administered in one or more doses containing about 1.0 mg/kg to about 5.0 mg/kg NPP1. In another embodiment, the hsNPP1 is administered in one or more doses containing about 1.0 mg/kg to about 10.0 mg/kg NPP1.

The time period between doses of the hsNPP1 is at least 2 days and can be longer, for example at least 3 days, at least 1 week, 2 weeks or 1 month. In one embodiment, the administration is weekly, bi-weekly, or monthly.

The recombinant hsNPP1 can be administered in any suitable way, such as intravenously, subcutaneously, or intraperitoneally.

The recombinant hsNPP1 can be administered in combination with one or more additional therapeutic agents. Exemplary therapeutic agents include, but are not limited to Bisphosphonate, Statins, Fibrates, Niacin, Aspirin, Clopidogrel, and varfarin. In one embodiment, the recombinant hsNPP1 and additional therapeutic agent are administered separately and are administered concurrently or sequentially. In one embodiment, the recombinant hsNPP1 is administered prior to administration of the additional therapeutic agent. In another embodiment, the recombinant hsNPP1 is administered after administration of the additional therapeutic agent. In another embodiment, the recombinant hsNPP1 and additional therapeutic agent are administered together.

In one embodiment, the patient does not have arterial calcification. In one another, the patient does have arterial calcification.

In another aspect uses of an isolated recombinant human sNPP1, fragment or fusion protein thereof are provided. In one embodiment, the use of an isolated recombinant human sNPP1, fragment or fusion protein thereof for the manufacture of a medicament for treating myointimal proliferation is provided. In another embodiment, the invention provides the use of an isolated recombinant human sNPP1, fragment or fusion protein thereof for treating myointimal proliferation. In one embodiment, the myointimal proliferation is not associated with arterial calcification. In another embodiment, the myointimal proliferation is associated with arterial calcification.

Other features and advantages of the invention will be apparent from the following detailed description and claims.

BRIEF DESCRIPTION OF THE DRAWINGS

FIG. 2A depicts inhibition of ENPP1 mRNA expression relative to a negative control for five siRNA constructs, 48 hours post siRNA transfection. FIG. 2B depicts inhibition of ENPP1 mRNA expression relative to a negative control six and eleven days post siRNA transfection with construct #4.

FIG. 8A depicts the effect of silencing ENPP1 by two siRNA on proliferation of rat VSMCs. FIG. 8B depicts inhibition of ENPP1 mRNA expression relative to a negative control for two siRNA constructs, 48 hours post siRNA transfection.

FIGS. 13A-13B shows that silencing ENPP1 increases proliferation on rat VSMCs and overexpression of mouse or rat ENPP1 inhibits proliferation on rat VSMCs that either downregulated ENPP1 expression (si-rENPP1) or normal ENPP1 expression (si-NC).

FIGS. 18A-18B shows that heat denatured human/mouse ENPP1-Fc protein completely lost their enzymatic activity.

FIGS. 19A-19C depicts the effect of murine ENPP1-Fc protein (FIG. 19A), human ENPP1-Fc (FIG. 19B) and human ENPP1-FC-D10 (FIG. 19C) on proliferation of rat primary VSMCs.

FIGS. 27A-27C are a morphometric quantitation of medial (FIG. 27A) and intimal areas (FIG. 27B), as well as the I/M ratio (FIG. 27C). *p<0.001.

FIG. 28A shows the degree of intimal hyperplasia 7 days post ligation in WT and ttw/ttw mice. FIG. 28B shows the histological analysis (Von Gieson's stain) of sections either 100 (upper) or 200 (lower) μm from point of ligation from WT, vehicle-treated ttw/ttw or rhENPP1-treated ttw/ttw mice from left to right, respectively. The internal elastic lamina (IEL), external elastic lamina (EEL) and lumen (L) are indicated by arrows. The scale bar represents 100 μm.

FIGS. 29A-29C are a morphometric quantitations of medial (FIG. 29A) and intimal areas (FIG. 29B), as well as the I/M ratio (FIG. 29C) on treatment day 14. *p<0.05, **p<0.01.

DETAILED DESCRIPTION

Definitions

Figure 1A:
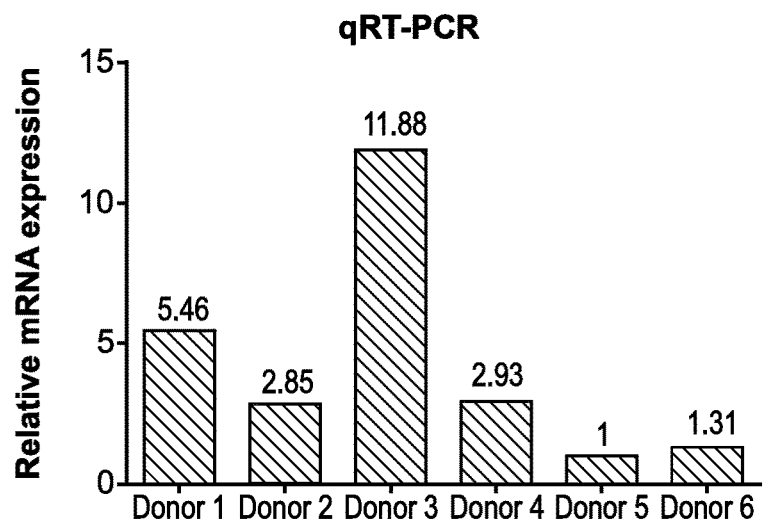
FIGS. 1A-1C depict mRNA (FIG. 1A) and protein (FIG. 1B) ENPP1 expression in human primary VSMCs from six different donors, as well as enzyme activity from three of the donors (FIG. 1C).

Unless defined otherwise, all technical and scientific terms used herein have the same meaning as commonly understood by one of ordinary skill in the art to which this invention belongs. Although any methods and materials similar or equivalent to those described herein can be used in practice or testing of the present invention, the preferred methods and materials are described.

For clarity, "NPP1" and "ENPP1" refer to the same protein and are used interchangeably herein.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "fragment", with regard to NPP1 proteins, refers to an active subsequence of the full-length NPP1. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between). The fragments may range in size from four amino acid residues to the entire amino acid sequence minus one amino acid. Thus, a protein "comprising at least a portion of the amino acid sequence of SEQ ID NO: 1" encompasses the full-length NPP1 and fragments thereof.

An "isolated" or "purified" soluble NPP1 protein or biologically active fragment or fusion protein thereof is substantially free of cellular material or other contaminating proteins from the cell or tissue source from which the NPP1 protein, biologically active fragment or NPP1 fusion protein is derived, or substantially free from chemical precursors or other chemicals when chemically synthesized. The language "substantially free of cellular material" includes preparations of NPP1 protein, biologically active fragment, or NPP1 fusion protein in which the protein is separated from cellular components of the cells from which it is isolated or recombinantly produced. In one embodiment, the language "substantially free of cellular material" includes preparations of NPP1 protein, biologically active fragment or NPP1 fusion protein having less than about 30% (by dry weight) of non-NPP1 protein/fragment/fusion protein (also referred to herein as a "contaminating protein"), more preferably less than about 20% of non-NPP1 protein/fragment/fusion protein, still more preferably less than about 10% of non-NPP1 protein/fragment/fusion protein, and most preferably less than about 5% non-NPP1 protein/fragment/fusion protein. When the NPP1 protein, fusion protein, or biologically active fragment thereof is recombinantly produced, it is also preferably substantially free of culture medium, i.e., culture medium represents less than about 20%, more preferably less than about 10%, and most preferably less than about 5% of the volume of the protein preparation.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "subject" encompasses mammals and non-mammals. Examples of mammals include, but are not limited to, humans, chimpanzees, apes monkeys, cattle, horses, sheep, goats, swine, rabbits, dogs, cats, rats, mice, guinea pigs, and the like. Examples of non-mammals include, but are not limited to, birds, fish and the like.

As used herein, the term "therapeutically effective amount" refers to a nontoxic but sufficient amount of an agent (e.g., hsNPP1 proteins) which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "myointimal proliferation" (also referred to as "myointimal hyperplasia") refers to abnormal proliferation of the smooth muscle cells of the vascular wall (e.g., the intima of a blood vessel).

The term "treating" includes the application or administration of the NPP1 proteins, active fragments and fusion proteins of the invention to a subject, or application or administration of NPP1 proteins, active fragments and fusion proteins of the invention to a subject who has myointimal proliferation, with the purpose of curing, healing, alleviating, relieving, altering, remedying, ameliorating, preventing, improving, or affecting the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; or improving a subject's physical or mental well-being. Treatment may be therapeutic or prophylactic. The treatment or amelioration of symptoms can be based on objective or subjective parameters; including the results of a physical examination.

Methods of Treatment

The present invention relates to uses of an isolated recombinant human soluble NPP1 ("sNPP1") which lacks an N-terminal portion (i.e., lacking cytosolic and transmembrane domains) and fusion proteins thereof for the treatment of NPP1-associated diseases, such as myointimal proliferation.

The subject can be a human patient having deficiencies in NPP1 activity (NPP1 deficiency). In one embodiment, the patient exhibits low levels of pyrophosphate and/or suffers from a disease or disorder associated with low levels of pyrophosphate. In another embodiment, the human patient has an NPP1 deficiency resulting in insufficient production of adenosine or adenosine monophosphate (AMP).

Generally, the dosage of fusion protein administered to a subject will vary depending upon known factors such as age, health and weight of the recipient, type of concurrent treatment, frequency of treatment, and the like. Usually, a dosage of active ingredient (i.e., fusion protein) can be between about 0.0001 and about 50 milligrams per kilogram of body weight. Precise dosage, frequency of administration and time span of treatment can be determined by a physician skilled in the art of administration of therapeutic proteins.

A preferred embodiment of the present invention involves a method of treating myointimal proliferation, which includes the step of identifying a human patient as having myointimal proliferation and administering to the identified patient a therapeutically effective amount of a recombinant human soluble ectonucleotide pyrophosphatase phosphodiesterase (hsNPP1), active fragment or fusion protein thereof.

As defined herein, a therapeutically effective amount of protein (i.e., an effective dosage) ranges from about 0.001 to 50 mg/kg body weight. The skilled artisan will appreciate that certain factors may influence the dosage required to effectively treat a subject, including but not limited to the severity of the disease, previous treatments, the general health and/or age of the subject, and other diseases present. Moreover, treatment of a subject with a therapeutically effective amount of protein can include a single treatment or, preferably, can include a series of treatments. It will also be appreciated that the effective dosage of protein used for treatment may increase or decrease over the course of a particular treatment.

As defined herein, a therapeutically effective amount of protein or polypeptide (i.e., an effective dosage) ranges from about 0.001 to 50 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. In one embodiment, the hsNPP1 is administered in one or more doses containing about 0.1 mg/kg, 0.2 mg/kg, 0.3 mg/kg, 0.4 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, 20.0 mg/kg, 21.0 mg/kg, 22.0 mg/kg, 23.0 mg/kg, 24.0 mg/kg, 25.0 mg/kg, 26.0 mg/kg, 27.0 mg/kg, 28.0 mg/kg, 29.0 mg/kg, 30.0 mg/kg, 31.0 mg/kg, 32.0 mg/kg, 33.0 mg/kg, 34.0 mg/kg, 35.0 mg/kg, 36.0 mg/kg, 37.0 mg/kg, 38.0 mg/kg, 39.0 mg/kg, 40.0 mg/kg, 41.0 mg/kg, 42.0 mg/kg, 43.0 mg/kg, 44.0 mg/kg, or 45.0 mg/kg. In another embodiment, about 0.5 to about 30 mg, about 0.5 to about 20 mg, about 0.5 to about 10 mg, or about 0.5 to about 5 mg are administered to the patient. In another embodiment, the hsNPP1 is administered in one or more doses containing about 1.0 mg/kg to about 5.0 mg/kg hsNPP1. In another embodiment, the hsNPP1 is administered in one or more doses containing about 1.0 mg/kg to about 10.0 mg/kg hsNPP1. The skilled artisan will appreciate that certain factors may influence the dosage required to effectively treat a subject, including, but not limited to, the severity of the disease or disorder, previous treatments, the general health and/or age of the subject, and other diseases present.

Moreover, treatment of a subject with a therapeutically effective amount of a protein, polypeptide, or antibody can include a single treatment or, preferably, can include a series of treatments. In one embodiment, in the range of between about 0.1 to 20 mg/kg body weight, one time per week, twice per week, once in about 10 days, once in about 12 days, once in about 14 days, once in about 17 days, once in about 20 days, once in about about 25 days, or once in about 30 days. In one embodiment, the time period between doses of the hsNPP1 is at least 2 days and can be longer, for example at least 3 days, at least 1 week, 2 weeks or 1 month. In another embodiment, the therapeutically effective dose of sNPP1, biologically active fragment or fusion protein thereof is administered to a patient between one time every 5 days and one time every 30 days for a period of time determined by a practitioner of skill in the art of medical sciences. In another embodiment, the period of time will be the remainder of the patient's life span. In another embodiment, the dosing frequency is between one time every 5 days and one time every 25 days. In another embodiment, the dosing frequency is between one time every 5 days and one time every 21 days. In another embodiment, the dosing frequency is between one time every 7 days and one time every 14 days. hsNPP1, biologically active fragment or fusion protein thereof can be administered one time every 5 days, one time every 6 days, one time every 7 days, one time every 8 days, one time every 9 days, one time every 10 days, one time every 11 days, one time every 12 days, one time every 13 days, or one time every 14 days. In some embodiments, hsNPP1, biologically active fragment or fusion protein thereof is administered about weekly. In other embodiments, sNPP1, biologically active fragment or fusion protein thereof is administered about bi-weekly. In one embodiment, the dosing frequency is one time about 30 days. It will also be appreciated that the effective dosage of soluble sNPP1 protein, biologically active fragment or fusion protein thereof used for the treatment may increase or decrease over the course of a particular treatment.

In one embodiment, about 1 mg/kg of hsNPP1, biologically active fragment or fusion protein is administered to the patient once a week. In one embodiment, about 2 mg/kg of hsNPP1, biologically active fragment or fusion protein is administered to the patient once a week. In one embodiment, about 3 mg/kg of hsNPP1, biologically active fragment or fusion protein is administered to the patient once a week. In one embodiment, about 4 mg/kg of sNPP1, biologically active fragment or fusion protein is administered to the patient once a week. In one embodiment, about 5 mg/kg of hsNPP1, biologically active fragment or fusion protein is administered to the patient once a week. In one embodiment, about 6 mg/kg of hsNPP1, biologically active fragment or fusion protein is administered to the patient once a week. In one embodiment, about 7 mg/kg of hsNPP1, biologically active fragment or fusion protein is administered to the patient once a week. In one embodiment, about 8 mg/kg of hsNPP1, biologically active fragment or fusion protein is administered to the patient once a week. In one embodiment, about 9 mg/kg of hsNPP1, biologically active fragment or fusion protein is administered to the patient once a week. In one embodiment, about 10 mg/kg of hsNPP1, biologically active fragment or fusion protein is administered to the patient once a week.

hsNPP1, biologically active fragment or fusion protein can be administered by, for example, subcutaneous injections, intramuscular injections, and intravenous (IV) infusions or injections.

In one embodiment, hsNPP1, biologically active fragment or fusion protein is administered intravenously by IV infusion by any useful method. In one example, hsNPP1, biologically active fragment or fusion protein can be administered by intravenous infusion through a peripheral line. In another example, hsNPP1, biologically active fragment or fusion protein can be administered by intravenous infusion through a peripherally inserted central catheter.

In another embodiment, hsNPP1, biologically active fragment or fusion protein is administered intravenously by IV injection.

In another embodiment, hsNPP1, biologically active fragment or fusion protein is administered via intraperitoneal injection.

In another embodiment, hsNPP1, biologically active fragment or fusion protein is administered by subcutaneous injections.

In another embodiment, hsNPP1, biologically active fragment or fusion protein is administered by intramuscular injections.

In still another embodiment, hsNPP1, biologically active fragment or fusion protein is administered via a pharmaceutically acceptable capsule of the therapeutic protein. For example, the capsule can be an enteric-coated gelatin capsule.

In one embodiment, the method involves administering the soluble NPP1 protein or NPP1 fusion protein of the invention alone, or in combination with other agent(s). Exemplary therapeutic agents include, but are not limited to bisphosphonate, Statins, Fibrates, Niacin, Aspirin, Clopidogrel, and varfarin. In one embodiment, the method involves administering an NPP1 protein or an NPP1 fusion protein of the invention as therapy to compensate for reduced or aberrant NPP1 expression or activity in the subject having an NPP1-deficiency or other associated disease or disorder. In one embodiment, the isolated sNPP1 proteins, fragments, and fusion proteins can be administered before, after or concurrently with the agent or can be co-administered with other known therapies. Co-administration of the isolated sNPP1 proteins, fragments, and fusion proteins of the present invention with other therapeutic agents may provide two agents which operate via different mechanisms which yield an increased therapeutic effect. Such co-administration can solve problems due to development of resistance to drugs. In particular aspects, this disclosure relates to a method for reducing myointimal proliferation in a subject in need thereof.

The methods described herein provide a way to reduce myointimal proliferation in a subject (e.g., human patient). In one embodiment, the human patient has an NPP1 deficiency resulting in insufficient production of adenosine or adenosine monophosphate (AMP). In another embodiment, administration of a recombinant hsNPP1 according to the methods described herein is sufficient to normalize adenosine or adenosine monophosphate (AMP) production in the human patient. In another embodiment, administration of a recombinant hsNPP1 according to the methods described herein is sufficient to prevent arterial stenosis in the patient.

sNPP1

The present invention employs soluble NPP1 (e.g., hsNPP1) that has a biologically active NPP1 domain of NPP1 (i.e., NPP1 components that contain at least one extracellular catalytic domain of naturally occurring NPP1 for the pyrophosphatase and/or phosphodiesterase activity). The soluble NPP1 proteins of the invention comprise at least the NPP1 domain essential to carry out the pyrophosphatase and/or phosphodiesterase activity.

In one embodiment, the soluble NPP1, fragment, and fusion proteins thereof can form functional homodimers or monomer. In another embodiment, a soluble NPP1 protein or NPP1 fusion protein thereof can be assayed for pyrophosphatase activity as well as the ability to increase pyrophosphate levels in vivo.

Described herein are various amino acid sequences of soluble NPP1 compounds, fusion partners and fusion proteins that are suitable for use according to the methods provided herein. SEQ ID NO:5 shows the amino acid sequences of a soluble NPP1 containing amino acids from 107 to 925 of SEQ ID NO:1. SEQ ID NO:6 shows the amino acid sequence of a soluble NPP1 containing amino acids from 187 to 925 of SEQ ID NO:1. SEQ ID NO:7 shows the amino acid sequence of the Fc region of human IgG1 including the hinge region. SEQ ID NO:8 shows the amino acid sequence of the Fc of human IgG1 including a partial hinge region. SEQ ID NO:9 shows the amino acid sequence of a NPP1-Fc fusion protein. The NPP1 component contains SEQ ID NO:5, and the Fc sequence includes the hinge region. SEQ ID NO:10 shows the amino acid sequence of a NPP1-Fc fusion protein. The soluble NPP1 contains SEQ ID NO:5, and the Fc sequence includes the partial hinge region. SEQ ID NO:1 shows the amino acid sequence of a NPP1-Fc fusion protein. The soluble NPP1 contains SEQ ID NO:6, and the Fc sequence includes the hinge region. SEQ ID NO:12 shows the amino acid sequence of a NPP1-Fc fusion protein. The soluble NPP1 contains SEQ ID NO:6, and the Fc sequence includes the partial hinge region.

Preferred soluble NPP1 proteins and NPP1 fusion proteins of the invention are enzymatically active in vivo (e.g., human). In one embodiment, the soluble protein comprises amino acid sequence having at least 60, 70, 75, 80, 85, 90, 91, 92, 93, 94, 95, 96, 97, 98, 99% sequence identity to the following sequence:

```
                                           (SEQ ID NO: 2)
PSCAKEVKSCKGRCFERTFGNCRCDAACVELGNCCLDYQETCIE

PEHIWTCNKFRCGEKRLTRSLCACSDDCKDKGDCCINYSSVCQG

EKSWVEEPCESDMEPQCPAGFETPPTLLFSLDGFRAEYLHTWGG

LLPVISKLKKCGTYTKNMRPVYPTKTFPNHYSIVTGLYPESHGI

IDNKMYDPKMNASFSLKSKEKFNPEWYKGEPIWVTAKYQGLKSG

TFFWPGSDVEINGIFPDIYKMYNGSVPFEERILAVLQWLQLPKD

ERPHFYTLYLEEPDSSGHSYGPVSSEVIKALQRVDGMVGMLMDG

LKELNLHRCLNLILISDHGMEQGSCKKYIYLNKYLGDVKNIKVI

YGPAARLRPSDVPDKYYSFNYEGIARNLSCREPNQHFKPYLKHF

LPKRLHFAKSDRIEPLTFYLDPQWQLALNPSERKYCGSGFHGSD
```

-continued

```
NVFSNMQALFVGYGPGFKHGIEADTFENIEVYNLMCDLLNLTPA

PNNGTHGSLNHLLKNPVYTPKHPKEVHPLVQCPFTRNPRDNLGC

SCNPSILPIEDFQTQFNLTVAEEKIIKHETLPYGRPRVLQKENT

ICLLSQHQFMSGYSQDILMPLWTSYTVDRNDSFSTEDFSNCLYQ

DFRIPLSPVHKCSFYKNNTKVSYGFLSPPQLNKNSSGIYSEALL

TTNIVPMYQSFQVIWRYFHDTLLRKYAEERNGVNVVSGPVFDFD

YDGRCDSLENLRQKRRVIRNQEILIPTHFFIVLTSCKDTSQTPL

HCENLDTLAFILPHRTDNSESCVHGKHDSSWVEELLMLHRARIT

DVEHITGLSFYQQRKEPVSDILKLKTHLPTFSQED
```

SEQ ID NO:2 is the amino acid sequence of a sNPP1 that contains the cysteine-rich region, catalytic region and c-terminal region.

Any desired enzymatically active form of soluble NPP1 can be used in the methods described herein. The enzymatically active sNPP1 can increase PPi levels in suitable enzymatic assays, and can be assayed for pyrophosphatase activity, phosphodiesterase activity, or pyrophosphatase and phosphodiesterase activity. Typically, the sNPP1 contains at least an NPP1 component that lacks the N-terminal cytosolic and transmembrane domains of naturally occurring transmembrane NPP1.

SEQ ID NO:1 is the amino acid sequence of wild-type NPP1 protein. The cytosolic and transmembrane regions are underlined. The potential N-glycosylation sites are in bold. The amino acid motif "PSCAKE" (SEQ ID NO:17) in bold is the start of a soluble NPP1 which includes the cysteine rich region.

In preferred aspects, the NPP1 component contains the cysteine-rich region (amino acids 99-204 of SEQ ID NO:1) and the catalytic region (amino acids 205-591 of SEQ ID NO:1) of naturally occurring human NPP1. Typically, the NPP1 component also includes the C-terminal region (amino acids 592 to 925 of SEQ ID NO:1), and has the amino acid sequence of SEQ ID NO:2. However, the C-terminal region can be truncated if desired. Accordingly, preferred NPP1 components include the cysteine-rich region and catalytic region of human NPP1 (amino acids 99-591 of SEQ ID NO:1) or the cysteine-rich region, the catalytic region and the C-terminal region of human NPP1 (SEQ ID NO:2). Other preferred NPP1 components contain only a portion of the cysteine-rich domain and have the sequence of amino acids 107 to 925 of SEQ ID NO:1 or amino acids 187 to 925 of SEQ ID NO:1.

The cysteine rich region of NPP1 (i.e., amino acids 99 to 204 of SEQ ID NO: 1) can facilitate dimerization of the sNPP1. The sNPP1, including fusion proteins, can be in the form of a monomer of functional homodimer.

The amino acid sequence of the NPP1 component can be a variant of the naturally occurring NPP1 sequence, provided that the NPP1 component is enzymatically active. NPP1 variants are enzymatically active and have at least 80%, at least 85%, at least 90%, at least 95% and more preferably at least 96% amino acid sequence identity to the corresponding portion of human NPP1 (e.g., over the length of the cysteine-rich region, the catalytic region, the c-terminal region, the cysteine-rich region plus the catalytic region, the cystein-rich region plus the catalytic region plus the c-terminal region. Preferred NPP1 variants have at least 90%, preferably at least 95%, more preferably at least 97% amino acid sequence identity to (i) the amino acid sequence of residues 205-591 of SEQ ID NO: 1, (ii) the amino acid sequence of residues 99-591 of SEQ ID NO:1, (iii) the amino acid sequence of residues 99-925 of SEQ ID NO:1, (iv) the amino acid sequence of residues 107-925 of SEQ ID NO:1, or (v) the amino acid sequence of residues 187-925 of SEQ ID NO:1. Suitable positions for amino acid variation are well-known from NPP1 structural studies and analysis of disease-associated mutations in NPP1. For example, substitution of the following amino acids occurs in certain disease-associated mutations that reduce NPP1 enzymatic activity, and variations of the amino acids at these positions should be avoided: Ser216, Gly242, Pro250, Gly266, Pro305, Arg349, Tyr371, Arg456, Tyr471, His500, Ser504, Tyr513, Asp538, Tyr570, Lys579, Gly586; Tyr659, Glu668, Cys726, Arg774, His777, Asn792, Asp804, Arg821, Arg888, and Tyr901. (See, e.g., Jansen, S. et al., Structure 20:1948-1959 (2012)).

In one embodiment, the soluble NPP1 protein can be a fusion protein recombinantly fused or chemically bonded (e.g., covalent bond, ionic bond, hydrophobic bond and Van der Waals force) to a fusion partner. In another embodiment, the fusion protein has at least 70, 75, 80, 85, 90, 91, 92, 93, 94, 95, 96, 97, 98, or 99% sequence identity to SEQ ID NO: 3 or SEQ ID NO:4. SEQ ID NO:4 is the amino acid sequence of sNPP1-Fc-D10 (SEQ ID NO:4). The Fc sequence is underlined.

To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., sNPP1 amino acid sequence of SEQ ID NO:2; amino acids 107-925 of SEQ ID NO:1 or amino acids 187-925 of SEQ ID NO:1). The amino acid residues or nucleotides at corresponding amino acid positions are then compared. When a position in the first sequence is occupied by the same amino acid residue or nucleotide as the corresponding position in the second sequence, then the molecules are identical at that position (as used herein amino acid is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J Mol Biol* 1970, 48, 444-453) algorithm which has been incorporated into the GAP program in the GCG software package (available at www.gcg.com), using either a Blosum 62 matrix or a PAM250 matrix, and a gap weight of 16, 14, 12, 10, 8, 6, or 4 and a length weight of 1, 2, 3, 4, 5, or 6. In another embodiment, the percent identity between two amino acid is determined using the algorithm of E. Meyers and W. Miller (CABIOS, 1989, 4, 11-17) which has been incorporated into the ALIGN program (version 2.0 or 2.0U), using a PAM120 weight residue table, a gap length penalty of 12 and a gap penalty of 4.

The sNPP1 can consist of or consist essentially of an NPP1 component as described herein. Alternatively, the sNPP1 can be in the form of a fusion protein that contains an NPP1 component and one or more other polypeptides, referred to as fusion partners, optionally through a suitable linker in each instance, or in the form of a conjugate between an NPP1 component and another molecule (e.g., PEG). When the sNPP1 is in the form of a fusion protein, each fusion partner is preferably located c-terminally to the NPP1 component. Without wishing to be bound by any particular theory, it is believed that fusion proteins that contain an NPP1 component that contains the cysteine-rich region and catalytic region, and one or more fusion proteins that are located c-terminally to the NPP1 component, are preferred over other configurations of NPP1 fusion proteins because they can be expressed at sufficient levels and are sufficiently stable to be used as therapeutic proteins.

Any suitable fusion partner can be included in the fusion protein. Advantageously, a number of fusion partners are well-known in the art that can provide certain advantages, such as reduced aggregation and immunogenicity, increased the solubility, improved expression and/or stability, and improved pharmacokinetic and/or pharmacodynamics performance. See, e.g., Strohl, W. R. *BioDrugs* 29:215-239 (2015). For example, it is well-known that albumin, albumin fragments or albumin variants (e.g., human serum albumin and fragments or variants thereof) can be incorporated into fusion proteins and that such fusion proteins can be easily purified, stable and have an improved plasma half-life. Suitable albumin, albumin fragments and albumin variants that can be used in the sNPP1 fusion proteins are disclosed, for example in WO 2005/077042A2 and WO 03/076567A2, each of which is incorporated herein by reference in its entirety. Fusions to human transferrin are also known to improve half-life. See, e.g., Kim B J et al., *J Pharmacol Expr Ther* 334(3):682-692 (2010); and WO 2000/020746. Peptides that bind to albumin or transferrin, such as antibodies or antibody fragments, can also be used. See, e.g., EP 0486525 B1, U.S. Pat. No. 6,267,964 B1, WO 04/001064A2, WO 02/076489A1, WO 01/45746, WO 2006/004603, and WO 2008/028977. Similarly immunoglobulin Fc fusion proteins are well-known. See, e.g., Czajkowsky D M et al., *EMBO Mol Med* 4(10):1015-1028 (2012), U.S. Pat. Nos. 7,902,151; and 7,858,297, the entire teachings of which are incorporated herein by reference in their entirety. The fusion protein can also include a CTP sequence (see also, Fares et al., *Endocrinol* 2010, 151, 4410-4417; Fares et al., *Proc Natl Acad Sci* 1992, 89, 4304-4308; and Furuhashi et al., *Mol Endocrinol* 1995, 9, 54-63). Preferably, the fusion partner is the Fc of an immunoglobulin (e.g., Fc or human IgG1). The Fc can include CH1, CH2 and CH3 of human IgG1, and optionally the human IgG1 hinge region (EPKSCDKTHTCPPCP (SEQ ID NO:13)) or a portion of the human IgG1 hinge region (e.g., DKTHTCPPCP (SEQ ID NO:14) or PKSCDKTHTCPPCP (SEQ ID NO:15)) if desired. In some fusion proteins, the Fc can include CH2 and CH3 of human IgG1, or the Fc of human IgG2 or human IgG4, if desired. Preferably, the sNPP1 fusion protein comprises an NPP1 component and a peptide that increases the half-life of the fusion protein, most preferably the Fc of an immunoglobulin (e.g., Fc or human IgG1). As used herein, a "protein that increases the half-life of the fusion protein" refers to a protein that, when fused to a soluble NPP1 or biologically active fragment, increases the half-life of the soluble NPP1 polypeptide or biologically active fragment as compared to the half-life of the soluble NPP1 polypeptide, alone, or the NPP1 biologically active fragment, alone. In one embodiment, the half-life of the NPP1 fusion protein is increased 50% as compared to the half-life of the NPP1 polypeptide or biologically active fragment, alone. In another embodiment, the half-life of the NPP1 fusion protein is increased 60% as compared to the half-life of the NPP1 polypeptide or biologically active fragment, alone. In another embodiment, the half-life of the NPP1 fusion protein is increased 70% as compared to the half-life of the NPP1 polypeptide or biologically active fragment, alone. In another embodiment, the half-life of the NPP1 fusion protein is increased 80% as compared to the half-life of the NPP1 polypeptide or biologically active fragment, alone. In another embodiment, the half-life of the NPP1 fusion protein is increased 90% as compared to the half-life of the NPP1 polypeptide or biologically active fragment, alone.

In another embodiment, the half-life of the NPP1 fusion protein is increased 2 fold, 3 fold, 4 fold, 5 fold, 6 fold, 7 fold, 8 fold, 9 fold, or 10 fold as compared to the half-life of the NPP1 polypeptide or biologically active fragment, alone. Methods for determining the half-life of a protein or fusion protein are well known in the art. For example, Zhou et al., Determining Protein Half-Lives, *Methods in Molecular Biology* 2004, 284, 67-77 discloses numerous methods for testing of the half-life of a protein. If desired, the fusion protein can be conjugated to polymers or other suitable compounds that extend half-life, such as polyethylene glycol (PEG), can be conjugated to the NPP1 fusion proteins.

In one embodiment, the peptide which increases the half-life of the fusion protein is a CTP sequence (see also, Fares et al., 2010, *Endocrinol.*, 151(9):4410-4417; Fares et al., 1992, *Proc. Natl. Acad. Sci,* 89(10):4304-4308; and Furuhashi et al., 1995, Molec. Endocrinol., 9(1):54-63).

In another embodiment, the peptide which increases the half-life of the fusion protein is an Fc domain of an Ig.

Fusion partners may also be selected to target the fusion protein to desired sites of clinical or biological importance (e.g., site of calcification). For example, peptides that have high affinity to the bone are described in U.S. Pat. No. 7,323,542, the entire teachings of which are incorporated herein by reference. Peptides that can increase protein targeting to calcification sites can contain a consecutive stretch of at least about 4 acidic amino acids, for example, glutamic acids or aspartic acids. Typically, the peptide that targets the fusion protein to calcification sites will comprise between 4 and 20 consecutive acidic amino acids, for example 4, 5, 6, 7, 8, 9, 10, 11, 12, 13, 14, 15, 16, 17, 18, 19 or 20 consecutive amino acids selected from glutamic acid and aspartic acid. The peptide can consist solely of glutamic acid residues, solely of aspartic acid residues, or be a mixture of glutamic acid and aspartic acid residues. A particularly preferred moiety for targeting to sights of calcification is $Asp_{10}$ (SEQ ID NO:18).

In one embodiment, the NPP1 fusion protein of the invention comprises an NPP1 polypeptide and a moiety that increase protein targeting to calcification sites such as a consecutive stretch of acidic amino acids, for example, glutamic acids or aspartic acids.

Suitable peptide linkers for use in fusion proteins are well-known and typically adopt a flexible extended conformation and do not interfere with the function of the NPP1 component or the fusion partners. Peptide linker sequences may contain Gly, His, Asn and Ser residues in any combination. The useful peptide linkers include, without limitation, poly-Gly, poly-His, poly-Asn, or poly-Ser. Other near neutral amino acids, such as Thr and Ala can be also used in the linker sequence. Amino acid sequences which can be usefully employed as linkers include those disclosed in Maratea et al., Gene 1985, 40, 39-46; Murphy et al., Proc Natl Acad Sci USA 1986, 83, 8258-8262; U.S. Pat. Nos. 4,935,233 and 4,751,180. Other suitable linkers can be obtained from naturally occurring proteins, such as the hinge region of an immunoglobulin. A preferred synthetic linker is $(Gly_4Ser)_n$, where n is 1, 2, 3, 4, 5, 6, 7, 8, 9 or 10 (SEQ ID NO:19). Preferably, n is 3 or 4. For example, in some embodiments the linker is $(Gly_4Ser)_3$ (SEQ ID NO:16) and the fusion protein include a linker with the amino acid sequence GlyGlyGlyGlySerGlyGlyGlyGlySerGlyGlyGlyGlySer (SEQ ID NO:16). Typically, the linker is from 1 to about 50 amino acid residues in length, or 1 to about 25 amino acids in length. Frequently, the linker is between about 8 and about 20 amino acids in length.

Preferred NPP1 fusion proteins comprise from N-terminus to C-terminus an NPP1 component, optionally a linker, an Fc region of an immunoglobulin (e.g., human IgG1 Fc optionally including hinge or a portion thereof), optionally a second liner, and optionally a targeting moiety. Thus, the Fc region and the optional targeting moiety, when present, are each located C-terminally to the NPP1 component. The NPP1 component preferably comprises the cysteine-rich region and the catalytic domain of NPP1, lacks the N-terminal cytosolic and transmembrane domains, and optionally contains the C-terminal region.

A preferred fusion protein comprises, from N-terminus to C-terminus, an NPP1 component comprising the cysteine-rich domain, the catalytic domain and the C-terminal region of human NPP1; and the Fc region, including hinge, of a human immunoglobulin. Preferably, the Fc region is from human IgG1. In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:3. SEQ ID NO:3 is the amino acid sequence of sNPP1-Fc fusion protein.

A preferred fusion protein of this type has the amino acid sequence of SEQ ID NO:3.

Another preferred fusion protein comprises, from N-terminus to C-terminus, an NPP1 component comprising the cysteine-rich domain, the catalytic domain and the C-terminal region of human NPP1; a linker (e.g., $(Gly_4Ser)_3$ (SEQ ID NO:16)); and the Fc region, including hinge, of a human immunoglobulin. Preferably, the Fc region is from human IgG1.

Another preferred fusion protein comprises, from N-terminus to C-terminus, an NPP1 component comprising the cysteine-rich domain, the catalytic domain and the c-terminal region of human NPP1; the Fc region, including hinge or a portion thereof, of a human immunoglobulin; and a moiety targeting the fusion protein to sites of calcification. Preferably, the Fc region is from human IgG1. Preferably, the moiety targeting the fusion protein to sites of calcification is $Asp_{10}$ (SEQ ID NO:18). More preferably, the Fc region is from human IgG1 and the moiety targeting the fusion protein to sites of calcification is $Asp_{10}$ (SEQ ID NO:18). In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:4. A preferred fusion protein of this type has the amino acid sequence of SEQ ID NO:4.

Another preferred fusion protein comprises, from N-terminus to C-terminus, an NPP1 component comprising the cysteine-rich domain, the catalytic domain and the c-terminal region of human NPP1; a linker (e.g., $(Gly_4Ser)_3$ (SEQ ID NO:16)); the Fc region, including hinge or a portion thereof, of a human immunoglobulin; and a moiety targeting the fusion protein to sites of calcification. Preferably, the Fc region is from human IgG1. Preferably, the moiety targeting the fusion protein to sites of calcification is $Asp_{10}$ (SEQ ID NO:18). More preferably, the Fc region is from human IgG1 and the moiety targeting the fusion protein to sites of calcification is $Asp_{10}$ (SEQ ID NO:18).

Another preferred fusion protein comprises, from N-terminus to C-terminus, an NPP1 component comprising a portion of the cysteine-rich domain, the catalytic domain and the c-terminal region of human NPP1; optionally a linker (e.g., $(Gly_4Ser)_3$ (SEQ ID NO:16)); the Fc region, including hinge or a portion thereof, of a human immunoglobulin. Preferably, the Fc region is from human IgG1. In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:9, SEQ ID NO:10, SEQ ID NO:11, or SEQ ID NO:12. Preferred fusion protein of this type have the amino acid sequence of SEQ ID NO:9, SEQ ID NO:10, SEQ ID NO:11 or SEQ ID NO:12. In particularly preferred aspects, a fusion protein of SEQ ID NO:3 is administered in accordance with the methods described herein. In other particularly preferred aspect, a fusion protein of SEQ ID NO:4 is administered in accordance with in the methods described herein. In other particularly preferred aspect, a fusion protein of SEQ ID NO:9 is administered in accordance with in the methods described herein. In other particularly preferred aspect, a fusion protein of SEQ ID NO:10 is administered in accordance with the methods described herein. In other particularly preferred aspect, a fusion protein of SEQ ID NO:11 is administered in accordance with the methods described herein. In other particularly preferred aspect, a fusion protein of SEQ ID NO:12 is administered in accordance with the methods described herein.

Fusion proteins of the present invention can be prepared using standard methods, including recombinant techniques or chemical conjugation well known in the art. Techniques useful for isolating and characterizing the nucleic acids and proteins of the present invention are well known to those of skill in the art and standard molecular biology and biochemical manuals can be consulted to select suitable protocols for use without undue experimentation. See, for example, Sambrook et al., 1989, "Molecular Cloning: A Laboratory Manual", $2^{nd}$ ed., Cold Spring Harbor, the content of which is herein incorporated by reference in its entirety. The isolated recombinant human sNPP1, fragment, and fusion proteins thereof, can be produced in any useful protein expression system including, without limitation, cell culture (e.g., CHO cells, COS cells, HEK203), bacteria such as Escherichia coli (E. coli) and transgenic animals, including, but no limited to, mammals and avians (e.g., chickens, quail, duck and turkey). For expression, a construct that encodes the sNPP1 and includes a suitable signal sequence (e.g, from human Ig heavy chain, NPP2, NPP4, NPP7 or human serum albumin, for example) in frame with the sequence of the sNPP1 and operably linked to suitable expression control elements.

The sNPP1, including the fusion proteins, and physiologically acceptable salt forms thereof are typically formulated into a pharmaceutical composition for administration in accordance with the methods described herein. Pharmaceutical compositions typically include a pharmaceutically acceptable carrier or excipient. Compositions comprising such carriers, including composite molecules, are formulated by well-known conventional methods (see, for example, Remington's Pharmaceutical Sciences, 14$^{th}$ ed., Mack Publishing Co., Easton, Pa.), the entire teachings of which are incorporated herein by reference. The carrier may comprise a diluent. In one embodiment, the pharmaceutical carrier can be a liquid and the fusion protein may be in the form of a solution. The pharmaceutical carrier can be wax, fat, or alcohol. In another embodiment, the pharmaceutically acceptable carrier may be a solid in the form of a powder, a lyophilized powder, or a tablet. In one embodiment, the carrier may comprise a liposome or a microcapsule. The pharmaceutical compositions can be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized protein generally has increased stability and a longer shelf life than a liquid solution of the protein.

Equivalents

Those skilled in the art will recognize, or be able to ascertain using no more than routine experimentation, many equivalents of the specific embodiments described herein. Such equivalents are intended to be encompassed by the following claims. Any combination of the embodiments disclosed in the any plurality of the dependent claims or Examples is contemplated to be within the scope of the disclosure.

INCORPORATION BY REFERENCE

The disclosure of each and every U.S. and foreign patent and pending patent application and publication referred to herein is specifically incorporated herein by reference in its entirety, as are the contents of Sequence Listing and Figures.

EXAMPLES

The present invention is further exemplified by the following examples. The examples are for illustrative purpose only and are not intended, nor should they be construed as limiting the invention in any manner.

Example 1

Human Primary Vascular Smooth Muscle Cells (VSMCs)

To assess whether ENPP1 knockdown increases proliferation in human primary vascular smooth muscle cells (VSMCs) the following experiments were conducted using human primary VSMCs obtained from ATCC and ThermoFisher Scientific.

1A. ENPP1 Gene Expression

First, baseline ENPP1 gene expression in human VSMCs was assessed via real time polymerase chain reaction (qRT-PCR), western blot analysis, and an assay to detect cell based ENPP1 enzymatic activity, according to the following protocols.

Real Time Polymerase Chain Reaction (qRT-PCR): Total RNA was isolated from human VSMCs using a Qiagen Rneasy Mini kit (cat #74106) and QIAshredder (cat #79656, QIAGEN, Valencia, Calif.) as per manufacturer's instructions. The isolated RNA was quantified using a Nanodrop2000 (Thermoscientific) and reverse transcribed to cDNA using High-Capacity cDNA Reverse Transcription Kit (Cat #4368814; ThermoFisher Scientific). The resulting cDNA was amplified using the TaqMan Universal PCR Master Mix and detected by real-time PCR using QuantStudio™ 7 Flex System. TaqMan probes for human ENPP1, Hs01054038_m1 and housekeeping gene, glyceraldehyde-3-phosphate dehydrogenase (GAPDH) Hs99999905_m1 were obtained from ThermoFisher Scientific. Target gene expression level was normalized by GAPDH level in each sample and Relative expression level was calculated using 2-ΔΔ Ct method.

1B. Western Blot Analysis

VSMCs were detached, washed in PBS and the cell lysates were prepared in lysis buffer containing 1% each of protease inhibitor, Phosphatase Inhibitor Cocktail 3 (cat #P0044; Sigma) and Phosphatase Inhibitor Cocktail 2 (cat #P5726; Sigma). The cell lysate was quantified and denatured, then equal amounts of the protein were loaded on 4-12% Bis polyacrylamide gels. The proteins in gels were electrophoretically transferred to nitrocellulose membrane using iBlot® 2 Dry Blotting System. Following treatment with blocking buffer (5% skimmed milk in 1XTBST (Cat #IBB-180; Boston Bioproducts)), and incubated with Rabbit pAb to human ENPP1 (PA527905 by Thermo Fischer Scientific) at 1:500 or GAPDH (14C10) Rabbit anti GAPDH mAB by Cell Signaling Technology (cat #2118L) at 1:1000 in blocking buffer for overnight at 4° C., followed by a Goat-anti-Rabbit Antibody conjugated with HRP (cat #7074; Cell signaling technology) for 1 hr. at room temperature. The signals were detected using the Protein Simple FluorChem R system (Part #92-15313-00, ProteinSimple). Signals of ENPP1 protein were normalized with level of endogenous protein GAPDH in each sample.

1C. Cell Based ENPP1 Enzymatic Activity

Cell based ENPP1 enzyme activity was assayed using the colorimetric substrate, p-nitrophenyl thymidine 5'-monophosphate (Cat #T4510, Sigma). Cells were seeded into the well of 96 well maxisorp plate at 300,000 cells/well and 100,000 cells/well and substrate at a final concentration of 1 mM in reaction buffer (200 mM Tris-HCl pH9, 1M NaCl, 10 mM MgCl2, 0.1% (v/v) Triton-X 100) was added to the plate. Enzyme activity is measured the reaction product based on the ability of phosphatases to catalyze the hydrolysis of PNPP to p-nitrophenol with absorbance at 405 nm using a continuous spectrophotometric assay using in a FlexStation® Plate Reader (Molecular Devices) in a kinetic mode with 21 reads at 31 sec intervals. Standard curve was generated using ENPP1-Fc protein ranged from 0 ng/ml to 90 ng/ml. Data was analyzed at 10 minutes respectively.

Figure 1B:
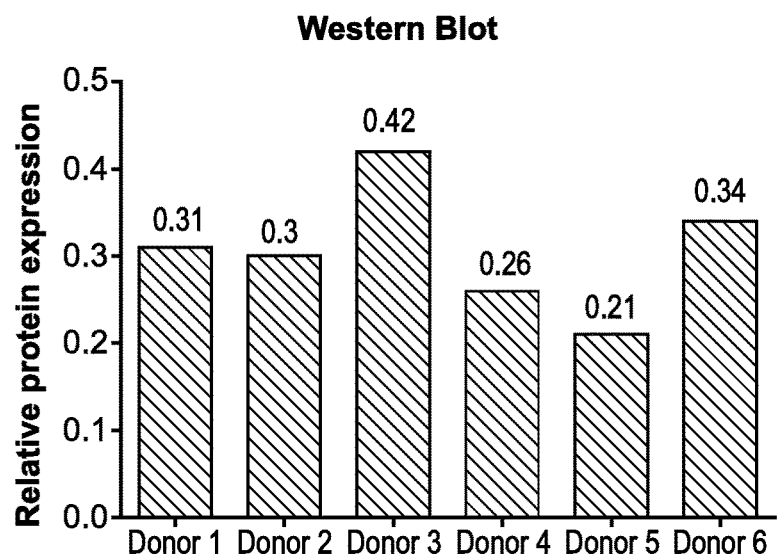
Figure 1C:
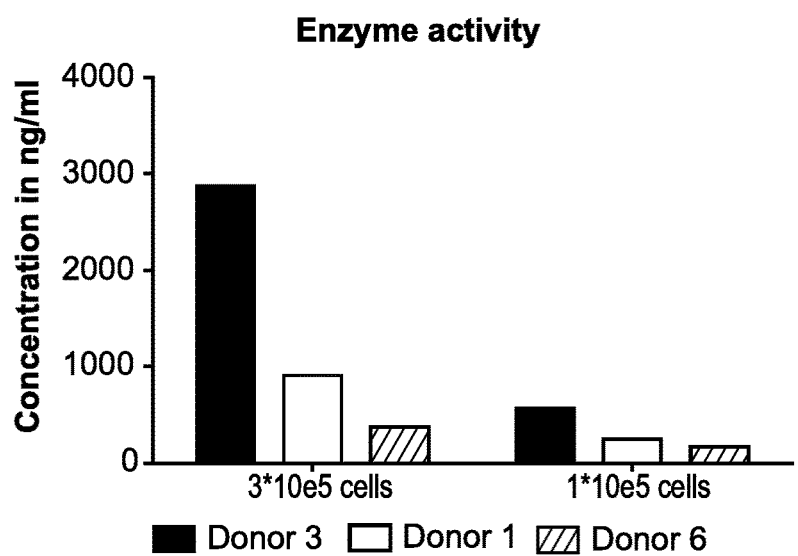

Results: FIG. 1 depicts mRNA (FIG. 1A) and protein (FIG. 1B) ENPP1 expression in human VSMCs from six different donors, as well as enzyme activity from three of the donors (FIG. 1C). As shown in FIG. 1, there was significant natural variability in baseline ENPP1 expression in human primary VSMCs.

1D. ENPP1 Knockdown Using siRNA Targeting Human ENPP1

Human VSMCs (donor 3) were transfected with either ENPP1 siRNA or control siRNA. The following siRNA constructs were used: 1 (ENPPA (CDS) Location: 825), 2 (ENPPA (CDS) Location: 813), 3 (ENPPA (CDS) Location: 1272), 4 (ENPPA (CDS) Location: 447), and 5 (ENPPA (CDS) Location: 444). Human VSMCs (donor 3, passage 4) were transfected with either siRNA targets [Silencer Select ENPP1 siRNA #1: s10264 (Cat #4390824), siRNA #2: s10265 (Cat #4390824), siRNA #3: s10266 (Cat #4390824), siRNA #4: s224228 (Cat #4392420), Silencer ENPP1 siRNA #5: 144240 (Cat #AM90824); Life Technologies] to human ENPP1 or control using the Lipofectamine RNAiMAX (cat #13778500; ThermoFisher Scientific) following the manufacturer's instructions. Cells were seeded in 60 mm dish at density 3500 cells/0.32 cm$^2$ in complete medium (Vascular Cell Basal medium ATCC #PCS-100-030 supplemented with Vascular Smooth Muscle Cell Growth Kit ATCC #PCS-100-042, ATCC). Cells were treated with either an siRNA that specifically targets human ENPP1 or a negative control siRNA at a concentration of 100 nM in OPTI-MEM (cat #31985; ThermoFisher Scientific) and incubated at 37° C. Cells were harvested 48 hours or 6 days or 11 days after transfection (cells for 6 day and 11 day time points were harvested and reseeded at 48 hours), total RNA was extracted and mRNA levels were assayed by reverse transcription and real-time PCR. Levels of ENPP1 mRNA expression are reported as percentage of inhibition in mRNA expression relative to negative-siRNA after normalization to GAPDH mRNA levels.

Figure 2A:
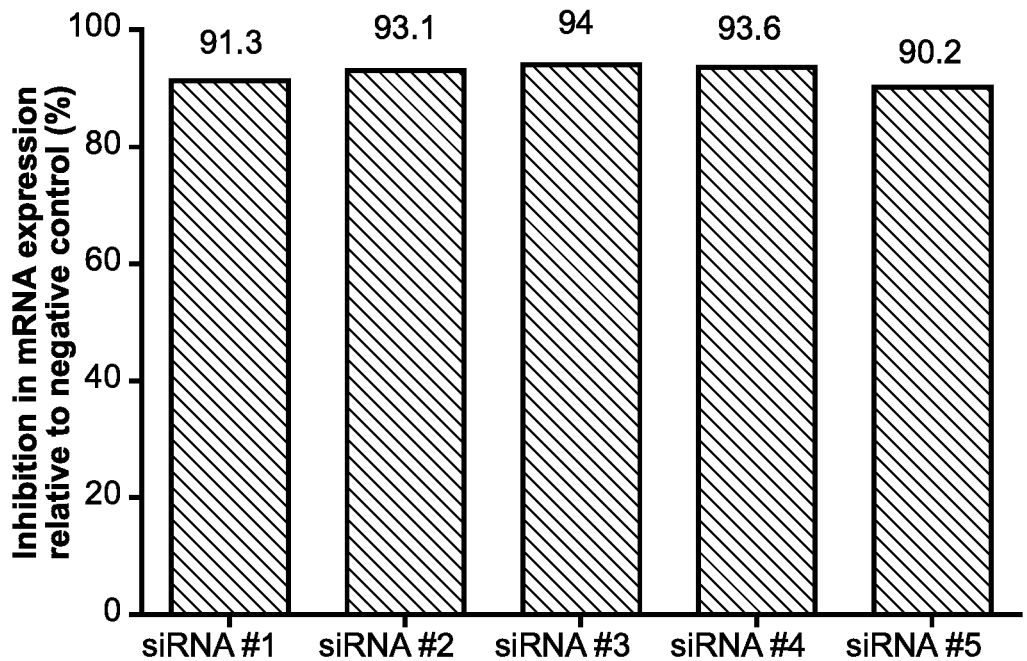
FIGS. 2A-2B depict inhibition of ENPP1 mRNA expression relative to a negative control. Specifically.
Figure 2B:
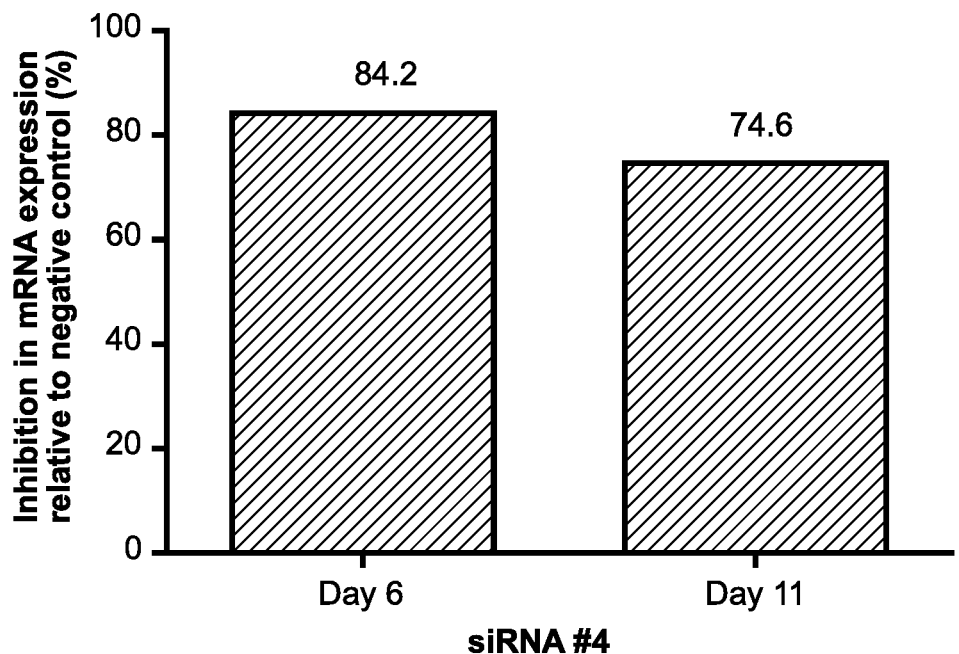

Results: As shown in FIG. 2A, ENPP1 mRNA expression was inhibited by 90% or greater relative to the negative control for all five siRNA constructs, 48 hours post siRNA transfection. Specifically, ENPP1 mRNA expression was inhibited by 91.3% using siRNA construct #1, 93.1% using siRNA construct #2, 94% using siRNA construct #3, 93.6% using siRNA construct #4, and 90.2% using siRNA construct #5, relative to the negative control. Moreover, as shown in FIG. 2B, ENPP1 mRNA expression was inhibited by 84.2% six days post siRNA transfection with construct #4 (relative to the negative control) and 74.6% eleven days post siRNA transfection with construct #4 (relative to the negative control). Accordingly, the data indicates that siRNA sufficiently silences ENPP1 expression for a prolonged period of time.

1E. Effect of ENPP1 Knockdown on Proliferation

Human VSMCs (Donor 1 and Donor 3, passage 4) were seeded in 60 mm dishes at density 0.3*10e6 cells/60 mm dish in Complete Medium (Cat #PCS-100-042, PCS-100-030; ATCC). After overnight recovery, they were transfected with ENPP1 siRNA or control siRNA in OPTI-MEM. After 48 hours, cells were harvested and reseeded at 2500 cells/well into 96 well plate. Cells were cultured in basal medium containing 2% or 5% FBS. Cell proliferation was evaluated by [3H] thymidine uptake. [3H]-thymidine was added in the last 18 hours of culture. Results are expressed as CPM±SEM. Experiments were triplicated.

Figure 3A:
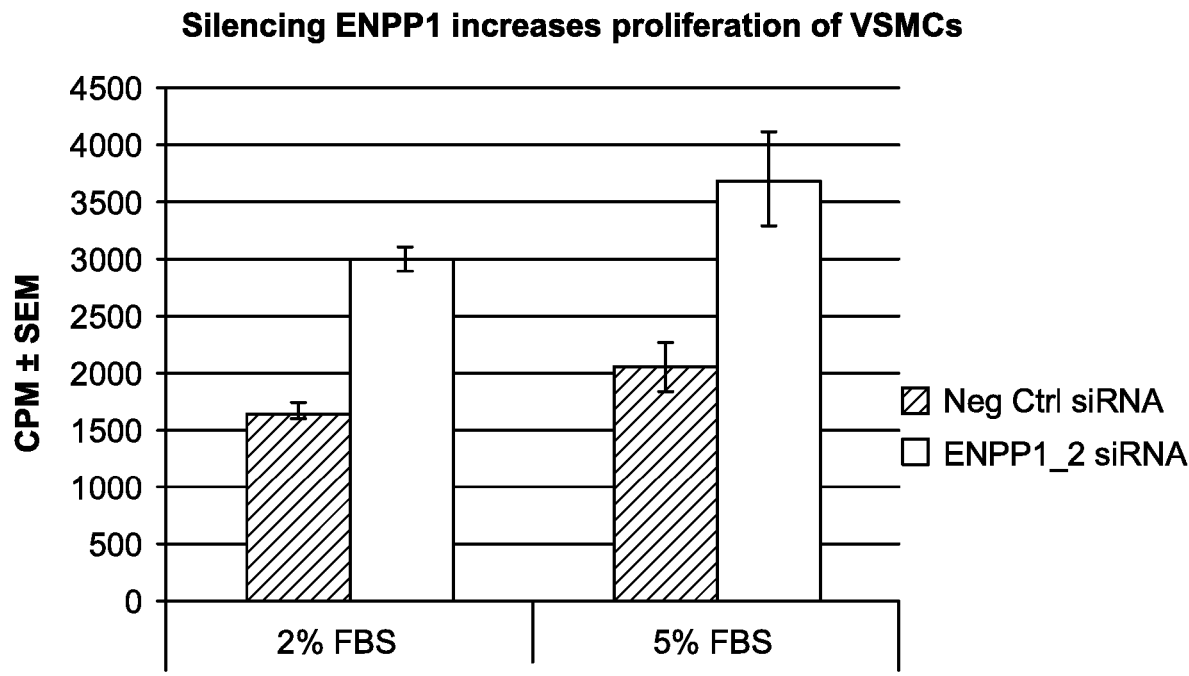
FIGS. 3A-3B depict the effect of silencing ENPP1 by siRNA on proliferation of human primary VSMCs from two different donors.
Figure 3B:
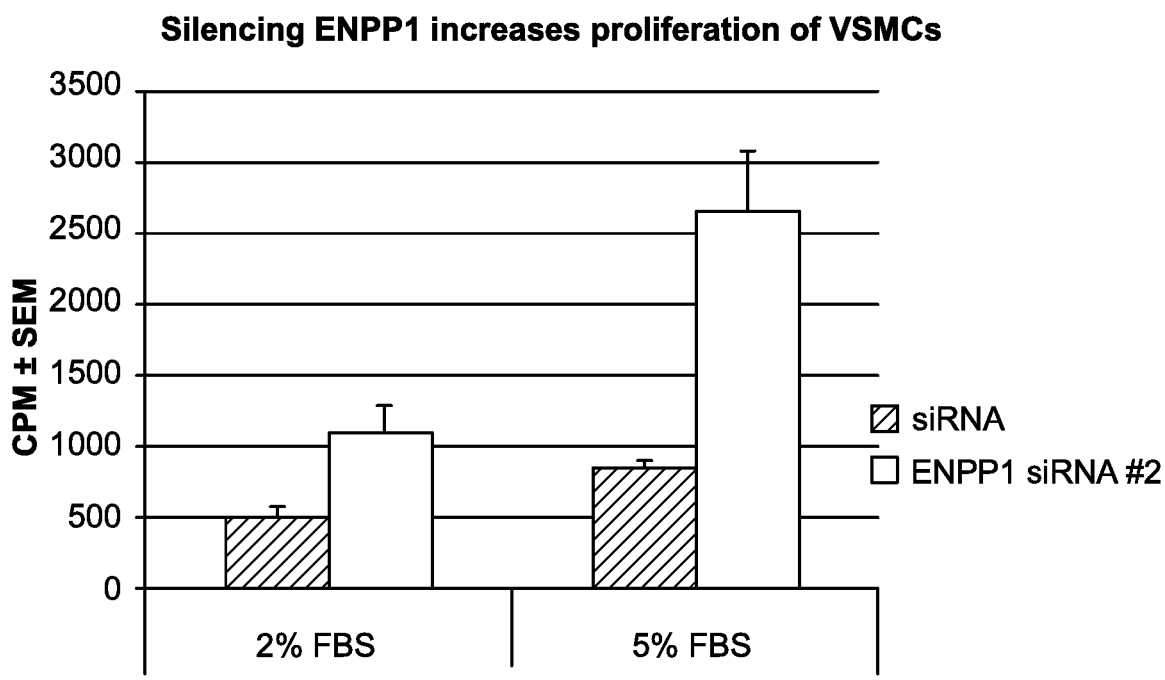

Results: As shown in FIGS. 3A (Donor 1) and 3B (Donor 3) and Table 1 (Donor 3), silencing of ENPP1 by siRNA increased proliferation of human primary VSMCs from these two different donors (e.g., by about 1.75 fold or greater) compared to negative control siRNA.

TABLE 1

| siRNA | ENPP1 (CDS) | Inhibition of ENPP1 at 48 hrs. |
|---|---|---|
| siRNA ENPP1 | 813 | 84.7% |
| siRNA_NC | N/A | 0.0% |

1F. Effect of ENPP1 Knockdown on Cell Proliferation

Human VSMCs (Donor 1 and Donor 3, passage 4) were seeded in 60 mm dishes at density 0.3*10e6 cells/60 mm dish in Complete Medium (Cat #PCS-100-042, PCS-100-030; ATCC). After overnight recovery, they were transfected with ENPP1 siRNA or control siRNA in OPTI-MEM. After 48 hours, cells were harvested and reseeded at 2500 cells/well into 96 well plate. Cells were cultured in basal medium containing 5% FBS for 3 or 4 days. Cells were detached and stained with AOPI at indicated time point, cell number was measured using auto cell counter Cellometer Auto 2000. Results were expressed as Cell number±SEM. Experiments were triplicated.

Figure 4A:
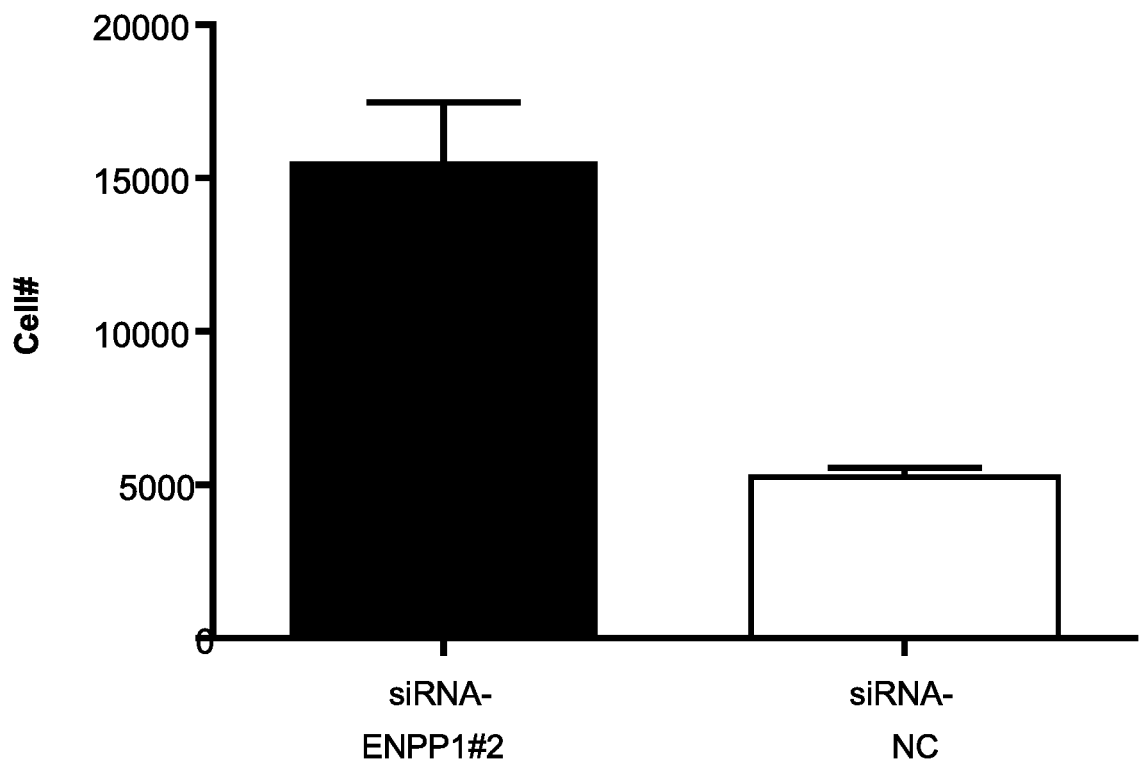
FIGS. 4A-4B depict the effect of silencing ENPP1 by siRNA on human primary VSMC cell growth on Day 3 (FIG. 4A) and Day 4 (FIG. 4B).
Figure 4B:
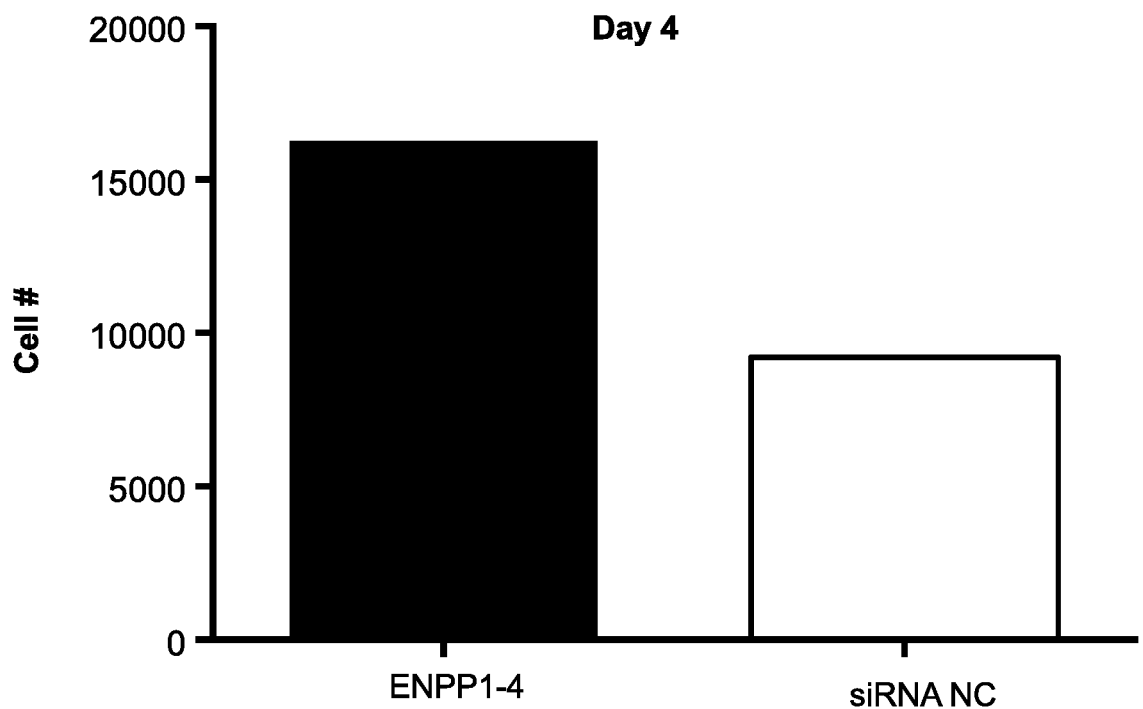

Results: As shown in FIGS. 4A (Day 3) and 4B (Day 4) representing Donor 3, silencing ENPP1 using siRNA increased cell growth in human primary VSMCs. Specifically, cell growth was at least two fold or greater 3-4 days after silencing ENPP1 using two different constructs. These results are consistent in light of results found from independent experiments, independent analysts, different constructs, same donor, and different methods.

Example 2

Rat Primary Vascular Smooth Muscle Cells (VSMCs)

To assess whether ENPP1 knockdown increases proliferation, the following experiments were conducted using rat primary VSMCs.

First, an in vitro primary rat VSMC Model system was established. Primary rat vascular smooth muscle cells (VSMCs) were prepared by using enzymatic digestion of thoracic arteries from 3-week-old Sprague-Dawley rats. Small fragments were minced and digested at 37° C. in vascular cell basal media (ATCC) supplemented collagenase type II 2 mg/ml (Cat #17101-015, Gibco) for 3 hours, mix every 15 minutes and replace digestion solution hourly. Then, the cell suspension was centrifuged at 1000 rpm for 10 min at 4° C., the pellet was resuspended in complete medium and cultured into T75 flasks. Cells were cultured in vascular cell basal media (ATCC #PCS-100-030) containing 5% fetal bovine serum, and growth supplements (Cat #PCS-100-042, ATCC containing with 5 ng/ml rhFGF, 5 µg/ml rh Insulin, 50 µg/ml Ascorbic acid, 10 mM L-gutamine, 5 ng/ml rhEGF, penicillin 10 Units/ml, streptomycin 10 µg/ml, and Amphotercin B 25 ng/ml). VSMCs were subcultured and used between passages 3-4. ENPP1 knockdown was achieved by transfection with siRNA. Specifically, transfection of VSMCs with siRNA was performed using Lipofectamine RNAiMAX (cat #13778500; ThermoFisher Scientific) according to the manufacturer's instructions.

2A. Effect of Silencing ENPP1 on Pharmacological Activity

Rat primary VSMCs (passage 3) were seeded into 60 mm dish at density 0.3*10e6/60 mm dish in complete medium and transfected with either one of a siRNA specific targets to rat ENPP1 or negative control siRNA at a concentration of 100 nM in OPTI-MEM (cat #31985; ThermoFisher Scientific) and incubated at 37° C. Cells were harvested at 48 hours and reseeded in the wells of 6 well plate at 37500 cells/well in complete medium. Cells were then harvested at indicated time points after transfection, total RNA was extracted and mRNA levels were assayed by reverse transcription and real-time PCR. Levels of ENPP1 mRNA expression are reported as percentage of inhibition in mRNA expression relative to negative-siRNA after normalization to GAPDH mRNA levels (see FIG. 5A).

Rat VSMCs (passage 3) were transfected with either ENPP1 siRNA or control siRNA for 48 hours, then seeded into the wells of 6-well plate at 37500 cells/well (2 wells per condition), the cells were stimulated with Complete Medium (Cat #PCS-100-042, PCS-100-030; ATCC). Cells were detached at indicated time points and stained with AOPI, cell number was measured using auto cell counter, Cellometer Auto 2000. Results are expressed as Cell number±SEM (see FIG. 5B). Experiments were triplicated.

ENPP1 enzyme activity was assayed using the colorimetric substrate, p-nitrophenyl thymidine 5'-monophosphate (Cat #T4510, Sigma). Cells were seeded into the well of 96 well plate at 20000 cells/well and substrate at 1 mM p-nitrophenyl thymidine 5'-monophosphate in reaction buffer was added. Enzyme activity was measured the reaction product based on the ability of phosphatases to catalyze the hydrolysis of PNPP to p-nitrophenol with absorbance at 405 nm using a continuous spectrophotometric assay using in a FlexStation® Plate Reader (Molecular Devices) in a kinetic mode with 21 reads at 31 sec intervals. Standard curve was generated using ENPP1-Fc protein ranged from 0 ng/ml to 90 ng/ml. Data was analyzed using SoftMax Pro software at 10 minutes. ENPP1 activity in each sample was calculated based on the standards (see FIG. 5C).

Figure 5A:
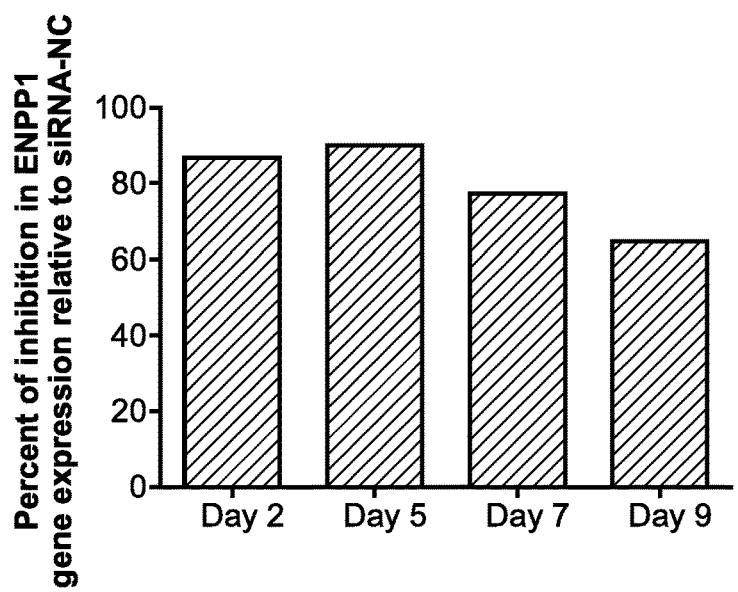
FIGS. 5A-5B depict the effect of siRNA silencing on levels of ENPP1 mRNA expression (FIG. 5A), cell growth (FIG. 5B), and enzyme activity (FIG. 5C) in rat VSMCs.
Figure 5B:
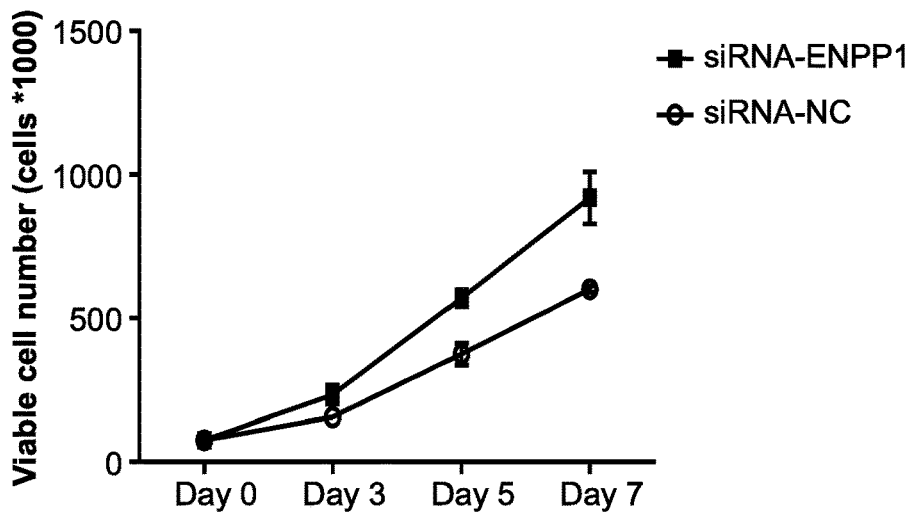
Figure 5C:
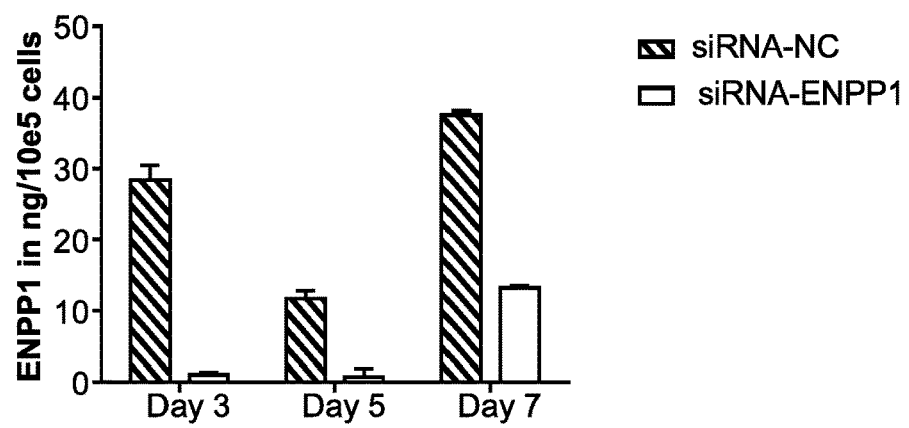

As shown in FIGS. 5A-5C, siRNA silencing of ENPP1 was robust and durable (FIG. 5A), increased cell growth (FIG. 5B), and decreased enzyme activity (FIG. 5C).

2B. Effect of Adenosine, AMP, or PPi on Proliferation of Rat VSMCs

Rat VSMCs (p3) were transfected with either rat ENPP1-siRNA or control siRNA for 48 hrs and then seeded into wells of 96-well plate at 2500 cells/well. Cells were then cultured in complete medium in the presence and absence of Adenosine monophosphate (AMP) (Cat #A1752, Sigma), adenosine (A4036, Sigma) or PPi (Cat #71515, Sigma). Cell proliferation was evaluated on day 3 by [3H] thymidine uptake. Results are expressed as CPM±SEM. Experiments were triplicated.

Figure 6A:
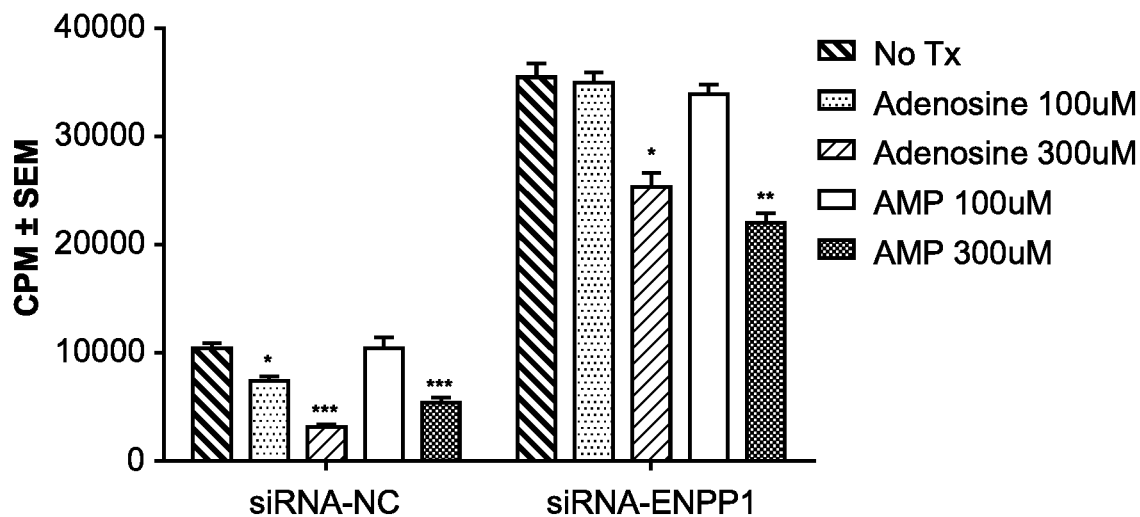
FIGS. 6A-6B depict the effect of adenosine (FIG. 6A), AMP (FIG. 6A), and PPi (FIG. 6B) on proliferation of rat VSMCs that were knocked down with ENPP1.
Figure 6B:
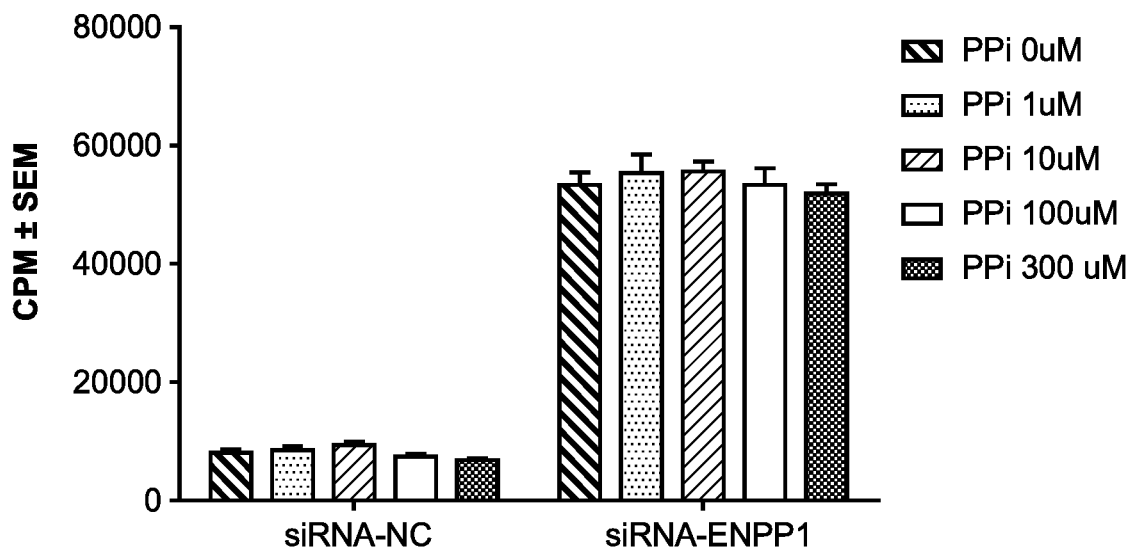

As shown in FIG. 6A, adenosine and AMP inhibited proliferation in rat VSMCs that were knocked down with ENPP1 and without regulated ENPP 1. However, PPi did not affect proliferation in rat VSMCs (FIG. 6B).

2C. Effect of Bisphosphonate on Proliferation of Rat VSMCs

Rat VSMCs (p3) were transfected with either rat ENPP1-siRNA or control siRNA for 48 hrs., then seeded into wells of 96-well plate at 2500 cells/well, cells were cultured in complete medium in the presence and absence of Etidronate (Cat #P5248, Sigma) at indicated concentration. Cell proliferation was evaluated on day 3 by [3H] thymidine uptake. Results are expressed as CPM±SEM. Experiments were triplicated. Data was reproducible with Zoledronate as well.

Figure 7:
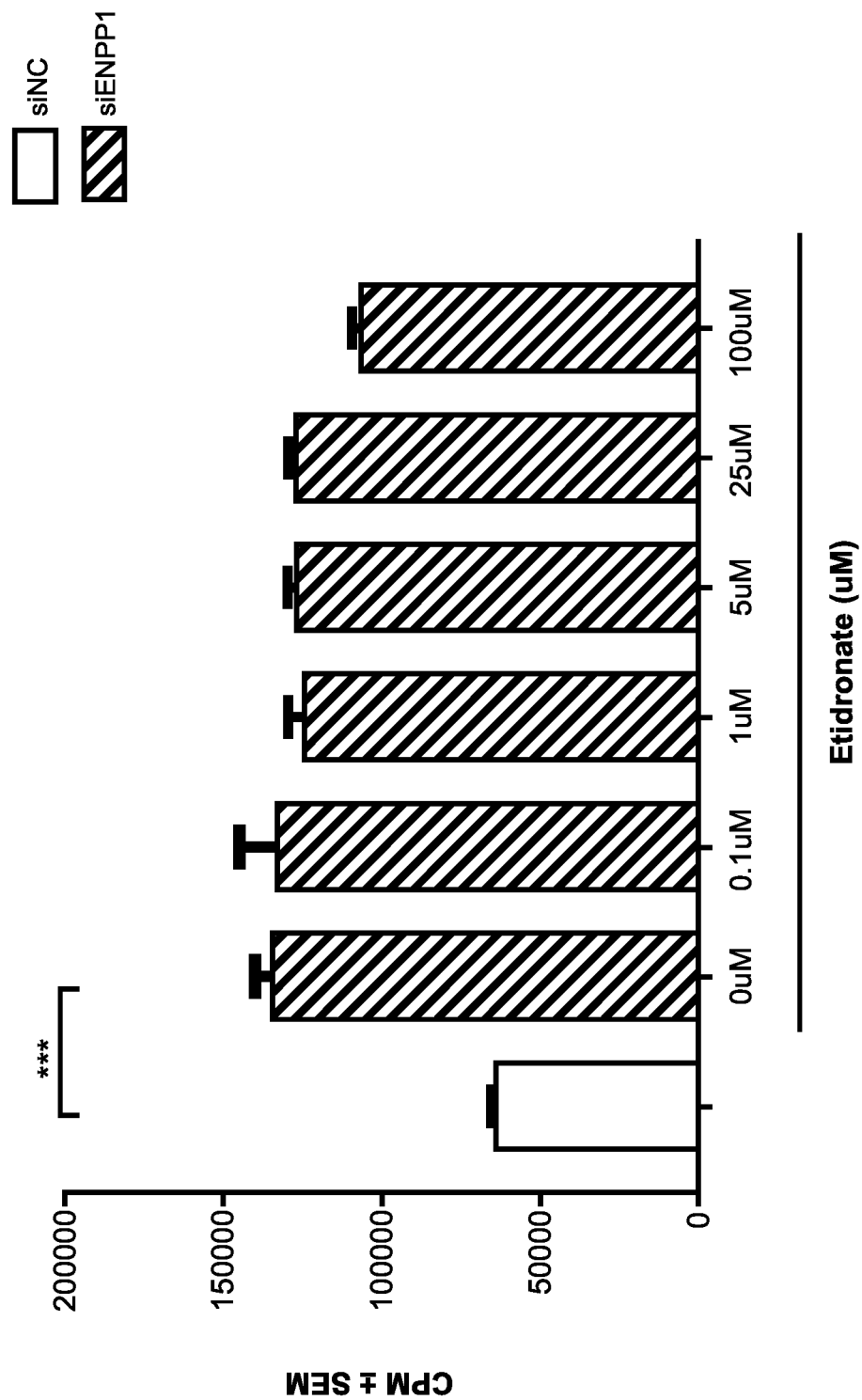
FIG. 7 depicts the effect of bisphosphonate on proliferation of rat VSMCs.

As shown in FIG. 7, bisphosphonate did not appear to inhibit proliferation in rat VSMCs.

2D. Effect of Silencing ENPP1 on Proliferation of Rat VSMCs

Figure 8A:
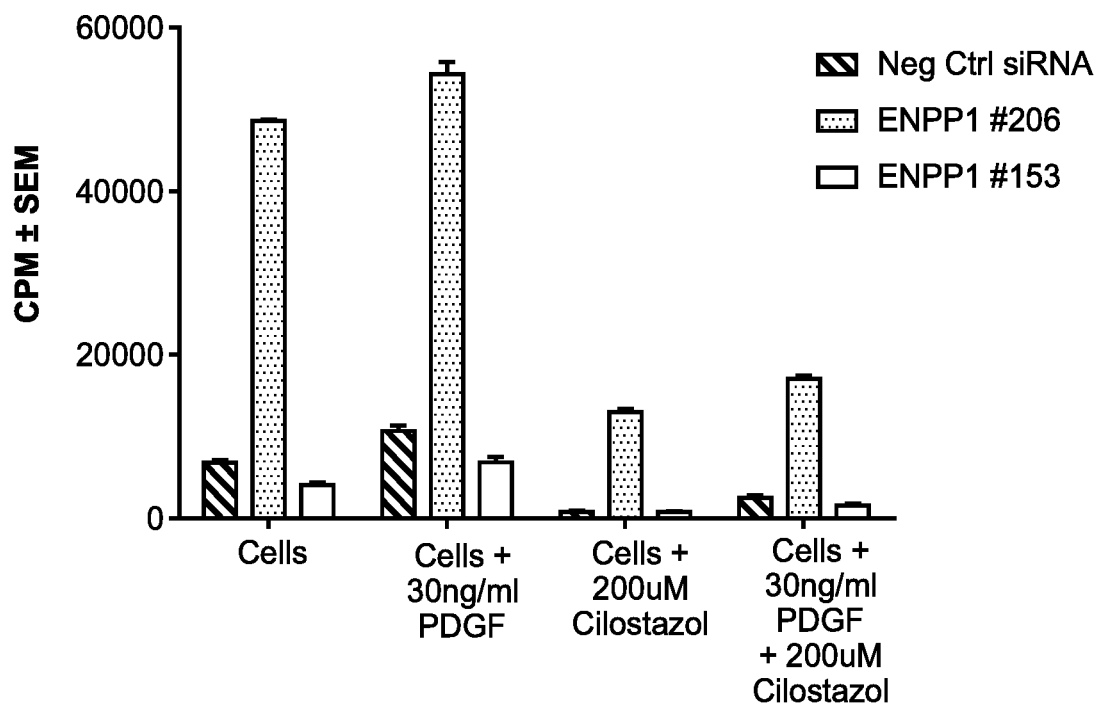
FIGS. 8A-8B depict the effect of silencing ENPP1 using different siRNA constructs on proliferation in rat VSMCs. Specifically.

Rat VSMCs were transfected with siRNA against rat ENPP1 si206 (ENPP1 sequence start position: 462; (Cat #SASI_Rn01_00111206 NM_053535, Sigma)), rat ENPP1 si153 (ENPP1 sequence start position: 516 (Cat #SASI_Rn02_00266153 NM_053535, Sigma)), or a negative control (FIG. 8A). After 48 hours transfection, cells were seeded into wells of 96-well plate at 1250 cells/well in complete medium. After 4 hours, following treatment conditions were added in complete medium: PDGF (Cat #P8953, Sigma), Cilostazol (Cat #0737, Sigma), PDGF+Cilostazol at indicated concentration. [3H] thymidine was added in the last 18 hours of culture. Cell proliferation was evaluated by [3H] thymidine uptake. [3H]-thymidine was added in the last 18 hours of culture. Results are expressed as CPM±SEM. Experiments were triplicated.

Figure 8B:
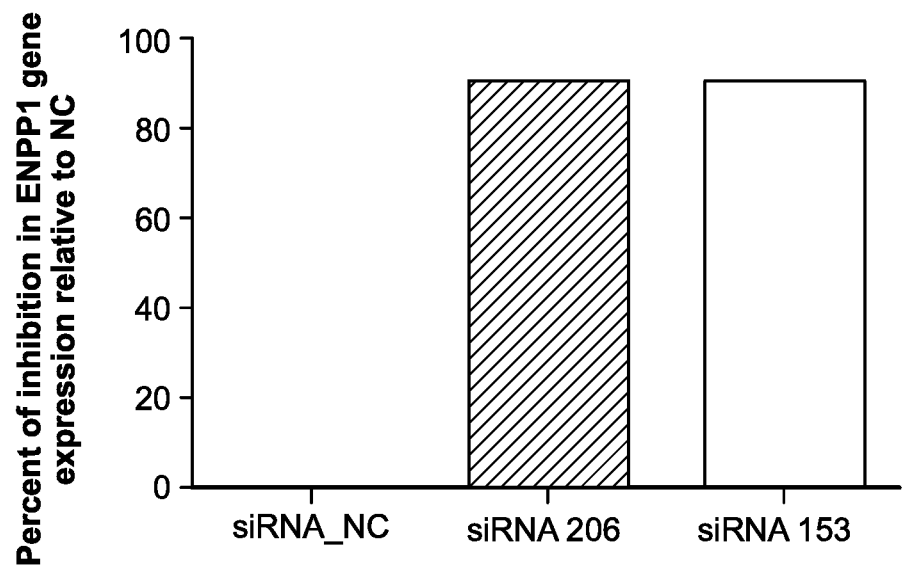

As shown in FIGS. 8A-8B, silencing ENPP1 by siRNA increased proliferation in rat VSMCs, but was inconsistent between constructs.

Example 3

Overexpression of Mouse or Rat ENPP1 in Rat Primary Vascular Smooth Muscle Cells (VSMCs)

Experiments were conducted to assess whether overexpressed ENPP1 rescues proliferation of VSMCs. The following constructs were used: (1) siRNA target rENPP1: (SASI_Rn01_00111206) Cat #PDSIRNA2D, Sigma, (2) Ad-mENPP1: Vector Biolab (Lot #20150616T #10; Vector Biolabs), (3) Ad-rENPP1: Life Tech+Vector Biolab (Lot #20150714T #11; Vector Biolabs), and (4) Ad-rENPP1: GeneWiz+Vector Biolab (Lot #20150714T #9; Vector Biolabs).

3A. Ad-mENPP1/Ad-rENPP1 Induces Overexpression of Mouse/Rat ENPP1 mRNA Specifically in Rat VSMC Co-transfection with Ad-GFP and siRNA: Rat VSMCs (passage 3) were seeded in the wells of 6-well plates at 6000 cells/0.32 cm2 in complete medium. After overnight culture, the cells were transfected with siRNA targets to rat ENPP1 using Lipofectamine RNAiMAX. After 4 hours incubation, siRNA was removed and the adenoviral vector Ad-GFP (cat #1060, Vector Biolabs) was added to the cells at multiplicities of infection (MOI) dose of 400. The plates were spun at 37° C. for 1.5 hrs. at 900 g and incubated at 37° C. for next 30 minutes before removing the adenoviral particles and washing with PBS. The siRNA particles were added again and left for overnight infection. The efficacy of adenovirus infectivity was measured 45 hours after infection of Ad-GFP under a fluorescent microscope (DMI8 Leica Microsystems) at 100× magnification.

Co-transfection with Ad-mENPP1 and siRNA-NC: The primary Rat Vascular Smooth Muscle Cells (Rat VSMC) (Passage 3) were seeded at 6000 cells/0.32 cm2 in a 6 well dish in complete medium (Vascular Cell Basal medium ATCC #PCS-100-030 supplemented with Vascular Smooth Muscle Cell Growth Kit ATCC #PCS-100-042). After overnight recovery of the cells, the cells were infected with siRNA particles using Lipofectamine RNAiMAX (cat #13778500; ThermoFisher Scientific) diluted in OPTI-MEM (cat #31985; ThermoFisher Scientific) containing 0.25% FBS. After 4 hours, remove the media and add the adenoviral particles at MOI=400. Three adenoviral particles tested are Ad-rENPP1(Lot #20150714T #9; Vector Biolabs), Ad-rENPP1(Lot #20150714T #11; Vector Biolabs) and Ad-mENPP1 (Lot #20150616T #10; Vector Biolabs). The plates were spun at 37° C. for 1.5 hrs at 900 g and incubated at 37° C. for next 30 minutes before removing the adenoviral particles and washing with PBS. The siRNA particles were added again and left for overnight infection. Cells were harvested 48 hours after infection with Ad-mENPP1. Total RNA was extracted and mRNA levels were assayed by reverse transcription and real-time PCR using primer specific to mouse ENPP1 or rat ENPP1. Levels of mENPP1 mRNA expression are reported as percentage of mRNA expression relative to negative control Ad after normalization to GAPDH mRNA levels.

Real Time Polymerase Chain Reaction (qRT-PCR): RNA isolation and reverse transcription were performed using the TaqMan® Gene Expression Cells-to-CT™ Kit (Cat #AM1729, Thermofisher Scientific) as per manufacturer's instructions in a 96-well plate format, 96 hours post co-transfection. The resulting cDNA is amplified using the TaqMan Universal PCR Master Mix and detected by real-time PCR using QuantStudio™ 7 Flex System in a 384 well-plate. TaqMan probes for rat ENPP1 (AJKAK71), Menpp1 (Mm00501088_m1) and housekeeping gene, glyceraldehyde-3-phosphate dehydrogenase (GAPDH) Rn01775763_g1 were obtained from ThermoFisher Scientific. Target gene expression level was normalized by GAPDH level in each sample and Relative expression level was calculated using ΔCt method.

The Rat ENPP1 (AJKAK71) taqman probe was custom designed to detect the rENPP1 in the adenoviral vector cassette while the mouse ENPP1 (Mm00501088_m1) taqman probe was a premade probe from ThermoFisher Scientific.

Figure 9A:
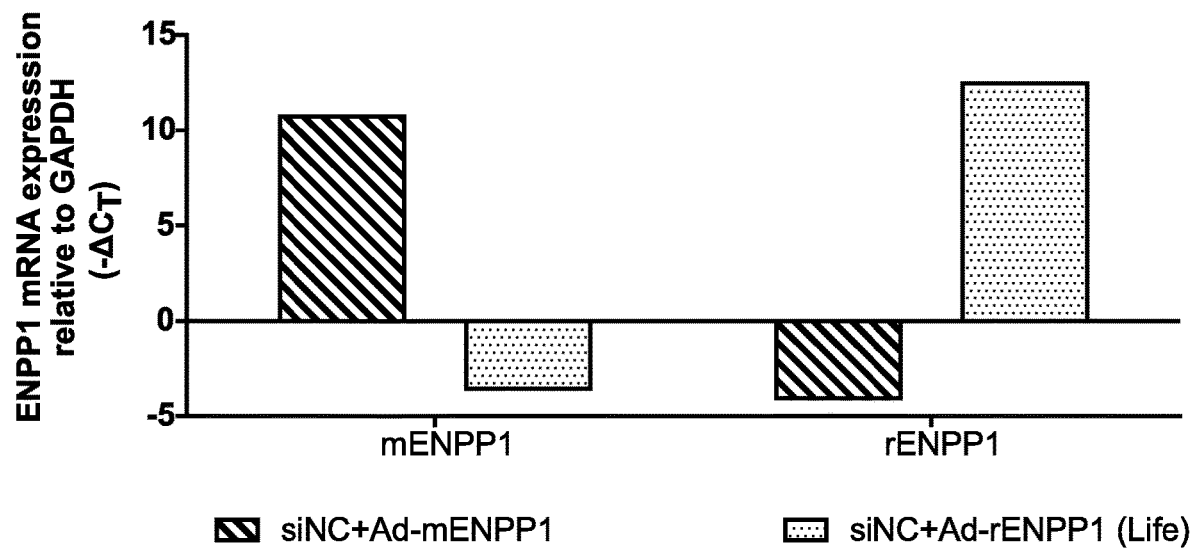
FIG. 9A depicts the effect of Ad-mENPP1/Ad-rENPP1 on Mouse/Rat ENPP1 messenger RNA specifically in rat VSMCs.
Figure 9B:
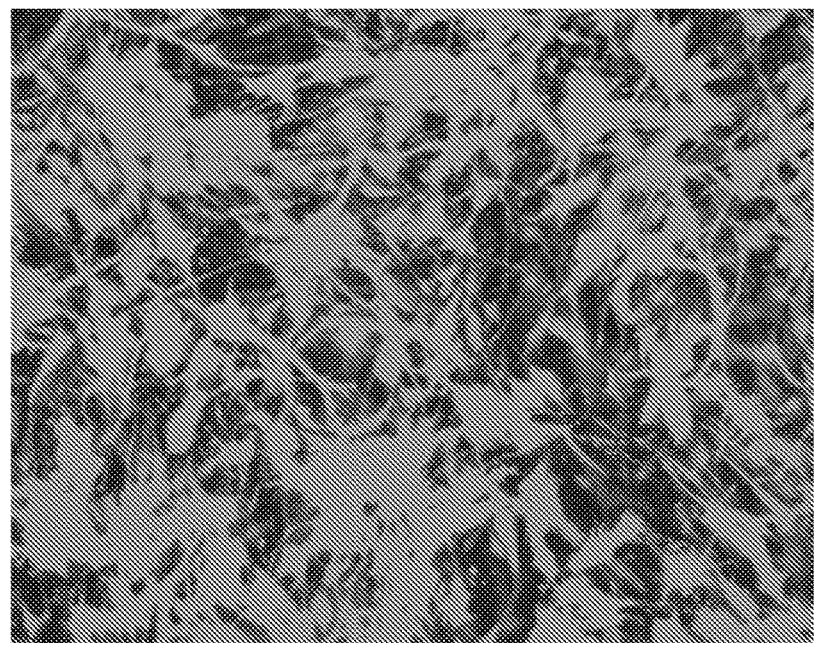
FIG. 9B shows the distribution of GFP following co-transfection of siRNA and Ad-GFP.

As shown in FIG. 9A, Ad-mENPP1/Ad-rENPP1 induced overexpression of Mouse/Rat ENPP1 messenger RNA specifically in rat VSMC. Nearly 100% of VSMCs expressed high level GFP 45 hrs. after co-transfection with siRNA and Ad-GFP (FIG. 9B). Moreover, there was specific overexpression of mouse and rat ENPP1 in co-transfected Rat VSMC starting at the 48 hour timepoint, which and persisted through 96 hours.

3B. mENPP1 mRNA Over-expression Persists in Presence of siRNA Targeting Rat ENPP1, But With Moderate Interference of Mouse ENPP1

Co-transfection with Ad-ENPP1 and siRNA: Rat VSMCs (passage 3) were seeded in the wells of 6-well plates at 6000 cells/0.32 cm² in complete medium. After overnight culture, the cells were transfected with siRNA targets to rat ENPP1 (si206) or siRNA negative control (siNC) using Lipofectamine RNAiMAX. After 4 hours incubation, siRNA was removed and the adenoviral vector contains mouse ENPP1 cDNA sequence (Ad-mENPP1) was added to the cells at multiplicities of infection (MOI) dose of 400. The plates were spun at 37° C. for 1.5 hrs at 900 g and incubated at 37° C. for next 30 minutes before removing the adenoviral particles and washing with PBS. The siRNA particles were added again and left for overnight infection. Cells were harvested 48 hours after infection of Ad-mENPP1. Total RNA was extracted and mRNA levels were assayed by reverse transcription and real-time PCR. Levels of ENPP1 mRNA expression are reported as percentage of mRNA expression relative to negative-siRNA after normalization to GAPDH mRNA levels. Ps: siNC (Silencer Select ENPP1 siRNA s10265 (5 nmol)) Cat #4390824, ThermoFisher Scientific. siRNA Rat enpp1 (SASI_Rn01_00111206) Cat #PDSIRNA2D, Sigma.

Figure 10:
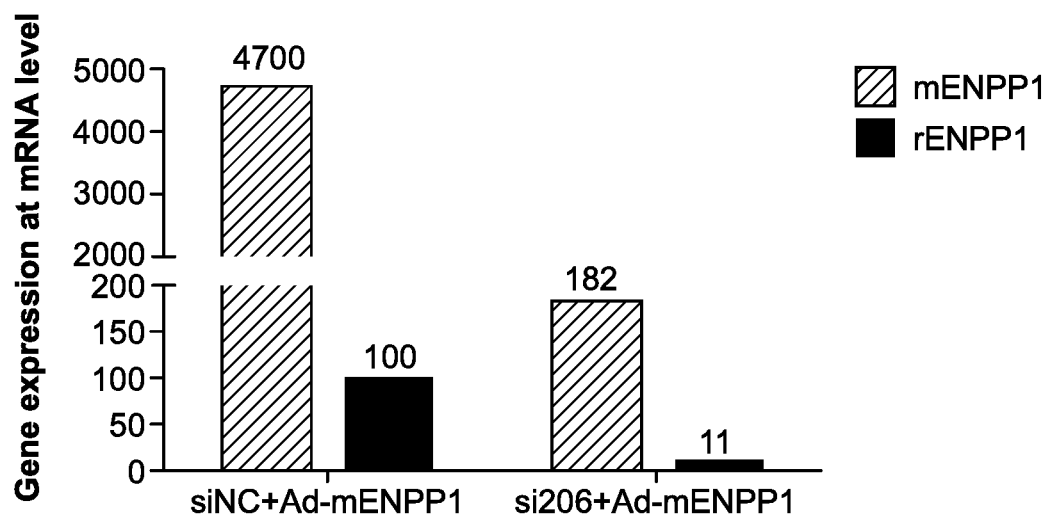
FIG. 10 shows that siRNA specific to rat ENPP1 partially affected Ad-mENPP1 on Mouse ENPP1 messenger RNA specifically in co-transfection siRNA with Ad-mRNPP1 in rat VSMCs.

As shown in FIG. 10, mENPP1 mRNA overexpression persisted in the presence of siRNA targeting rat ENPP1, but with moderate interference of mouse ENPP1. Mouse ENPP1 exhibited 92% homology to rat ENPP1 at the gene level. Accordingly, siRNA knock down of rat ENPP1 expression also partially down regulated mouse ENPP1 expression.

3C. Successful Rescue ENPP1 Protein Expression by Ad-rENPP1

Co-transfection with Ad-ENPP1 and siRNA: Rat VSMCs (passage 3) were seeded in the wells of 6-well plates at 6000 cells/0.32 cm2 in complete medium. After overnight culture, the cells were transfected with siRNA targets to rat ENPP1 (si206) or siRNA negative control (siNC) using Lipofectamine RNAiMAX. After 4 hours incubation, siRNA was removed and the adenoviral vector contains mouse ENPP1 cDNA sequence (Ad-rENPP1) was added to the cells at multiplicities of infection (MOI) dose of 400. The plates were spun at 37° C. for 1.5 hrs at 900 g and incubated at 37° C. for next 30 minutes before removing the adenoviral particles and washing with PBS. The siRNA particles were added again and left for overnight infection. Cells were harvested 72 hours after infection of Ad-rENPP1. ENPP1 protein levels were measured using in cell western blot assay.

In cell western: The cells were fixed in 4% Formaldehyde (w/v), Methanol-free (cat #28908, Pierce™) for 20 min at room temperature. The formaldehyde was removed under a fume hood and the cells were washed twice with 200 µl of PBS. The cells were permeabilized in 100 µl/well (Cat #3603, Costar) of 0.1% Triton x-100 in PBS for 20 min at Room temperature. Then, the cells were blocked using LICOR TBS blocking buffer (P/N 927-50000) for 1 hr. at Room Temperature followed by overnight incubation at 4° C. with 2.5 µg/ml primary antibody Goat anti-ENPP1/PC1 (Cat #OAEB02445, Aviva) in LICOR TBS blocking buffer containing 0.2% Tween20. The wells were washed thrice with 200 µl of 1× TBST and incubated with secondary antibody IRDye® 800CW Donkey-anti-Goat (P/N 926-32214) Antibody at 1:1000 for 1 hr. at Room Temperature covered in foil. The wells were washed thrice with 200 µl of 1× TBST and rinsed with TBS once to get rid of tween. Image the plate in LICOR Odessey Clx.

Figure 11:
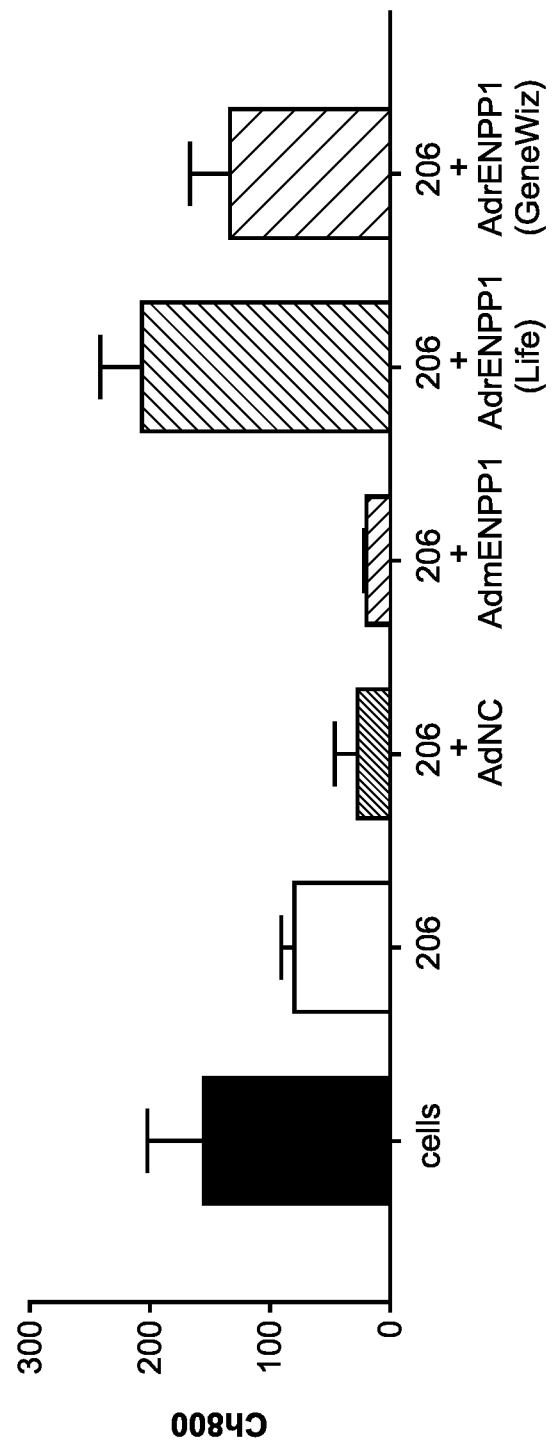
FIG. 11 depicts the effect of Ad-rENPP1 on ENPP1 protein expression.

As shown in FIG. 11, ENPP1 protein expression was successfully rescued by Ad-rENPP1.

3D. Overexpression of mENPP1 Rescues Enzyme Activity in rVSMCs and A10 Cells

Co-transfection with Ad-ENPP1 and siRNA: Rat VSMCs (passage 3) (upper) or rat non-differentiated VSMCs A-10 cells (ATCC, CRL-1476) were seeded in the wells of 6-well plates at 6000 cells/0.32 cm2 in complete medium. After overnight culture, the cells were transfected with siRNA targets to rat ENPP1 (si206) or siRNA negative control (siNC) using Lipofectamine RNAiMAX. After 4 hours incubation, siRNA was removed and the adenoviral vector contains mouse ENPP1 cDNA sequence (Ad-rENPP1) was added to the cells at multiplicities of infection (MOI) dose of 400. The plates were spun at 37° C. for 1.5 hrs at 900 g and incubated at 37° C. for next 30 minutes before removing the adenoviral particles and washing with PBS. The siRNA particles were added again and left for overnight infection. Cells were harvested 72 hours after infection of Ad-rENPP1. Cell based ENPP1 enzyme activity was using the colorimetric substrate, p-nitrophenyl thymidine 5'-monophosphate (Cat #T4510, Sigma). Cells were seeded into the well of 96 well Maxisorp plate at 20000 cells/well and substrate at 1 mM p-nitrophenyl thymidine 5'-monophosphate in reaction buffer was added. Enzyme activity is measured the reaction product based on the ability of phosphatases to catalyze the hydrolysis of PNPP to p-nitrophenol with absorbance at 405 nm using a continuous spectrophotometric assay using in a FlexStation® Plate Reader (Molecular Devices) in a kinetic mode with 21 reads at 31 sec intervals. Standard curve was generated using ENPP1-Fc protein ranged from 0 ng/ml to 90 ng/ml. Data was analyzed using SoftMax Pro software at 10 minutes. ENPP1 activities in each sample was calculated based on the standards. siNC (Silencer Select ENPP1 siRNA s10265 (5 nmol)) Cat #4390824, ThermoFisher Scientific siRNA Rat enpp1 (SASI_Rn01_00111206) Cat #PDSIRNA2D, Sigma.

Figure 12A:
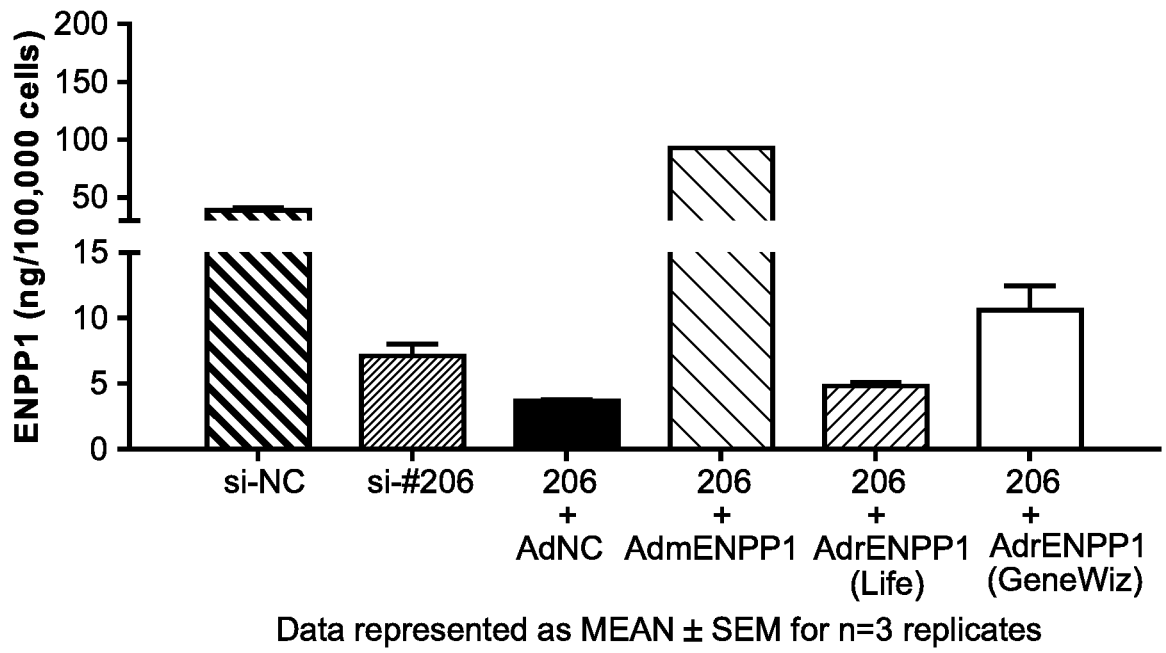
FIGS. 12A-12B depict the effect of mENPP1 overexpression on enzyme activity in rat VSMCs (FIG. 12A) and A10 cells (FIG. 12B).
Figure 12B:
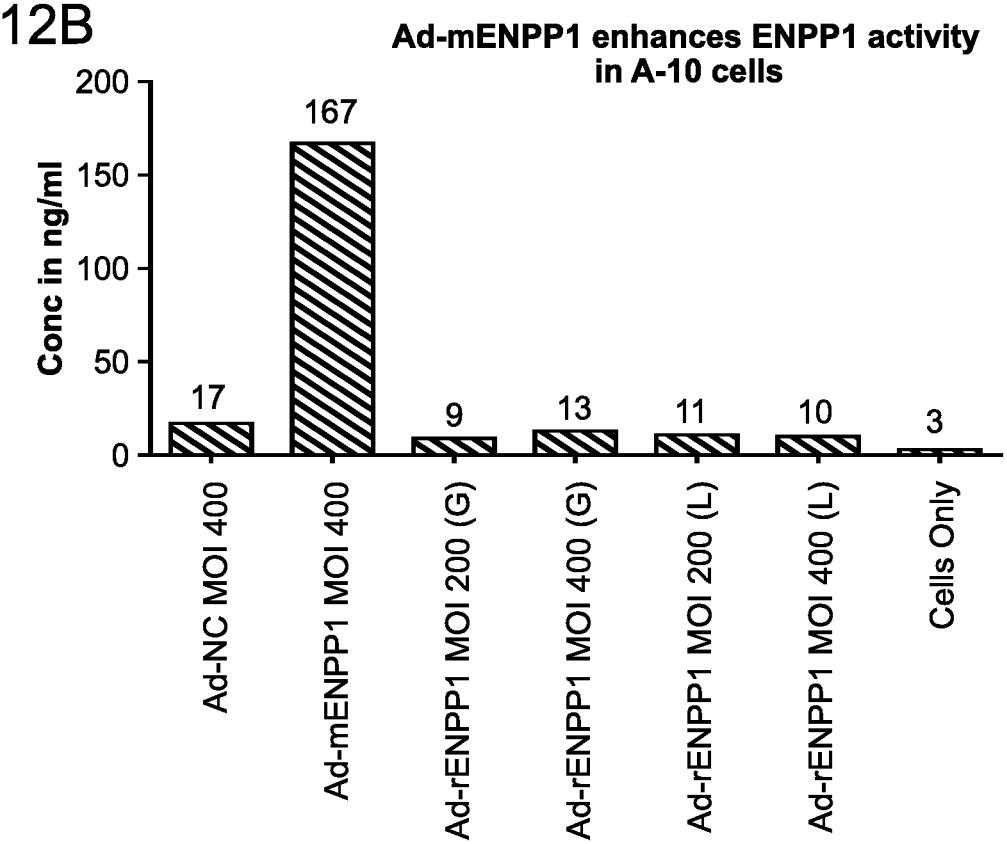

As shown in FIGS. 12A-12B, over-expression of mENPP1 rescued enzyme activity in rVSMCs and A10 cells (nondifferentiated rat VSMCs). Rat ENPP1 activity was not detected in A10 cells, but, low enzyme activity was observed in primary VSMCS transfected with Ad-rENPP1 (GeneWiz).

3E. Silencing ENPP1 Increases Proliferation in Rat VSMCs, Whereas Over-Expression of Mouse or Rat ENPP1 Inhibits Proliferation Co-transfection with Ad-ENPP1 and siRNA: Rat VSMCs (passage 3) were seeded in the wells of 96-well plate at 6000 cells/well in complete medium. After overnight culture, the cells were transfected with siRNA targets to rat ENPP1 using Lipofectamine RNAiMAX. After 4 hours incubation, siRNA was removed and the adenoviral vector Ad-rENPP1 or Ad-mENPP1 was added to the cells at multiplicities of infection (MOI) dose of 400. The plates were spun at 37° C. for 1.5 hours at 900 g and incubated at 37° C. for next 30 minutes before removing the adenoviral particles and washing with PBS. The siRNA particles were added again and left for overnight infection. Day 1 post transfection, starvation media (0.25% FBS in basal media) was added to the starvation condition, complete media was added to non-starvation condition.

Forty eight hours post transfection, complete media was added to starvation condition cells. Cell proliferation was evaluated at Day 4 post-transfection by [3H] thymidine uptake. [3H] thymidine was added in the last 18 hours of culture (see FIGS. 13A-13B).

In a separate experiment, forty eight hours post transfection, cells were seeded into wells of 24-well plate at 15000 cells/well in complete medium for 4 hours, followed by 48 hours starvation in 0.25% FBS, the cells were cultured in base media contains 5% FBS (lower). Cells were stained with AOPI and counted using auto cell counter 72 hours later (See FIG. 14 and Table 2) siNC (Silencer Select ENPP1 siRNA s10265 (5 nmol)) Cat #4390824, ThermoFisher Scientific siRNA Rat enpp1 (SASI_Rn01_00111206) Cat #PDSIRNA2D, Sigma.

Results are expressed as Cell number±SEM. Experiments were triplicated.

TABLE 2

| Sample ID | Viability (%) |
| --- | --- |
| siNC + AdNC | 89.35 |
| si-rENPP1 + AdNC | 85.2 |
| si-rENPP1 + AdmENPP1 | 89.25 |
| si-rENPP1 + AdrENPP1 | 85.9 |

Figure 14:
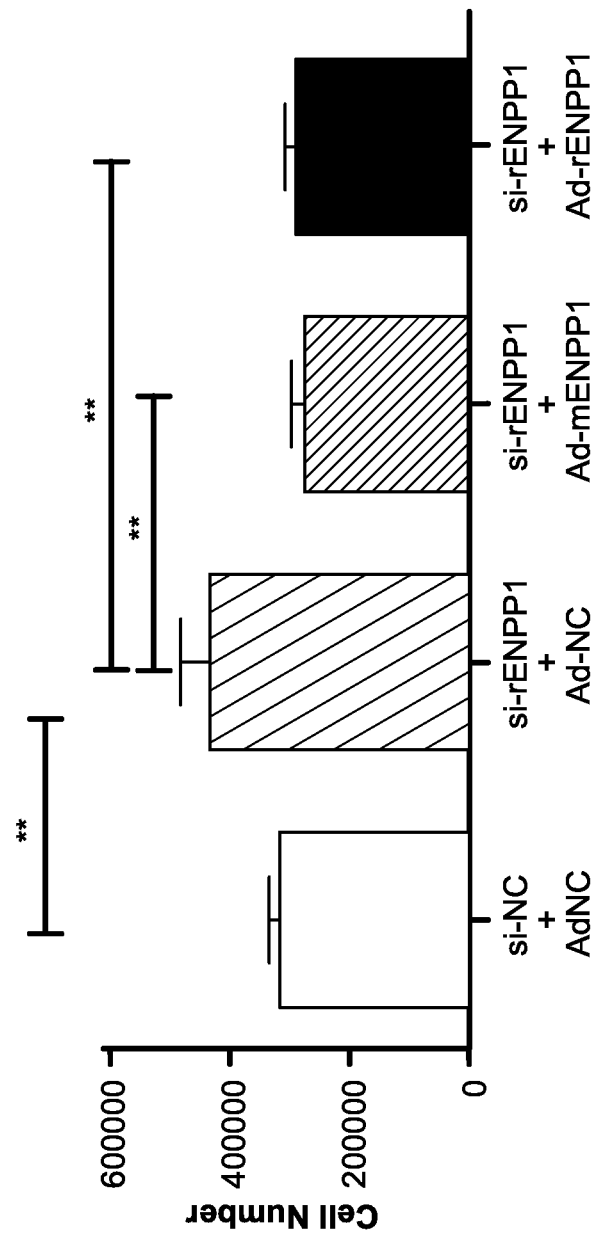
FIG. 14 depicts the effect of silencing ENPP1 and overexpression of mouse or rat ENPP1 on rat VSMCs cell growth.

As shown in FIGS. 13A-13B and FIG. 14, silencing ENPP1 increased proliferation in rat VSMCs, whereas over-expression of mouse or rat ENPP1 inhibited proliferation.

In summary, the above experiments demonstrated that silencing ENPP1 increased proliferation and cell growth of VSMCs in all tested systems. Moreover, over expression of mouse or rat ENPP1 using an Ad vector inhibited proliferation and cell growth in rat VSMCs.

Example 4

In Vitro Proof of Concept in Rat Primary VSMCs

Rat VSMCs were seeded in 35 mm dish at density 75000 cells/9.6 cm² in completed medium. After overnight culture, the cells were transfected with siRNA targets to rat ENPP1 or siRNA negative control (siNC) for overnight. The cells were then starved with base medium contains 0.25% FBS. After 24 hrs starvation, the cells were reseeded into the well of 96 well plates at 2500 cells/0.32 cm2 in CM. After 4 hrs, once the cells adhered, ATP treatments (FLAAS, Sigma) were added at 1M in final concentration. After 30 minutes, 1000 of supernatant was collected and tested via CellTiter-Glo® Luminescent Cell Viability Assay (cat #G7572, Promega) in a black/opaque plate. Also, cell titer glo with the seeded cells was performed per manufacturer's instruction. This protocol was repeated 2 hours and 24 hours post ATP treatment.

Figure 15:
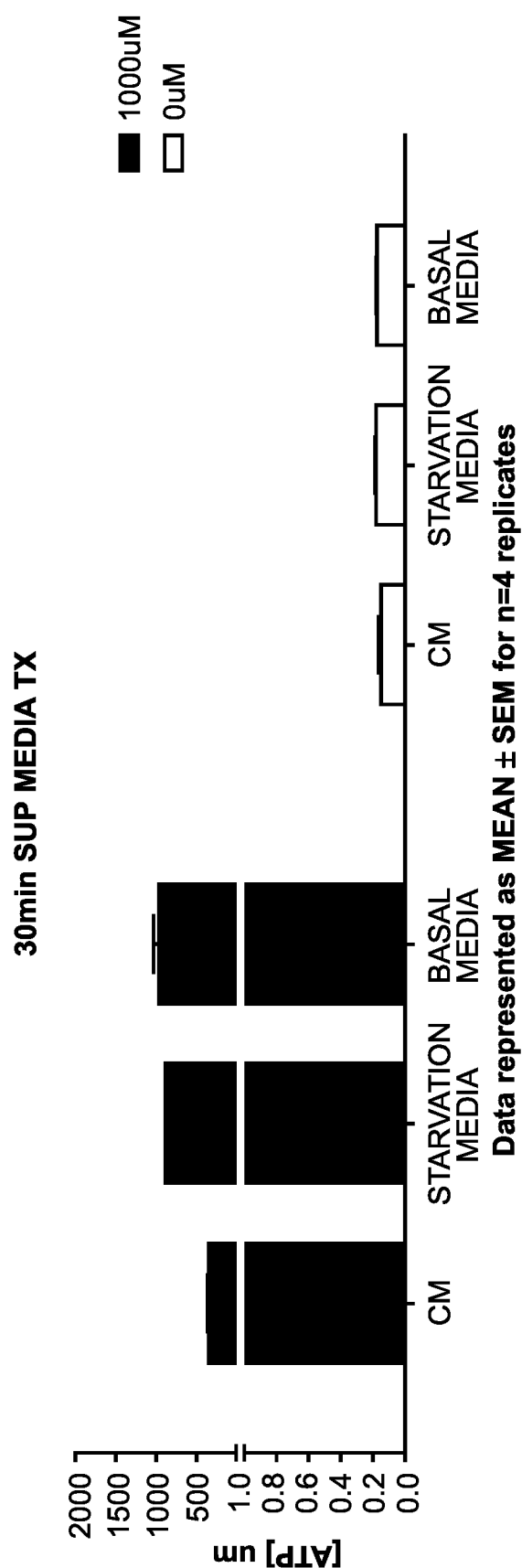
FIG. 15 shows that FBS has a negative effect on stability of ATP in cultured supernatant. CM contains 5% FBS, Starvation media contains 0.25% FBS. ATP function was reduced over 60% in CM after 30 minutes in culture at 37° C.
Figure 16:
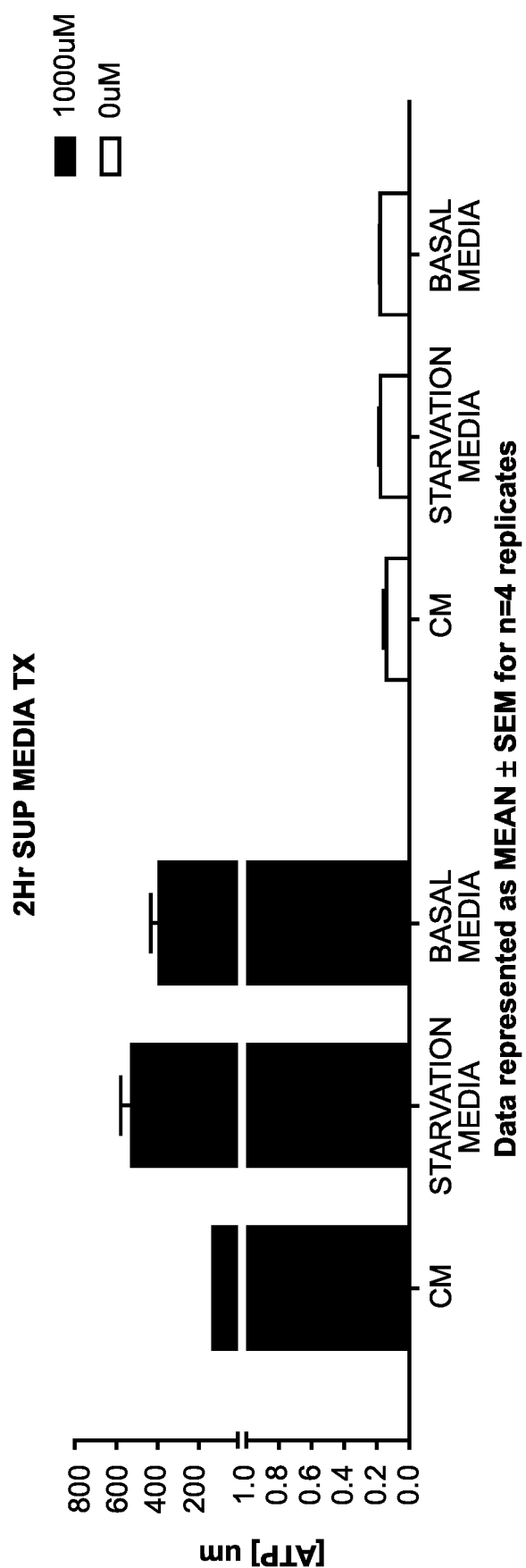
FIG. 16 shows that FBS has a negative effect on stability of ATP in cultured supernatant. CM contains 5% FBS, Starvation media contains 0.25% FBS. ATP function was reduced over 87% after 2 hours in culture at 37° C.
Figure 17:
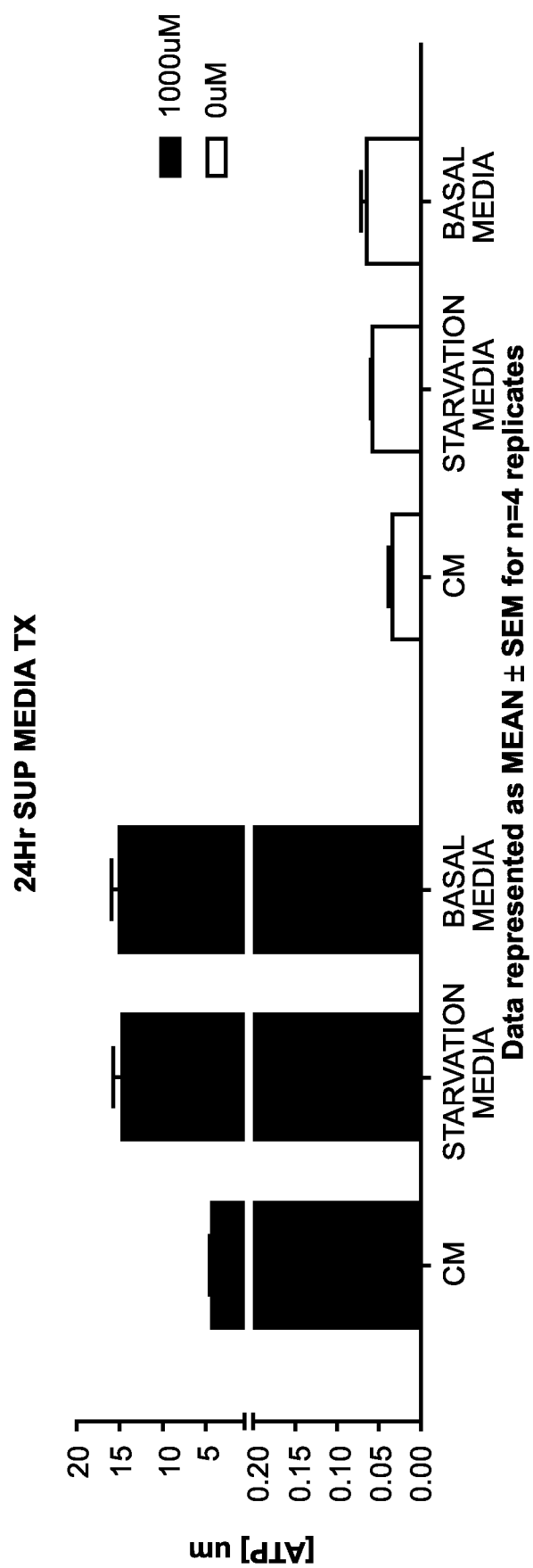
FIG. 17 shows that FBS has a negative effect on stability of ATP in cultured supernatant. CM contains 5% FBS, Starvation media contains 0.25% FBS. ATP function was almost entirely lost after 24 hours in culture at 37° C.
Figure 18B:
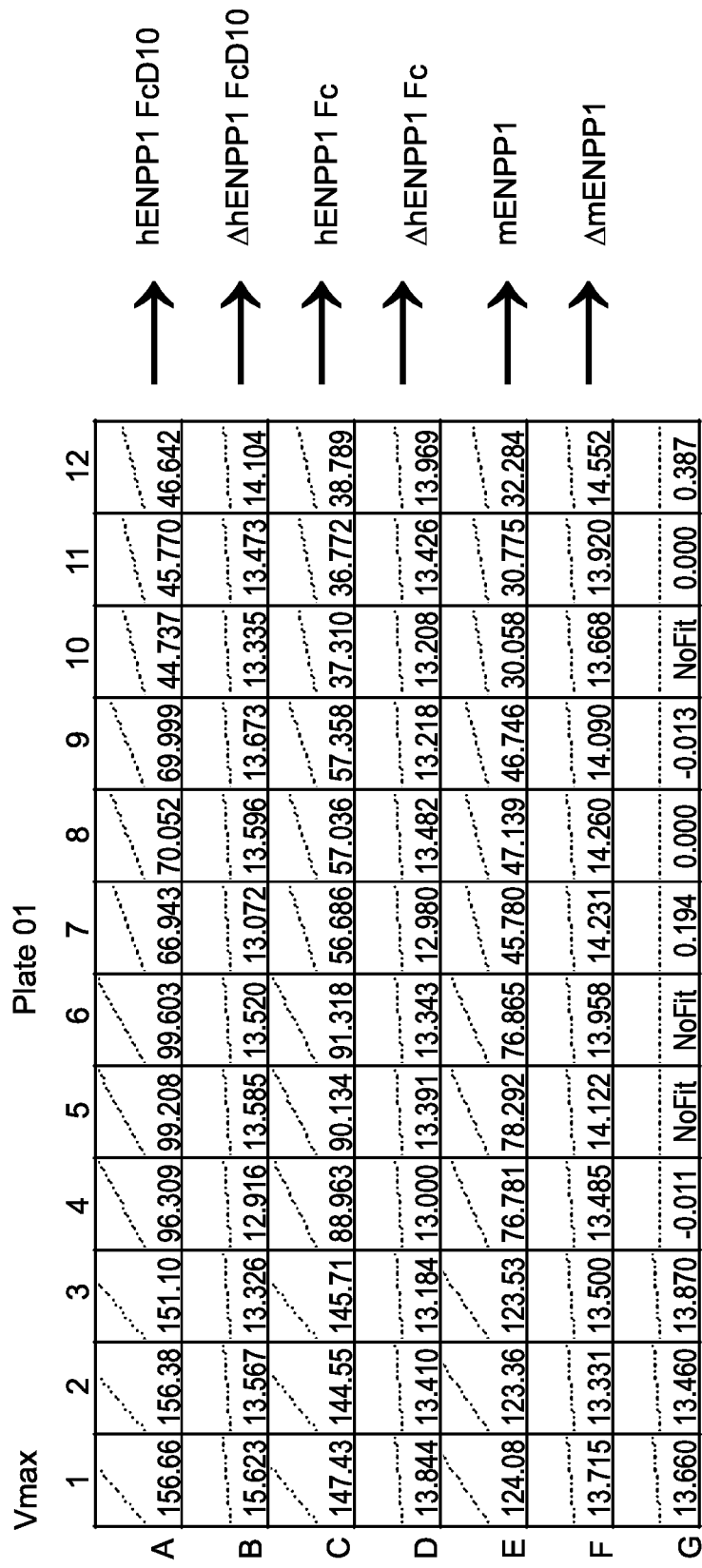

As shown in FIG. 15 (30 minute), FIG. 16 (2 hour), and FIG. 17 (24 hour), ATP is unstable in complete medium containing 5% FBS in culture at 37° C. Moreover, as shown in FIG. 18 heat denatured human/mouse ENPP1-Fc protein completely lost enzymatic activity.

In a separate experiment, rat VSMCs were seeded in the well of the 6-well plates in complete medium contains 5% FBS. After overnight culture, the cells were transfected with siRNA targets to rat ENPP1 (SASI_Rn01_00111206 Cat #PDSIRNA2D, Sigma) or siRNA negative control (Silencer Select ENPP1 siRNA s10265 (5 nmol) Cat #4390824, ThermoFisher Scientific) for overnight. The cells were then starved with base medium contains 0.25% FBS. After 24 hrs starvation, the cells were reseeded into the well of 96 well plates and cultured with completed medium contains 5% FBS in presence with 300 μM ATP and mENPP1-Fc protein (FIG. 19A), hENPP1-Fc (FIG. 19B), or hENPP1-Fc-D10 (FIG. 19C) protein, at the indicated concentration. The cultured medium was replaced daily. Proliferation was measured at day 3 using MicroBeta 3H-Thymidine incorporation. Thymidine was added in the last 18 hours.

Figure 19A:
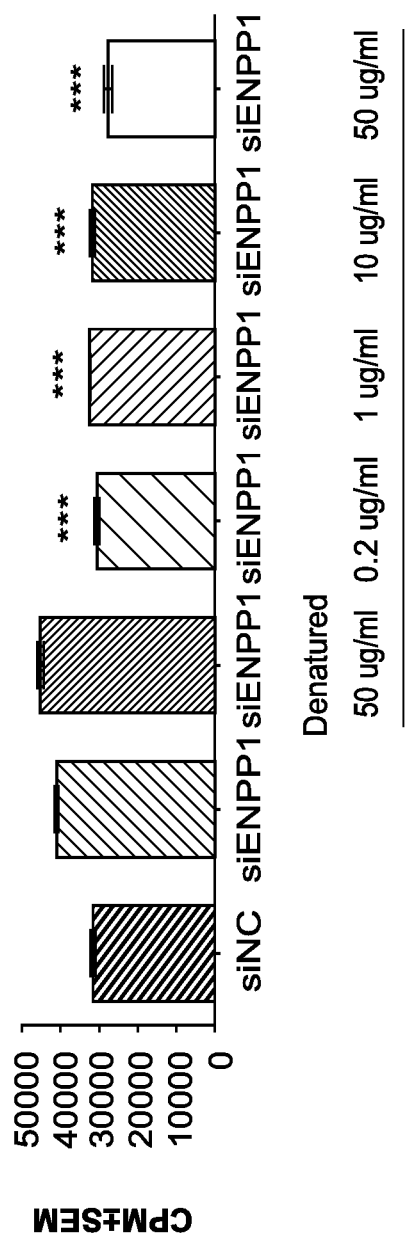
Figure 19B:
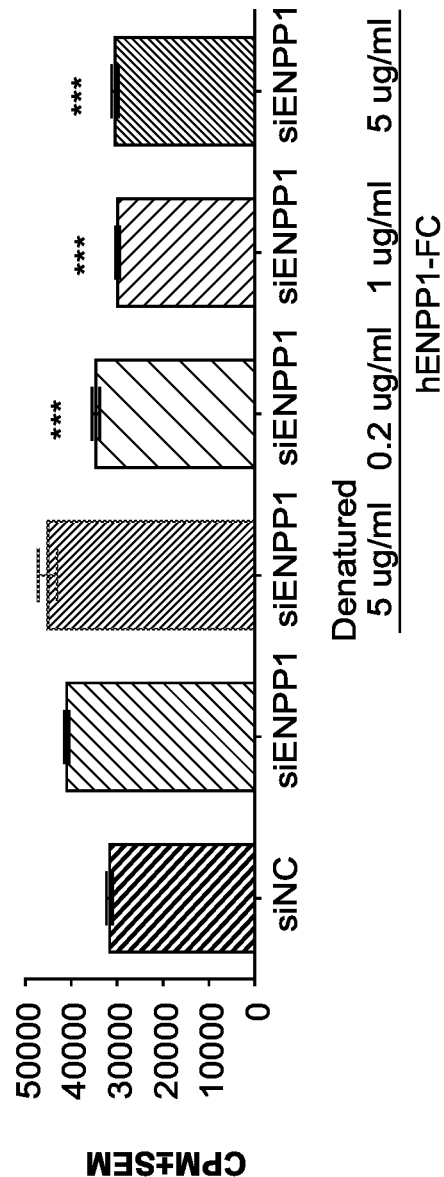

As shown in FIGS. 19A-C, treatment with any of the ENPP1 proteins (mENPP1-Fc (FIG. 19A), hENPP1-Fc (FIG. 19B), and hENPP1-Fc-D10 (FIG. 19C)) inhibited proliferation on rat primary VSMCs. Heat denatured ENPP1 had no effect on proliferation of rat VSMCs.

Example 5

Human Induced Pluripotent Stem Cell (hiPSC)-Derived Vascular Smooth Muscle Cells (iVSMCs)

The following experiments were conducted using human induced pluripotent stem cell (hiPSC)-derived vascular smooth muscle cells (iVSMCs).

5A. ENPP1 Expression

Human iPSC derived VSMCs (donors BJ, BLS) and human primary VSMCs (donors 1, 3, and 6) were cultured in T75 flasks in iVSMC cultured medium and complete medium, respectively. Cells were harvested at 80% confluence, total RNA was isolated from cells using a Qiagen Rneasy Mini kit (cat #74106) and QIAshredder (cat #79656, QIAGEN, Valencia, Calif.) as per manufacturer's instructions. The isolated RNA was quantified using a Nanodrop2000 (Thermoscientific) and reverse transcribed to cDNA using High-Capacity cDNA Reverse Transcription Kit (Cat #4368814; ThermoFisher Scientific). The resulting cDNA is amplified using the TaqMan Universal PCR Master Mix and detected by real-time PCR using QuantStudio™ 7 Flex System. TaqMan probes for human ENPP1, Hs01054038_m1 and housekeeping gene, glyceraldehyde-3-phosphate dehydrogenase (GAPDH) Hs99999905_m1 were obtained from ThermoFisher Scientific. Target gene expression level was normalized by GAPDH level in each sample and Relative expression level was calculated using 2-ΔΔ Ct method (FIG. 20A).

Western Blot Analysis: The VSMCs were detached, washed in PBS and the cell lysates were prepared in lysis buffer containing 1% each of protease inhibitor (p8340; Sigma), Phosphatase Inhibitor Cocktail 3 (cat #P0044; Sigma) and Phosphatase Inhibitor Cocktail 2 (cat #P5726;

Sigma). The cell lysate was quantified and denatured, then equal amounts of the protein were loaded on 4-12% Bis polyacrylamide gels. The proteins level was measured once the gel was electrophoretically transferred to nitrocellulose membrane using iBlot® 2 Dry Blotting System. The membranes were blocked for 1 h in blocking buffer (Licor TBS blocking buffer (P/N 927-50000) and incubated with Rabbit pAb to human ENPP1 (PA527905 by Thermo Fischer Scientific) at 1:500 and GAPDH (14C10) Rabbit anti GAPDH mAB by Cell Signalling Technology (cat #2118L) at 1:1000 in blocking buffer containing 0.2% Tween20 overnight at 4° C., followed by a Donkey-anti-Rabbit Antibody conjugated with the fluorescent dye IRDye® 800CW (cat #926-32213; LICOR) or Donkey-anti-Rabbit Antibody conjugated with the fluorescent dye IRDye® 680RD (cat #926-68073; LICOR) for 1 h at room temperature, respectively. The signals were detected using the Odyssey CLx Imaging System (LI-COR Biosciences). Signals of ENPP1 protein were normalized with level of endogenous protein GAPDH in each sample. The relative protein expression for the human primary iVSMC donors and the VCMC donors are depicted in FIGS. 20B and 20C, respectively.

Figure 20B:
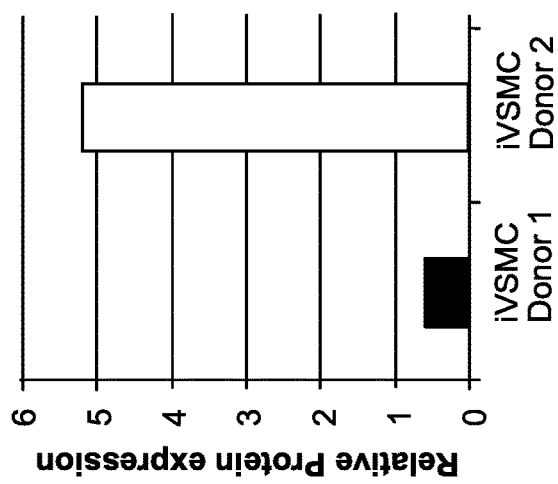
FIGS. 20A-20C depict ENPP1 expression by human primary VSMCs and human induced pluripotent stem cell (hiPSC)-derived vascular smooth muscle cells (iVSMCs), as assessed by qRT-PCR (FIG. 20A) and Western Blot (FIGS. 20B-C).
Figure 20A:
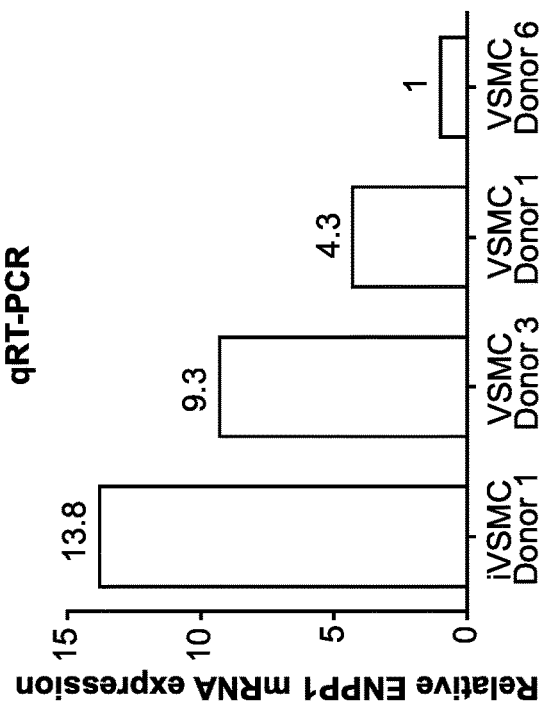
Figure 20C:
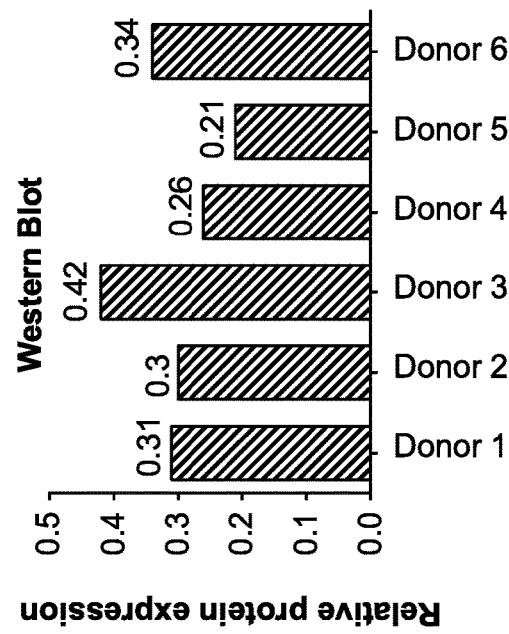

As shown in FIGS. 20A-B, human primary iVSMCs expressed a high level of ENPP1.

5B. Effect of Silencing ENPP1 on Growth of Human iVSMCs.

Human iPSC differentiated VSMCs (iVSMCs) (p2) were seeded into the wells of 6-well plate and transfected with ENPP1 siRNA or negative control siRNAs, either consisting of a scrambled nucleotide sequence or directed to actin. After 48 hours transfection, the cells were detached, stained with AOPI and counted in auto cell counter Cellometer 2000.

Figure 21:
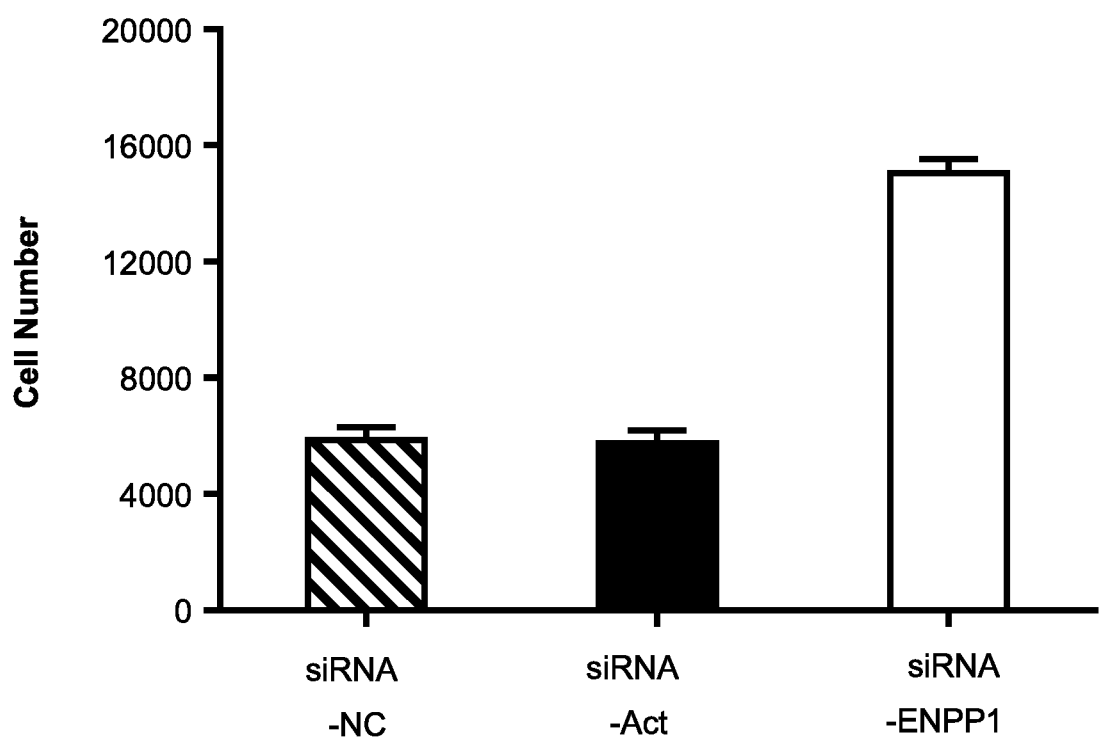
FIG. 21 depicts the effect of silencing ENPP1 by siRNA on the growth of human induced pluripotent stem cell (hiPSC)-derived vascular smooth muscle cells (iVSMCs).

As shown in FIG. 21, silencing ENPP1 by siRNA increased the growth of human iVSMCs as compared to both of the negative controls.

5C. In vitro Proof of Concept Human iVSMCs

Additional experiments were conducted using human induced pluripotent stem cell (hiPSC)-derived vascular smooth muscle cells (iVSMCs) to assess the effect of murine and human ENPP1 protein on proliferation. The following ENPP1 proteins were used: mENPP1-mG1FC: ZLC022, hENPP1-FC: 105-FC, and hENPP1-FC-D10: 105-FC-D10.

The human iPSC derived VSMCs were seeded at 3500 cells/0.32 cm2 in collagen 1 coated 60 mm dishes in SmGM-2 Smooth Muscle Growth Medium-2 (Cat #CC-3182, Lonza). After overnight culture, the cells were transfected with siRNA targets to human ENPP1 using Lipofectamine RNAiMAX (cat #13778500, ThermoFisher Scientific) for overnight. Following 48 hours starvation with 0.25% FBS, cells were stained with AOPI and counted with auto cell counter, Cellometer 2000. The effect of ENPP1-Fc protein on proliferation in VSMCs was measured using 3H thymine incorporation. Cells were reseeded in the wells of a 96 well plate that was pre-coated with collagen 1 in completed medium presence with 300 µM ATP in addition to absence or presence of varied concentration of mENPP1-Fc, hENPP1-Fc, or hENPP1-FC-D10 protein for 3 days. Culture medium was replaced daily. 3H thymine was added in the last 18 hours of culture. Results presents as mean±SEM of four wells (n=4). A similar pattern was confirmed in three independent assays. The statistical analysis was performed by student T test.

Figure 22A:
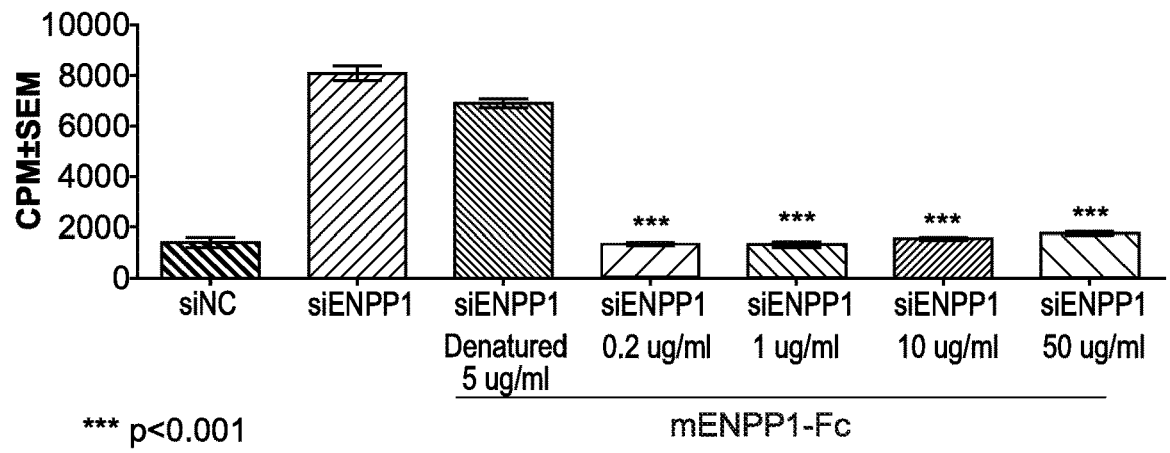
FIGS. 22A-22C depict the effect of murine (FIG. 22A) and human ENPP1-Fc (FIGS. 22B-22C) protein on the proliferation of human induced pluripotent stem cell (hiPSC)-derived vascular smooth muscle cells (iVSMCs).
Figure 22B:
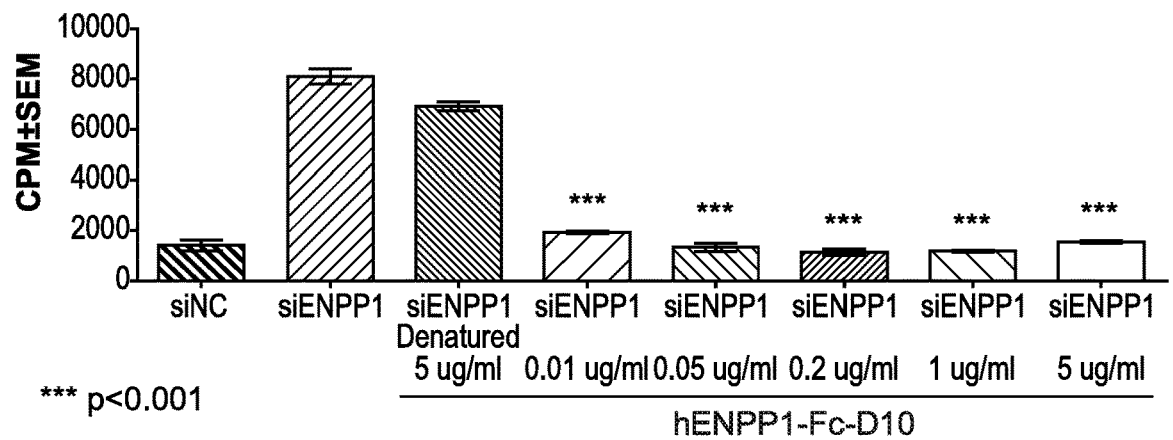
Figure 22C:
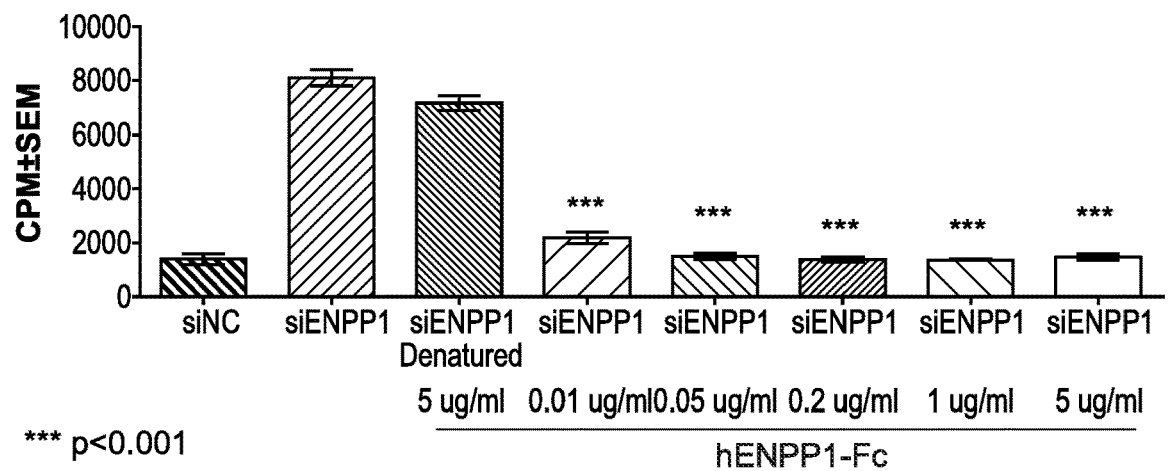

As shown in FIGS. 22A-C, all of the ENPP1 proteins significantly inhibited proliferation in human iVSMCs at all concentrations tested.

5D. PPi Assay Using Human iVSMCs

PPi is produced in an ENPP1 enzyme catalyzed reaction. PPi level was measured in culture supernatant using a radioactive assay. In order to avoid precipitation of magnesium pyrophosphate, assay components were divided into stock solutions. First, a master mix was prepared with 49.6 mM Trizma Acetate (cat #93337; Sigma-Fluka), 4.5 mM Magnesium acetate tetrahydrate (cat #63049; Sigma-Fluka); 3.5 µM NAPD-Na2 (cat #10128058001; Roche); 16.2 µM D-Glucose-1,6-diphosphate (cat #G6893; Sigma); 6.6 µM Uridine-5-Diphosphoglucose (cat #U4625; Sigma); 0.002 U/µl Phosphoglucomutase (cat #P3397; Sigma); 0.003 U/µl Glucose-6-phosphate dehydrogenase (cat #10165875001; Roche) and MilliQ water. Add 0.00118 U/µl Uridine 5'-diphosphoglucose pyrophosphorylase (cat #U8501; Sigma) and 0.0002 µCi/µl Uridine diphospho-D-[6-3H] glucose (cat #NET1163; Perkin Elmer) to the master mix right before adding to the samples, and 25 µl of sample was added into 115 µl master mix. After 30 minutes incubation at 37° C., 200 µl of cold 3% activated charcoal (cat #C5510; Sigma) was added and incubated 30 min at 4° C. with vortexing every 10 min intervals. The contents of the tube was transferred into a 96 well filter plate (cat #8130; Pall Corporation). The reaction mix was filtered and 80 µl of supernatant was transferred to Iso beta plates (cat #6005040; Perkin Elmer) keeping the same plate position using 960 LTS Wide-orifice tips in 10 racks, presterilized. Add 120 µl of scintillation liquid Ultima Gold (cat #6013321; Perkin Elmer) and mixed well. The plated were incubated for 1 hour and then read via a micro beta counter.

Figure 23:
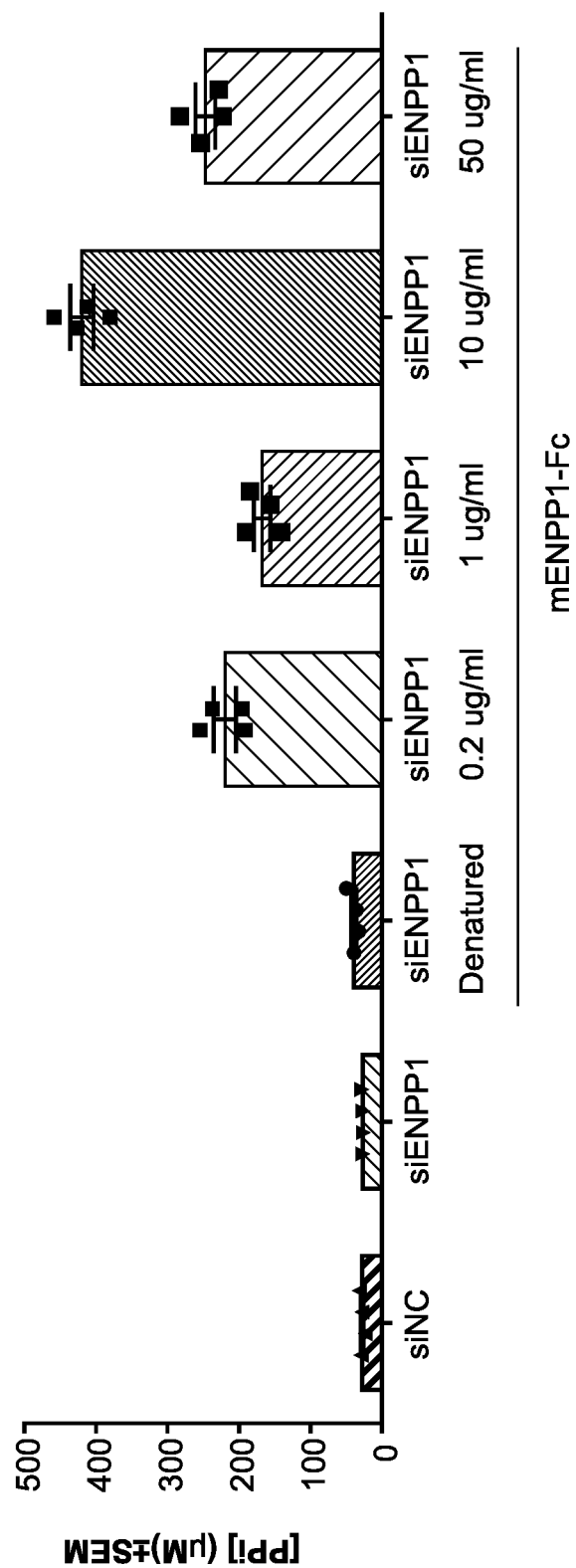
FIG. 23 depicts PPi levels in the supernatant, as assessed by a PPi assay using human iVSMCs.

As shown in FIG. 23, PPi was detected in the supernatant collected from human iVSMCs treated with mENPP1-Fc. Similar results were obtained using both hENPP1-Fc and hENPP1-Fc-D10.

In summary, all three ENPP1 proteins (mENPP1-Fc, hENPP1-Fc, and hENPP1-Fc-D10) significantly inhibited proliferation in human iVSMCs that silenced ENPP1. Heat denatured ENPP1 had no effect on proliferation of iVSMCs. The inhibition was more potent in human iVSMC than it was in rat VSMCs.

5E. Effect of Bisphosphonate on Proliferation of human iVSMCs

The effect of Bisphosphonate on proliferation in human iVSMCs that silenced ENPP1 was evaluated using 3H thymine incorporation. The human iVSMCs were seeded at 3500 cells/0.32 cm2 in collagen 1 coated 60 mm dishes in SmGM-2 Smooth Muscle Growth Medium-2 (Cat #CC-3182, Lonza). After overnight culture, the cells were transfected with siRNA targets to human ENPP1 using Lipofectamine RNAiMAX (cat #13778500, ThermoFisher Scientific) for overnight. Following 48 hours starvation with 0.25% FBS, cells were stained with AOPI and counted with auto cell counter, Cellometer 2000. Cells were reseeded in well of 96 well plate at 2500 cells/well and cultured in complete medium in the presence and absence of Etidronate (Cat #P5248, Sigma) at indicated concentration. Cell proliferation was evaluated on day 3 by [3H] thymidine uptake. Results are expressed as CPM±SEM. Experiments were triplicated.

Figure 24:
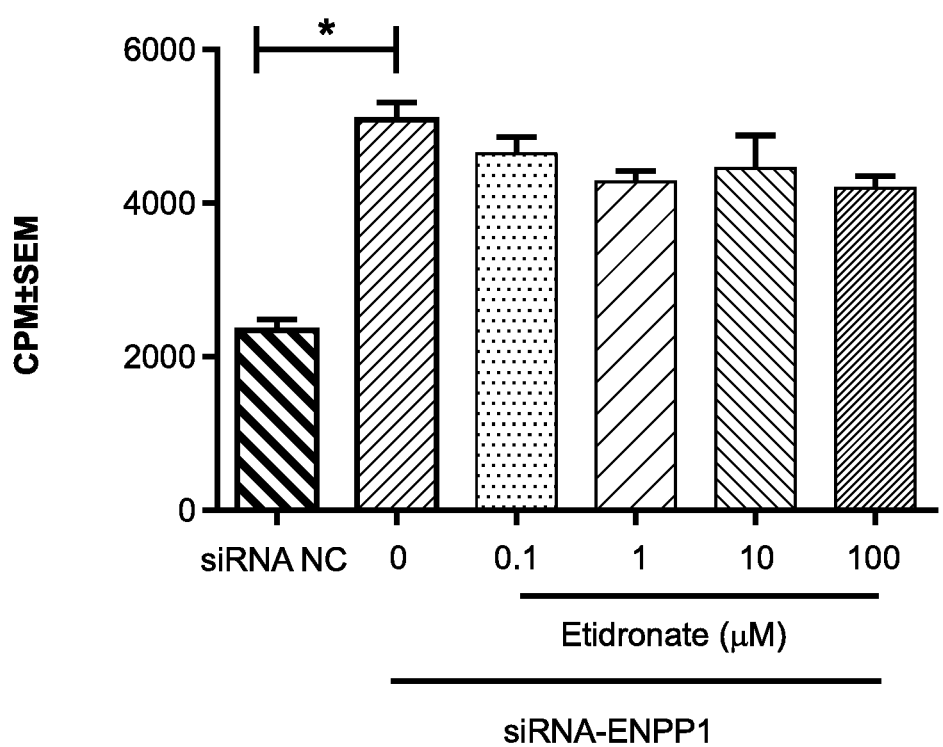
FIG. 24 depicts the effect of bisphosphonate on proliferation of human iVSMCs.

As shown in FIG. 24, bisphosphonate did not appear to inhibit proliferation in human iVSMCs.

Example 6

In Vivo Murine Carotid Artery Ligation Studies

Carotid artery ligation in the mouse is a common model for investigating the response of the vasculature to mechanical injury. Damage to the vessel induces an inflammatory response and endothelial activation, resulting in smooth muscle cell proliferation and narrowing of the lumen of the vessel. Accordingly, carotid artery ligation in the tip-toe-walking (ttw) mouse, which contains a mutation in Enpp1 and serves as a model of generalized arterial calcification of infancy (GACI), was used to investigate the role of Enpp1 treatment on intimal hyperplasia.

Figure 25:
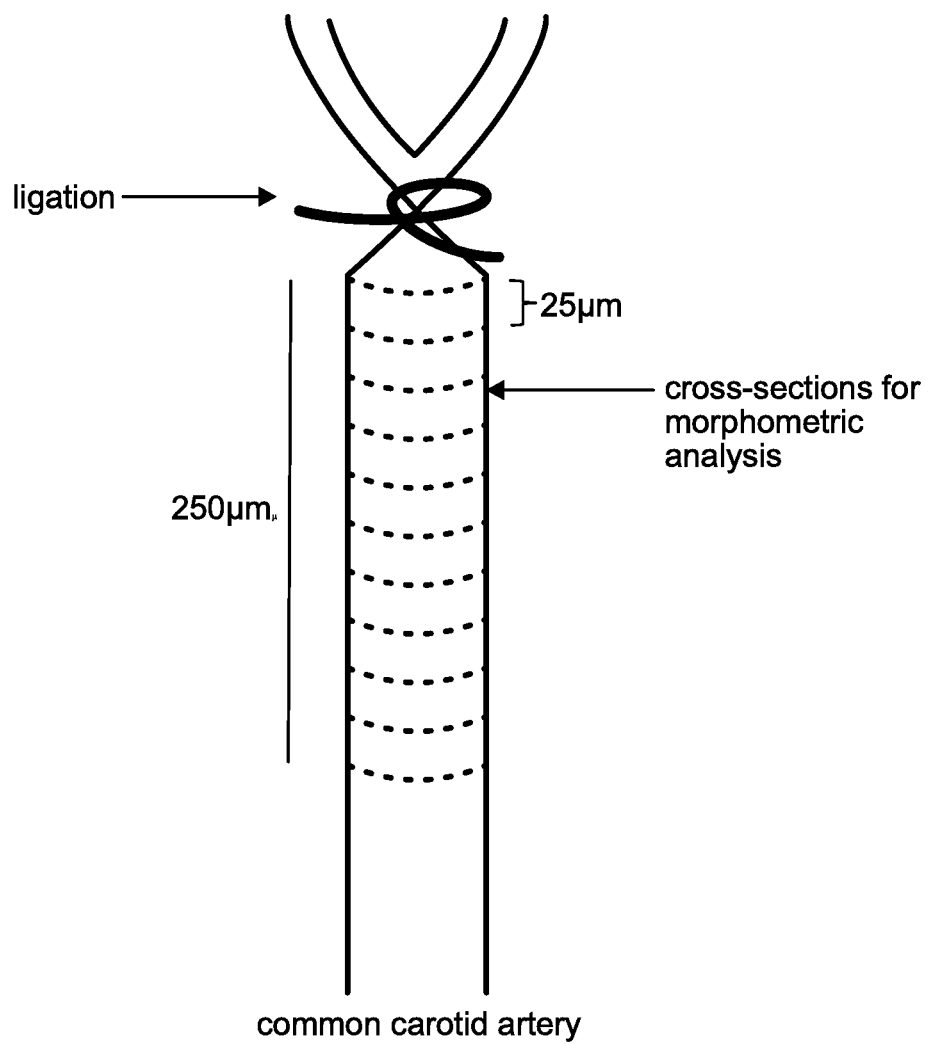
FIG. 25 is a diagram of the carotid artery ligation and sectioning for histological analysis. Five μm sections were cut spanning 250 μm from the point of ligation. Every fifth section was analyzed.

FIG. 25 shows the carotid ligation procedure. In anesthetized animals, the left carotid artery is exposed through a small incision in the neck and is ligated with a suture approximately 2 mm proximal from the carotid bifurcation. The animals are allowed to recover for 14 days, at which time the carotid arteries are harvested and fixed in 4% paraformaldehyde in PBS for sectioning and histological analysis. Serial sections of 5 µm were taken spanning 250 µm from the ligation. Every fifth section was analyzed with Von Gieson's stain and morphometric analysis was performed using Image J software.

To determine the effect of Enpp1 on intimal hyperplasia, 6 to 7-week old homozygous ttw/ttw mice were treated with either vehicle or recombinant human Enpp1 (rhEnpp 1) at 10 mg/kg by subcutaneous (SC) injection every other day. The mice were treated for 7 days prior to carotid ligation, and treatment continued for 14 days post-surgery when the carotid arteries were harvested for analysis.

Figure 26:
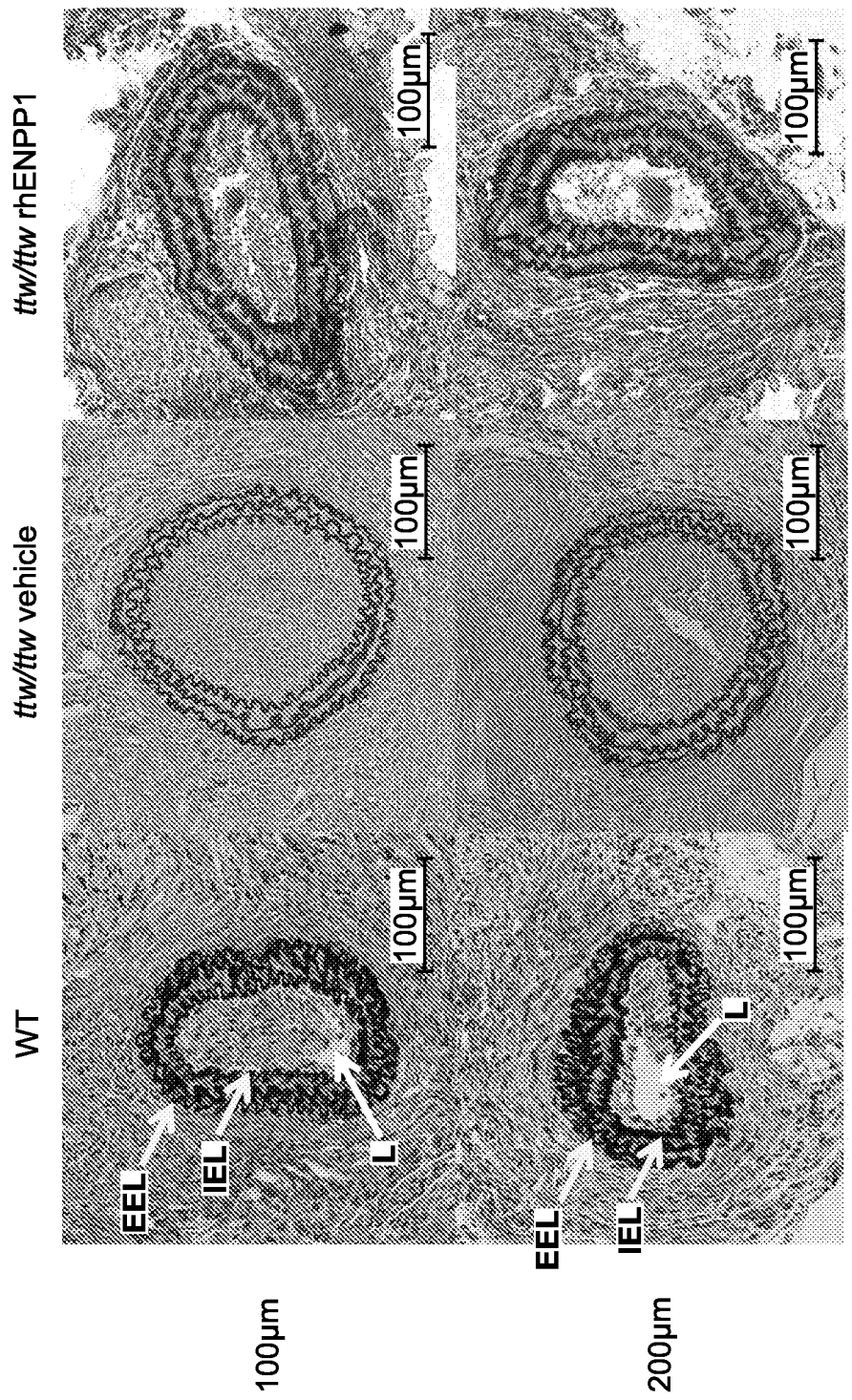
FIG. 26 is a histological analysis (Von Gieson's stain) of sections either 100 (upper) or 200 (lower) μm from point of ligation from wild-type (WT), ttw/ttw, vehicle-treated ttw/ttw or rhENPP1-treated ttw/ttw/mice from left to right, respectively. The internal elastic lamina (IEL), external elastic lamina (EEL) and lumen (L) are indicated by arrows. The scale bar represents 100 μm.

The histological analysis is shown in FIG. 26. Representative stained sections from either 100 µm (top) or 200 µm (bottom) from the ligation in WT and vehicle or rhEnpp1-treated ttw/ttw are shown from left to right, respectively. Von Gieson's solution stains elastic collagen fibers and distinguishes the internal (IEL) and external elastic lamina (EEL) from the lumen of the vessel (L). In the WT mice, the carotid ligation caused intimal hyperplasia resulting in narrowing of the lumen, with more severe narrowing closer to the ligature (100 µm) and less severe occlusion further away (200 µm). In contrast, in the ttw/ttw mice the degree of intimal hyperplasia appeared to be increased, as the lumen at 200 µm is almost completely occluded. The ttw/ttw mice treated with rhENPP1 showed much less intimal hyperplasia than those treated with vehicle, approaching the degree seen in WT animals. This suggests that the presence of Enpp1 prior to and after the carotid ligation protected against intimal hyperplasia.

FIGS. 27A-C show morphometric quantitation of the results. Measurement of the circumference of the external and internal elastic lamina and the luminal border allows quantitation of the medial (M) and intimal (I) areas. The medial area, between the external and internal lamina, remained constant (FIG. 27A). The intimal area within the lumen showed a statistically-significant increase in ttw/ttw and vehicle-treated ttw/ttw mice relative to WT mice (FIG. 27B). The rhENPP1-treated ttw/ttw mice were similar to WT mice in both the intimal area and the I/M ratio, with the results again being statistically significant (FIG. 27C). These results support the protective effect of rhENPPP1 when administered prior to carotid ligation.

In order to determine if ENPP1 could have a therapeutic effect if given after the carotid ligation, 6 to 7-week old ttw/ttw mice were subjected to carotid ligation and allowed to recover. rhEnpp1 treatment (10 mg/kg SC every other day) was initiated 7 days following carotid ligation and continued until the carotid arteries were harvested at 14 days post-ligation.

Figure 28A:
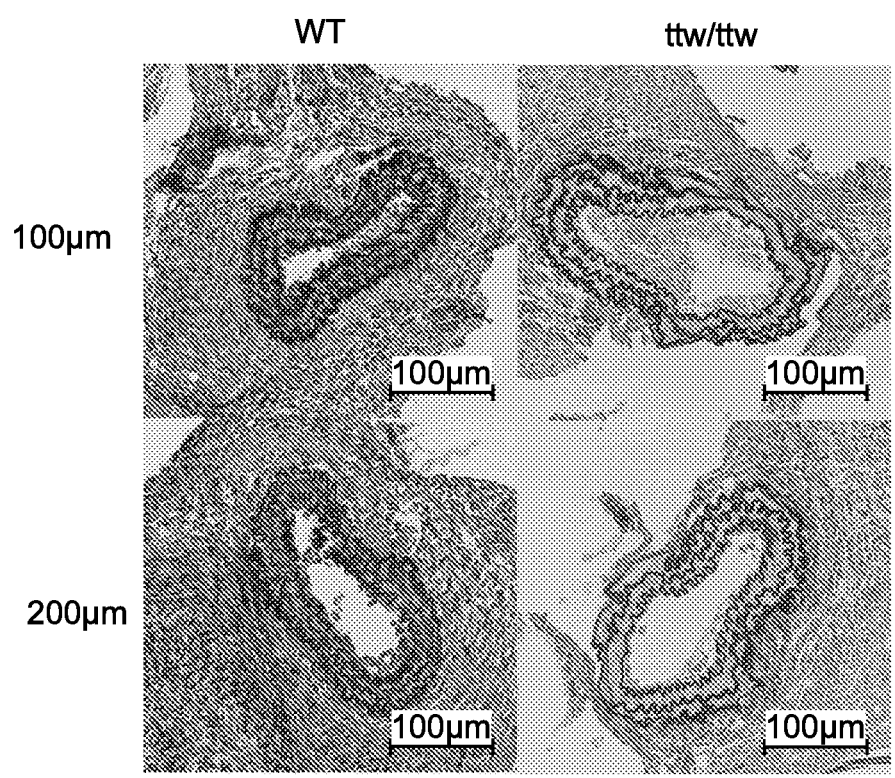
FIGS. 28A-28B show the effect of therapeutic Enpp 1 treatment on intimal hyperplasia in ttw/ttw mouse started 7 days after carotid ligation.
Figure 28B:
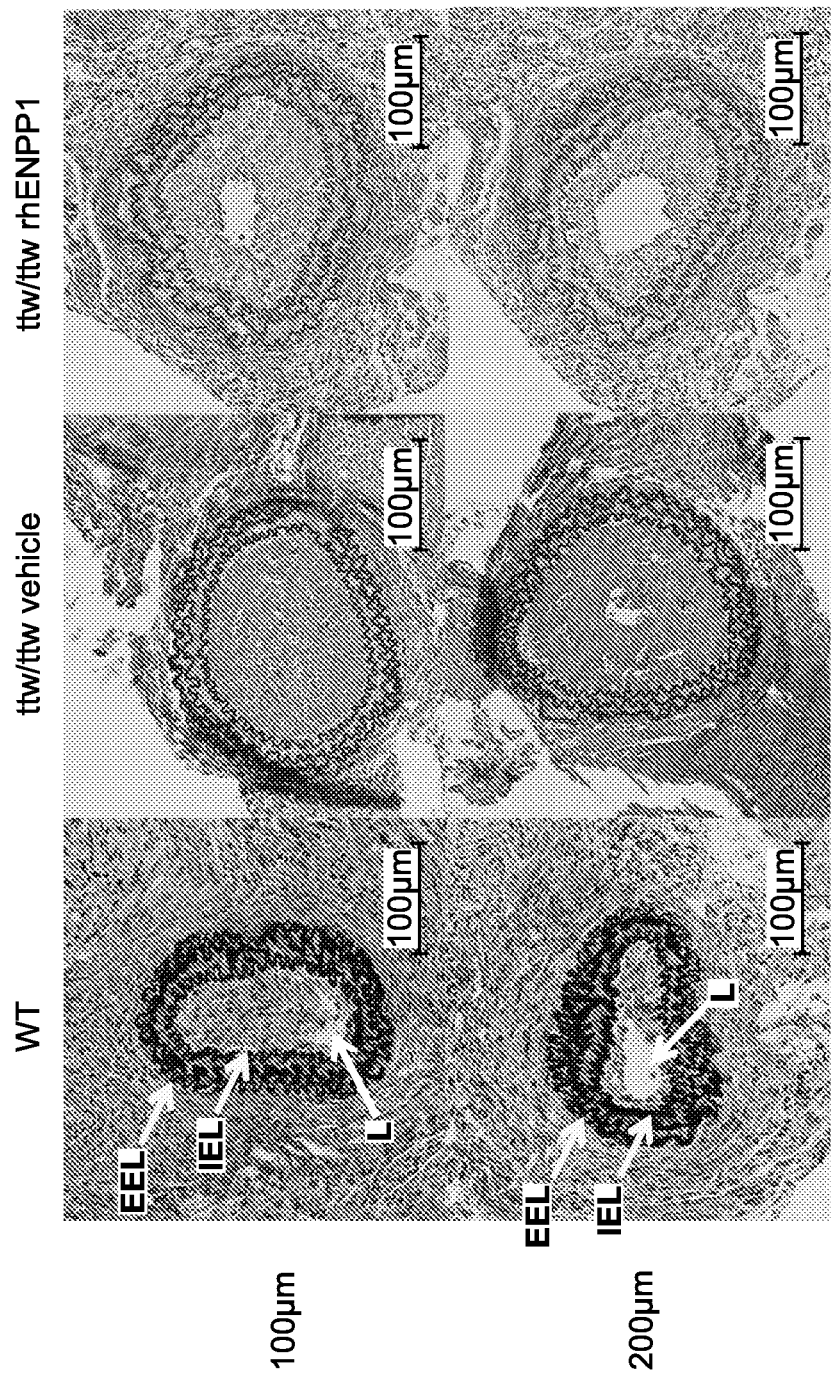

FIG. 28A shows the degree of intimal hyperplasia present at 100 and 200 µm 7 days post carotid ligation, prior to the initiation of ENPP1 treatment. Histological assessment of the therapeutic effect of rhENPP1 when initiated at 7 days post ligation is shown in FIG. 28B, with representative sections at 100 µm (top) and 200 µm (bottom) from the ligation in vehicle-treated (left) and rhENPP1-treated (right) ttw/ttw mice presented. Despite the beginning of some intimal hyperplasia in the untreated animals at 7 days post ligation (FIG. 28A), treatment with rhENPP1 beginning at this point still showed benefit as the degree of luminal occlusion at both 100 and 200 µm was less than in the vehicle-treated animals 14 days post ligation.

FIG. 29 (A-C) shows the morphometric quantitation of the data. The medial area, between the external and internal lamina, remained constant. The vehicle-treated ttw/ttw mice and rhENPP1-treated ttw/ttw mice had similar intimal area, both showed significant more proliferated intimal area than WT mice (p<0.01 and p<0.05, respectively). The I/M ratio of vehicle-treated ttw/ttw mice was increased compared to WT mice, with the results again being statistically significant. However, the I/M ratio of rhENPP1-treated ttw/ttw mice was between the levels of WT and vehicle-treated ttw/ttw mice, not significantly different compared to WT and vehicle-treated ttw/ttw mice, indicating a decelerating effect of rhENPP1 on already started intimal proliferation.

In summary, in response to carotid artery ligation for two weeks, vehicle treated ttw/ttw mice showed accelerated neointimal hyperplasia. In contrast, ENPP1-Fc treated carotid ligated ttw/ttw mice displayed a significant reduction in intimal proliferation, comparable to the proliferation level of ligated WT mice. The results demonstrate that subcutaneous administration of recombinant ENPP1-Fc fusion protein prevents intimal hyperplasia in an animal model of GACI. This finding suggests that ENPP1 enzyme replacement is a potential therapeutic approach for treating intimal hyperplasia in GACI patients.

```
SUMMARY OF SEQUENCE LISTING
amino acid sequence of wild-type NPP1 protein
                                                                SEQ ID NO: 1
MERDGCAGGGSRGGEGGRAPREGPAGNGRDRGRSHAAEAPGDPQAAASLLAPMDVGE

EPLEKAARARTAKDPNTYKVLSLVLSVCVLTTILGCIFGLKPSCAKEVKSCKGRCFERTF

GNCRCDAACVELGNCCLDYQETCIEPEHIWTCNKFRCGEKRLTRSLCACSDDCKDKGD

CCINYSSVCQGEKSWVEEPCESINEPQCPAGFETPPTLLFSLDGFRAEYLHTWGGLLPVI

SKLKKCGTYTKNMRPVYPTKTFPNHYSIVTGLYPESHGIIDNKMYDPKMNASFSLKSKE

KFNPEWYKGEPIWVTAKYQGLKSGTFFWPGSDVEINGIFPDIYKMYNGSVPFEERILAVL

QWLQLPKDERPHFYTLYLEEPDSSGHSYGPVSSEVIKALQRVDGMVGMLMDGLKELNL
```

-continued

HRCLNLILISDHGMEQGSCKKYIYLNKYLGDVKNIKVIYGPAARLRPSDVPDKYYSFNYE

GIARNLSCREPNQHFKPYLKHFLPKRLHFAKSDRIEPLTFYLDPQWQLALNPSERKYCGS

GFHGSDNVFSNMQALFVGYGPGFKHGIEADTFENIEVYNLMCDLLNLTPAPNNGTHGSL

NHLLKNPVYTPKHPKEVHPLVQCPFTRNPRDNLGCSCNPSILPIEDFQTQFNLTVAEEKIIK

HETLPYGRPRVLQKENTICLLSQHQFMSGYSQDILMPLWTSYTVDRNDSFSTEDFSNCLY

QDFRIPLSPVHKCSFYKNNTKVSYGFLSPPQLNKNSSGIYSEALLTTNIVPMYQSFQVIWR

YFHDTLLRKYAEERNGVNVVSGPVFDFDYDGRCDSLENLRQKRRVIRNQEILIPTHFFIVL

TSCKDTSQTPLHCENLDTLAFILPHRTDNSESCVHGKHDSSWVEELLMLHRARITDVEHI

TGLSFYQQRKEPVSDILKLKTHLPTFSQED amino acid sequence of sNPP1 that contains cysteine-rich
region, catalytic region and c-terminal region                                                    SEQ ID NO: 2

PSCAKEVKSCKGRCFERTFGNCRCDAACVELGNCCLDYQETCIEPEHIWTCNKFRCGEK

RLTRSLCACSDDCKDKGDCCINYSSVCQGEKSWVEEPCESINEPQCPAGFETPPTLLFSL

DGFRAEYLHTWGGLLPVISKLKKCGTYTKNMRPVYPTKTFPNHYSIVTGLYPESHGIIDN

KMYDPKMNASFSLKSKEKFNPEWYKGEPIWVTAKYQGLKSGTFFWPGSDVEINGIFPDI

YKMYNGSVPFEERILAVLQWLQLPKDERPHFYTLYLEEPDSSGHSYGPVSSEVIKALQR

VDGMVGMLMDGLKELNLHRCLNLILISDHGIVIEQGSCKKYIYLNKYLGDVKNIKVIYGP

AARLRPSDVPDKYYSFNYEGIARNLSCREPNQHFKPYLKHFLPKRLHFAKSDRIEPLTFY

LDPQWQLALNPSERKYCGSGFHGSDNVFSNMQALFVGYGPGFKHGIEADTFENIEVYN

LMCDLLNLTPAPNNGTHGSLNHLLKNPVYTPKHPKEVHPLVQCPFTRNPRDNLGCSCNP

SILPIEDFQTQFNLTVAEEKIIKHETLPYGRPRVLQKENTICLLSQHQFMSGYSQDILMPL

WTSYTVDRNDSFSTEDFSNCLYQDFRIPLSPVHKCSFYKNNTKVSYGFLSPPQLNKNSSG

IYSEALLTTNIVPMYQSFQVIWRYFHDTLLRKYAEERNGVNVVSGPVFDFDYDGRCDSL

ENLRQKRRVIRNQEILIPTHFFIVLTSCKDTSQTPLHCENLDTLAFILPHRTDNSESCVHGK

HDSSWVEELLMLHRARITDVEHITGLSFYQQRKEPVSDILKLKTHLPTFSQED amino acid sequence of sNPP1-Fc fusion protein                                                    SEQ ID NO: 3

PSCAKEVKSCKGRCFERTFGNCRCDAACVELGNCCLDYQETCIEPEHIWTCNKFRCGEK

RLTRSLCACSDDCKDKGDCCINYSSVCQGEKSWVEEPCESINEPQCPAGFETPPTLLFSL

DGFRAEYLHTWGGLLPVISKLKKCGTYTKNMRPVYPTKTFPNHYSIVTGLYPESHGIIDN

KMYDPKMNASFSLKSKEKFNPEWYKGEPIWVTAKYQGLKSGTFFWPGSDVEINGIFPDI

YKMYNGSVPFEERILAVLQWLQLPKDERPHFYTLYLEEPDSSGHSYGPVSSEVIKALQR

VDGMVGMLMDGLKELNLHRCLNLILISDHGMEQGSCKKYIYLNKYLGDVKNIKVIYGP

AARLRPSDVPDKYYSFNYEGIARNLSCREPNQHFKPYLKHFLPKRLHFAKSDRIEPLTFY

LDPQWQLALNPSERKYCGSGFHGSDNVFSNMQALFVGYGPGFKHGIEADTFENIEVYN

LMCDLLNLTPAPNNGTHGSLNHLLKNPVYTPKHPKEVHPLVQCPFTRNPRDNLGCSCNP

SILPIEDFQTQFNLTVAEEKIIKHETLPYGRPRVLQKENTICLLSQHQFMSGYSQDILMPL

WTSYTVDRNDSFSTEDFSNCLYQDFRIPLSPVHKCSFYKNNTKVSYGFLSPPQLNKNSSG

IYSEALLTTNIVPMYQSFQVIWRYFHDTLLRKYAEERNGVNVVSGPVFDFDYDGRCDSL

ENLRQKRRVIRNQEILIPTHFFIVLTSCKDTSQTPLHCENLDTLAFILPHRTDNSESCVHGK

<u>HDSSWVEELLMLHRARITDVEHITGLSFYQQRKEPVSDILKLKTHLPTFSQED</u><u>PKSCDKT</u>

<u>HTCPPCPAPEAAGAPSVFLFPPKPKDTLMISRTPEVTCVVVDVSHEDPEVKFNWYVDGV</u>

EVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK amino acid sequence of sNPP1-Fc-D10

SEQ ID NO: 4

PSCAKEVKSCKGRCFERTFGNCRCDAACVELGNCCLDYQETCIEPEHIWTCNKFRCGEK

RLTRSLCACSDDCKDKGDCCINYSSVCQGEKSWVEEPCESINEPQCPAGFETPPTLLFSL

DGFRAEYLHTWGGLLPVISKLKKCGTYTKNMRPVYPTKTFPNHYSIVTGLYPESHGIIDN

KMYDPKMNASFSLKSKEKFNPEWYKGEPIWVTAKYQGLKSGTFFWPGSDVEINGIFPDI

YKMYNGSVPFEERILAVLQWLQLPKDERPHFYTLYLEEPDSSGHSYGPVSSEVIKALQR

VDGMVGMLMDGLKELNLHRCLNLILISDHGMEQGSCKKYIYLNKYLGDVKNIKVIYGP

AARLRPSDVPDKYYSFNYEGIARNLSCREPNQHFKPYLKHFLPKRLHFAKSDRIEPLTFY

LDPQWQLALNPSERKYCGSGFHGSDNVFSNMQALFVGYGPGFKHGIEADTFENIEVYN

LMCDLLNLTPAPNNGTHGSLNHLLKNPVYTPKHPKEVHPLVQCPFTRNPRDNLGCSCNP

SILPIEDFQTQFNLTVAEEKIIKHETLPYGRPRVLQKENTICLLSQHQFMSGYSQDILMPL

WTSYTVDRNDSFSTEDFSNCLYQDFRIPLSPVHKCSFYKNNTKVSYGFLSPPQLNKNSSG

IYSEALLTTNIVPMYQSFQVIWRYPHDTLLRKYAEERNGVNVVSGPVFDFDYDGRCDSL

ENLRQKRRVIRNQEILIPTHFFIVLTSCKDTSQTPLHCENLDTLAFILPHRTDNSESCVHGK

HDSSWVEELLMLHRARITDVEHITGLSFYQQRKEPVSDILKLKTHLPTFSQED<u>PKSCDKT</u>

<u>HTCPPCPAPEAAGAPSVFLFPPKPKDTLMISRTPEVTCVVVDVSHEDPEVKFNWYVDGV</u>

<u>EVHNAKTKPREEQYNSTYRVVSVLTVLHqDWLNGKEYKCKVSNKALPAPIEKTISKAK</u>

<u>GQPREPQVYTLPPSREEMTKNQVSLTCLVKGFYPSDIAVEWESNGQPENNYKTTPPVLD</u>

<u>SDGSFFLYSKLTVDKSRWQQGNVFSCSVMHEALHNHYTQKSLSLSPGK</u>

DDDDDDDDDD amino acid sequences of soluble NPP1 containing amino acids from 107 to 925 of SEQ ID NO: 1

SEQ ID NO: 5

SCKGRCFERTFGNCRCDAACVELGNCCLDYQETCIEPEHIWTCNKFRCGEKRLTRSLCA

CSDDCKDKGDCCINYSSVCQGEKSWVEEPCESINEPQCPAGFETPPTLLFSLDGFRAEYL

HTWGGLLPVISKLKKCGTYTKNMRPVYPTKTFPNHYSIVTGLYPESHGIIDNKMYDPKM

NASFSLKSKEKFNPEWYKGEPIWVTAKYQGLKSGTFFWPGSDVEINGIFPDIYKMYNGS

VPFEERILAVLQWLQLPKDERPHFYTLYLEEPDSSGHSYGPVSSEVIKALQRVDGMVGML

MDGLKELNLHRCLNLILISDHGMEQGSCKKYIYLNKYLGDVKNIKVIYGPAARLRPSDV

PDKYYSFNYEGIARNLSCREPNQHFKPYLKHFLPKRLHFAKSDRIEPLTFYLDPQWQLAL

NPSERKYCGSGFHGSDNVFSNMQALFVGYGPGFKHGIEADTFENIEVYNLMCDLLNLTP

APNNGTHGSLNHLLKNPVYTPKHPKEVHPLVQCPFTRNPRDNLGCSCNPSILPIEDFQTQ

FNLTVAEEKIIKHETLPYGRPRVLQKENTICLLSQHQFMSGYSQDILMPLWTSYTVDRND

SFSTEDFSNCLYQDFRIPLSPVHKCSFYKNNTKVSYGFLSPPQLNKNSSGIYSEALLTTNIV

PMYQSFQVIWRYPHDTLLRKYAEERNGVNVVSGPVFDFDYDGRCDSLENLRQKRRVIR

NQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQED amino acid sequence of soluble NPP1 containing amino acids from 187 to 925 of SEQ ID NO: 1

-continued

SEQ ID NO: 6

EKSWVEEPCESINEPQCPAGFETPPTLLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPI

WVTAKYQGLKSGTFFWPGSDVEINGIFPDIYKMYNGSVPFEERILAVLQWLQLPKDERP

HFYTLYLEEPDSSGHSYGPVSSEVIKALQRVDGMVGMLMDGLKELNLHRCLNLILISDH

GMEQGSCKKYIYLNKYLGDVKNIKVIYGPAARLRPSDVPDKYYSFNYEGIARNLSCREP

NQHFKPYLKHFLPKRLHFAKSDRIEPLTFYLDPQWQLALNPSERKYCGSGFHGSDNVFS

NMQALFVGYGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEKIIKHETLPYGRP

RVLQKENTICLLSQHQFMSGYSQDILMPLWTSYTVDRNDSFSTEDFSNCLYQDFRIPLSP

VHKCSFYKNNTKVSYGFLSPPQLNKNSSGIYSEALLTTNIVPMYQSFQVIWRYFHDTLLR

KYAEERNGVNVVSGPVFDFDYDGRCDSLENLRQKRRVIRNQEILIPTHFFIVLTSCKDTS

QTPLHCENLDTLAFILPHRTDNSESCVHGKHDSSWVEELLMLHRARITDVEHITGLSFYQ

QRKEPVSDILKLKTHLPTFSQED amino acid sequence of Fc region of human IgG1 including hinge region

SEQ ID NO: 7

EPKSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK amino acid sequence of Fc of human IgG1 including partial hinge region

SEQ ID NO: 8

DKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPGK amino acid sequence of NPP1-Fc fusion protein [(107-925)-Fc]

SEQ ID NO: 9

SCKGRCFERTFGNCRCDAACVELGNCCLDYQETCIEPEHIWTCNKFRCGEKRLTRSLCA

CSDDCKDKGDCCINYSSVCQGEKSWVEEPCESINEPQCPAGFETPPTLLFSLDGFRAEYL

HTWGGLLPVISKLKKCGTYTKNMRPVYPTKTFPNHYSIVTGLYPESHGIIDNKMYDPKM

NASFSLKSKEKFNPEWYKGEPIWVTAKYQGLKSGTFFWPGSDVEINGIFPDIYKMYNGS

VPFEERILAVLQWLQLPKDERPHFYTLYLEEPDSSGHSYGPVSSEVIKALQRVDGMVGML

MDGLKELNLHRCLNLILISDHGMEQGSCKKYIYLNKYLGDVKNIKVIYGPAARLRPSDV

PDKYYSFNYEGIARNLSCREPNQHFKPYLKHFLPKRLHFAKSDRIEPLTFYLDPQWQLAL

NPSERKYCGSGFHGSDNVFSNMQALFVGYGPGFKHGIEADTFENIEVYNLMCDLLNLTP

APNNGTHGSLNHLLKNPVYTPKHPKEVHPLVQCPFTRNPRDNLGCSCNPSILPIEDFQTQ

FNLTVAEEKIIKHETLPYGRPRVLQKENTICLLSQHQFMSGYSQDILMPLWTSYTVDRND

SFSTEDFSNCLYQDFRIPLSPVHKCSFYKNNTKVSYGFLSPPQLNKNSSGIYSEALLTTNIV

PMYQSFQVIWRYFHDTLLRKYAEERNGVNVVSGPVFDFDYDGRCDSLENLRQKRRVIR

NQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQEDEPKSCDKTHTCPPCPAPE

LLGGPSVFLFPPKPKDTLMISRTPEVTCVVVDVSHEDPEVKFNWYVDGVEVHNAKTKPR

```
EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK
``` amino acid sequence of NPP1-Fc fusion protein [(107-925)-partial hinge Fc    SEQ ID NO: 10

```
SCKGRCFERTFGNCRCDAACVELGNCCLDYQETCIEPEHIWTCNKFRCGEKRLTRSLCA

CSDDCKDKGDCCINYSSVCQGEKSWVEEPCESINEPQCPAGFETPPTLLFSLDGFRAEYL

HTWGGLLPVISKLKKCGTYTKNMRPVYPTKTFPNHYSIVTGLYPESHGIIDNKMYDPKM

NASFSLKSKEKFNPEWYKGEPIWVTAKYQGLKSGTFFWPGSDVEINGIFPDIYKMYNGS

VPFEERILAVLQWLQLPKDERPHFYTLYLEEPDSSGHSYGPVSSEVIKALQRVDGMVGML

MDGLKELNLHRCLNLILISDHGMEQGSCKKYIYLNKYLGDVKNIKVIYGPAARLRPSDV

PDKYYSFNYEGIARNLSCREPNQHFKPYLKHFLPKRLHFAKSDRIEPLTFYLDPQWQLAL

NPSERKYCGSGFHGSDNVFSNMQALFVGYGPGFKHGIEADTFENIEVYNLMCDLLNLTP

APNNGTHGSLNHLLKNPVYTPKHPKEVHPLVQCPFTRNPRDNLGCSCNPSILPIEDFQTQ

FNLTVAEEKIIKHETLPYGRPRVLQKENTICLLSQHQFMSGYSQDILMPLWTSYTVDRND

SFSTEDFSNCLYQDFRIPLSPVHKCSFYKNNTKVSYGFLSPPQLNKNSSGIYSEALLTTNIV

PMYQSFQVIWRYFHDTLLRKYAEERNGVNVVSGPVFDFDYDGRCDSLENLRQKRRVIR

NQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQEDDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK
``` amino acid sequence of NPP1-Fc fusion protein [(187-925)-Fc]    SEQ ID NO: 11

```
EKSWVEEPCESINEPQCPAGFETPPTLLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPI

WVTAKYQGLKSGTFFWPGSDVEINGIFPDIYKMYNGSVPFEERILAVLQWLQLPKDERP

HFYTLYLEEPDSSGHSYGPVSSEVIKALQRVDGMVGMLMDGLKELNLHRCLNLILISDH

GMEQGSCKKY1YLNKYLGDVKNIKVIYGPAARLRPSDVPDKYYSFNYEGIARNLSCREP

NQHFKPYLKHFLPKRLHFAKSDRIEPLTFYLDPQWQLALNPSERKYCGSGFHGSDNVFS

NMQALFVGYGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEKIIKHETLPYGRP

RVLQKENTICLLSQHQFMSGYSQDILMPLWTSYTVDRNDSFSTEDFSNCLYQDFRIPLSP

VHKCSFYKNNTKVSYGFLSPPQLNKNSSGIYSEALLTTNIVPMYQSFQVIWRYFHDTLLR

KYAEERNGVNVVSGPVFDFDYDGRCDSLENLRQKRRVIRNQEILIPTHFFIVLTSCKDTS

QTPLHCENLDTLAFILPHRTDNSESCVHGKHDSSWVEELLMLHRARITDVEHITGLSFYQ

QRKEPVSDILKLKTHLPTFSQEDEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQGNVFSCSV

MHEALHNHYTQKSLSLSPGK
```

-continued amino acid sequence of NPP1-Fc fusion protein [(187-925)-partial hinge Fc
SEQ ID NO: 12

EKSWVEEPCESINEPQCPAGFETPPTLLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPI

WVTAKYQGLKSGTFFWPGSDVEINGIFPDIYKMYNGSVPFEERILAVLQWLQLPKDERP

HFYTLYLEEPDSSGHSYGPVSSEVIKALQRVDGMVGMLMDGLKELNLHRCLNLILISDH

GMEQGSCKKYIYLNKYLGDVKNIKVIYGPAARLRPSDVPDKYYSFNYEGIARNLSCREP

NQHFKPYLKHFLPKRLHFAKSDRIEPLTFYLDPQWQLALNPSERKYCGSGFHGSDNVFS

NMQALFVGYGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEKIIKHETLPYGRP

RVLQKENTICLLSQHQFMSGYSQDILMPLWTSYTVDRNDSFSTEDFSNCLYQDFRIPLSP

VHKCSFYKNNTKVSYGFLSPPQLNKNSSGIYSEALLTTNIVPMYQSFQVIWRYFHDTLLR

KYAEERNGVNVVSGPVFDFDYDGRCDSLENLRQKRRVIRNQEILIPTHFFIVLTSCKDTS

QTPLHCENLDTLAFILPHRTDNSESCVHGKHDSSWVEELLMLHRARITDVEHITGLSFYQ

QRKEPVSDILKLKTHLPTFSQEDDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVFSCSVMHEA

LHNHYTQKSLSLSPGK human IgG1 hinge region
SEQ ID NO: 13
EPKSCDKTHTCPPCP portion of human IgG1 hinge region
SEQ ID NO: 14
DKTHTCPPCP portion of human IgG1 hinge region
SEQ ID NO: 15
PKSCDKTHTCPPCP Linker
SEQ ID NO: 16
(Gly$_4$Ser)$_3$ amino acid motif that is start of soluble NPP1 which includes cysteine rich region
SEQ ID NO: 17
PSCAKE SEQ ID NO: 18
D10 targeting moiety synthetic linker
19
(Gly$_4$Ser)$_n$,

---

What is claimed is:

1. A method for assessing the effect of ectonucleotide pyrophosphatase pyrophosphorylase 1 (NPP1) treatment on intimal hyperplasia in a tip-toe-walking (ttw) mouse model of carotid artery ligation comprising:
  subcutaneously administering a control or NPP1 polypeptide to ttw mice once every other day following carotid ligation;
  harvesting carotid arteries from the control and NPP1 treated ttw mice post-administration of the control or NPP1; and
  histologically analyzing intimal hyperplasia of the harvested carotid arteries from the NPP1 treated ttw mice compared to the control treated ttw mice, thereby assessing the effect of NPP1 treatment on intimal hyperplasia.

2. The method of claim 1, wherein the NPP1 polypeptide is a recombinant human NPP1 polypeptide or a recombinant NPP1 fusion protein comprising an Fc region of an immunoglobulin.

3. The method of claim 1, wherein the intimal hyperplasia results in narrowing of the lumen of a vessel.

4. The method of claim 1, wherein the NPP1 polypeptide has been administered prior to carotid ligation.

5. A method for determining the effect of ectonucleotide pyrophosphatase pyrophosphorylase 1 (NPP1) treatment on intimal hyperplasia in response to a mechanical injury to a vasculature in an animal model of generalized arterial calcification of infancy (GACI), the method comprising:
  measuring intimal hyperplasia in the vasculature of the animal following treatment with an NPP1 polypeptide, wherein the animal has been administered the NPP1 polypeptide prior to mechanical injury, following mechanical injury, or both prior to and following a mechanical injury to the vasculature of the animal, and
  comparing the intimal hyperplasia in the animal treated with the NPP1 polypeptide with a control animal that has been treated with vehicle and not with the NPP1 polypeptide,
  thereby determining the effect of treatment with the NPP1 polypeptide on intimal hyperplasia in response to the mechanical injury of the vasculature.

6. The method of claim 5, wherein the animal model is a mouse.

7. The method of claim 6, wherein the animal model of GACI is a tip-toe-walking (ttw) mouse.

8. The method of claim 6, wherein the mechanical injury is carotid artery ligation.

9. The method of claim 6, wherein the NPP1 polypeptide has been administered prior to mechanical injury or prior to and following mechanical injury.

10. The method of claim 6, wherein the NPP1 polypeptide has been administered subcutaneously.

11. The method of claim 6, wherein the NPP1 polypeptide is a recombinant human NPP1 polypeptide or a recombinant NPP1 fusion protein comprising an Fc region of an immunoglobulin.

12. The method of claim 6, wherein the intimal hyperplasia results in narrowing of the lumen of a vessel.

13. The method of claim 5, wherein the animal model of GACI is a tip-toe-walking (ttw) mouse.

14. The method of claim 5, wherein the mechanical injury is carotid artery ligation.

15. The method of claim 5, wherein the NPP1 polypeptide has been administered prior to mechanical injury, and optionally after or prior to and following mechanical injury.

16. The method of claim 5, wherein the NPP1 polypeptide has been administered subcutaneously.

17. The method of claim 5, wherein the NPP1 polypeptide is a recombinant human NPP1 polypeptide or a recombinant NPP1 fusion protein comprising an Fc region of an immunoglobulin.

18. The method of claim 5, wherein the intimal hyperplasia results in narrowing of the lumen of a vessel.

* * * * *